(12) United States Patent
Pancer et al.

(10) Patent No.: US 9,127,087 B2
(45) Date of Patent: Sep. 8, 2015

(54) HIGH AFFINITY RECOMBINANT SEA LAMPREY ANTIBODIES SELECTED BY A YEAST SURFACE DISPLAY PLATFORM

(75) Inventors: Zeev Pancer, Baltimore, MD (US); Roy A. Mariuzza, Chevy Chase, MD (US); Satoshi Tasumi, Hamamatsu (JP); Carlos A. Velikovsky, Bethesda, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 334 days.

(21) Appl. No.: 13/132,086

(22) PCT Filed: Nov. 25, 2009

(86) PCT No.: PCT/US2009/065852
§ 371 (c)(1),
(2), (4) Date: Jun. 1, 2011

(87) PCT Pub. No.: WO2010/065407
PCT Pub. Date: Jun. 10, 2010

(65) Prior Publication Data
US 2011/0230374 A1  Sep. 22, 2011

Related U.S. Application Data

(60) Provisional application No. 61/118,922, filed on Dec. 1, 2008.

(51) Int. Cl.
*C40B 40/08* (2006.01)
*C07K 14/715* (2006.01)
*C12N 15/10* (2006.01)

(52) U.S. Cl.
CPC ........ *C07K 14/7158* (2013.01); *C12N 15/1037* (2013.01); *C40B 40/08* (2013.01)

(58) Field of Classification Search
None
See application file for complete search history.

(56) References Cited

U.S. PATENT DOCUMENTS
2008/0090282 A1   4/2008  Binder

FOREIGN PATENT DOCUMENTS
WO   2008/016854   2/2008

OTHER PUBLICATIONS

Tanino et al. (2006) Biotechnology Progress vol. 22 pp. 989 to 993.*
Alder MN, et al., (2005) Diversity and function of adaptive immune receptors in a jawless vertebrate. *Science* 310:1970-1973.
Alder MN, et al., (2008) Antibody responses of variable lymphocyte receptors in the lamprey. *Nat Immunol* 9:319-327.
Batista FD, Neuberger MS (1998) Affinity dependence of the B cell response to antigen: A threshold, a ceiling, and the importance of off-rate. *Immunity* 8:751-759.
(Continued)

*Primary Examiner* — Christian Boesen
(74) *Attorney, Agent, or Firm* — Marianne Fuierer; Moore & Van Allen, PLLC

(57) ABSTRACT

The present invention relates to a Yeast Surface Display (YSD) vector for expression of VLR proteins by yeast, wherein the vector includes nucleotide sequences encoding segments of yeast flocculation proteins Flo1p, such as the leader and C-terminal segments, a homologous recombinant cassette and a geneticin/kanamycin resistance gene. The vector can be used for expression of VLR that may be effective in diagnostic applications (e.g., protein chip, immunohistochemistry, flow cytometry), immunoaffinity purification, and for engineering novel fusion proteins.

15 Claims, 22 Drawing Sheets

(56) References Cited

OTHER PUBLICATIONS

Becker RS, Knight KL., (1990) Somatic diversification of immunoglobulin heavy-chain VDJ genes: Evidence for somatic gene conversion in rabbits. *Cell* 63:987-997.
Beckett D, Kovaleva E, Schatz PJ (1999) A minimal peptide substrate in biotin holoenzyme synthetase-catalyzed biotinylation. *Protein Sci* 8:921-929.
Bell, J.K., Mullen, G.E., Leifer, C.A., Mazzoni, A., Davies, D.R. & Segal DM. (2003) Leucine-rich repeats and pathogen recognition in Toll-like receptors. *Trends Immunol.* 24, 528-33.
Binz HK, Amstutz P, Plückthun A., (2005) Engineering novel binding proteins from nonimmunoglobulin domains. *Nat Biotechnol* 23:1257-1268.
Boder ET, Midelfort KS, Wittrup KD., (2000) Directed evolution of antibody fragments with monovalent femtomolar antigen-binding affinity. *Proc Natl Acad Sci USA* 97:10701-10705.
Breinig, F. & Schmitt, M.J. (2002) Spacer-elongated cell wall fusion proteins improve cell surface expression in the yeast *Saccharomyces cerevisiae*. *Appl. Microbiol. Biotechnol.* 58, 637-44.
Chao G, et al., (2006) Isolating and engineering human antibodies using yeast surface display. *Nat Protoc* 1:755-768.
Contreras-Martel, C., Martinez-Oyanedel, J., Bunster, M., Legrand, P., Piras, C., Vernede, X. & Fontecilla-Camps, J.C. (2001) Crystallization and 2.2 A resolution structure of R-phycoerythrin from *Gracilaria chilensis*: a case of perfect hemihedral twinning. *Acta Crystallogr. D. Biol. Crystallogr.* 57, 52-60.
Cornelie, S., Hoebeke, J., Schacht, A.M., Bertin, B., Vicogne, J., Capron, M. & Riveau, G. (2004) Direct evidence that toll-like receptor 9 (TLR9) functionally binds plasmid DNA by specific cytosine-phosphate-guanine motif recognition. *J. Biol. Chem.* 279, 15124-9.
Deng, L., Langley, R.J., Brown, P.H., Xu, G., Teng, L., Wang, Q., Gonzales, M.I., Callender, G.G., Nishimura, M.I., Topalian, S.L. & Mariuzza, R.A. (2007) Structural basis for the recognition of mutant self by a tumor-specific, MHC class II-restricted T cell receptor. *Nat. Immunol.* 8, 398-408.
Diebold, S.S., Kaisho, T., Hemmi, H., Akira, S. & Reis e Sousa, C. (2004) Innate antiviral responses by means of TLR7-mediated recognition of single-stranded RNA. *Science* 303, 1529-31.
Dooley H, Stanfield RL, Brady RA, Flajnik MF, (2006) First molecular and biochemical analysis of in vivo affinity maturation in an ectothermic vertebrate. *Proc Natl Acad Sci USA* 103:1846-1851.
Feldhaus MJ, et al., (2003) Flow-cytometric isolation of human antibodies from a nonimmune *Saccharomyces cerevisiae* surface display library. *Nat Biotechnol* 21:163-170.
Foote J, Eisen HN., (1995) Kinetic and affinity limits on antibodies produced during immune responses. *Proc Natl Acad Sci USA* 92:1254-1256.
Gai, S.A. & Wittrup, K.D. (2007) Yeast surface display for protein engineering and characterization. *Curr. Opin. Struct. Biol.* 17, 467-73.
Han BW, Herrin BR, Cooper MD, Wilson IA, (2008) Antigen recognition by variable lymphocyte receptors. *Science* 321:1834-1837.
Herrin BR, et al., (2008) Structure and specificity of lamprey monoclonal antibodies. *Proc Natl Acad Sci USA* 105:2040-2045.
Huizinga, E.G., Tsuji, S., Romijn, R.A., Schiphorst, M.E., de Groot, P.G., Sixma, J.J. & Gros, P. (2202) Structures of glycoprotein Ibalpha and its complex with von Willebrand factor A1 domain. *Science* 297, 1176-9.
Jiang, T., Zhang, J. & Liang, D. (1999) Structure and function of chromophores in R-Phycoerythrin at 1.9 Å resolution. *Proteins* 34, 224-31.
Kim HM, et al., (2007) Structural diversity of the hagfish variable lymphocyte receptors. *J Biol Chem* 282:6726-6732.
Kumar S, Tamura K, Nei M., (2004) MEGA3: Integrated software for molecular evolutionary genetics analysis and sequence alignment. *Brief Bioinform* 5:150-163.

Lund, J.M., Alexopoulou, L., Sato, A., Karow, M., Adams, N.C., Gale, N.W., Iwasaki, A. & Flavell, R.A. (2004) Recognition of single-stranded RNA viruses by Toll-like receptor 7. *Proc. Natl. Acad. Sci USA* 101, 5598-603.
Marks, J.D. & Bradbury, A. (2004) Selection of human antibodies from phage display libraries. *Methods Mol. Biol.* 248, 161-76.
Meng, G., Grabiec, A., Vallon, M., Ebe, B., Hampel, S., Bessler, W., Wagner, H. & Kirschning, C.J. (2003) Cellular recognition of tri-/di-palmitoylated peptides is independent from a domain encompassing the N-terminal seven leucine-rich repeat (LRR)/LRR-like motifs of TLR2. *J. Biol. Chem.* 278, 39822-9.
Nagawa F, et al., (2007) Antigen-receptor genes of the agnathan lamprey are assembled by a process involving copy choice. *Nat Immunol* 8:206-213.
Pancer Z, et al., (2004) Somatic diversification of variable lymphocyte receptors in the agnathan sea lamprey. *Nature* 430:174-180.
Pancer Z, et al., (2005) Variable lymphocyte receptors in hagfish. *Proc Natl Acad Sci USA* 102:9224-9229.
Pancer Z, Cooper MD, (2006) The evolution of adaptive immunity. *Annu Rev Immunol* 24:497-518.
Pancer Z, Mariuzza RA. (2008) The oldest antibodies newly discovered. Nat Biotechnol. 26:402-3.
Reynaud CA, Garcia C, Hein WR, Weill JC., (1995) Hypermutation generating the sheep immunoglobulin repertoire is an antigen-independent process. *Cell* 80:115-125.
Roach, J.C., Glusman, G., Rowen, L., Kaur, A., Purcell, M.K., Smith, K.D., Hood, L.E. & Aderem, A. (2005)The Evolution of Vertebrate Toll-like Receptors. *Proc. Nat. Acad. Sci. USA* 102, 9577-82.
Rogozin IB, et al., (2007) Evolution and diversification of lamprey antigen receptors: Evidence for involvement of an AID-APOBEC family cytosine deaminase. *Nat Immunol* 8:647-656.
Rutz, M., Metzger, J., Gellert, T., Luppa, P., Lipford, G.B., Wagner, H. & Bauer, S. (2004) Toll-like receptor 9 binds single-stranded CpG-DNA in a sequence- and pH-dependent manner. *Eur. J. Immunol.* 34, 2541-50.
Sato N, et al., (2002) Long anchor using Flo1 protein enhances reactivity of cell surface-displayed glucoamylase to polymer substrates. *Appl Microbiol Biotechnol* 60:469-474.
Satoshi, Tasumi et al. High-affinity lamprey VLRA and VLRB monoclonal antibodies, PNAS, Aug. 2, 2009, vol. 106, No. 31, pp. 12891-12896.
Scholler N, Garvik B, QuarlesT, Jiang S, Urban N (2006) Methodforgeneration of invivo biotinylated recombinant antibodies by yeast mating. *J Immunol Methods* 317:132-143.
Sheridan, C. (2007) Pharma consolidates its grip on post-antibody landscape. *Nat. Biotechnol.* 25, 365-6.
Skerra A., (2007) Alternative non-antibody scaffolds for molecular recognition. *Curr Opin Biotechnol* 18:295-304.
Stanfield RL, Dooley H, Flajnik MF, Wilson IA., (2004) Crystal structure of a shark single-domain antibody V region in complex with lysozyme. *Science* 305:1770-1773.
Sundberg EJ, Mariuzza RA., (2003) Molecular recognition in antigen-antibody complexes. *Adv Protein Chem* 61:119-160.
Swers, J.S., Kellogg, B.A. & Wittrup, K.D. (2004) Shuffled antibody libraries created by in vivo homologous recombination and yeast surface display. *Nucleic Acids Res.* 32, e36.
Teunissen AW, Holub E, van der Hucht J, van den Berg JA, Steensma HY., (1993) Sequence of the open reading frame of the FLO1 gene from *Saccharomyces cerevisiae*. *Yeast* 9:423-427.
Velázquez-Campoy A, Freire E., (2005) ITC in the post-genomic era? Priceless. *Biophys Chem* 115:115-124.
Velikovsky CA, et al., (2009) Structure of a lamprey variable lymphocyte receptor in complex with a protein antigen. *Nat Struc Mol Biol* 16:725-730.
Wark KL, Hudson PJ., (2006) Latest technologies for the enhancement of antibody affinity. *Adv Drug Delivery Rev* 58:657-670.

\* cited by examiner

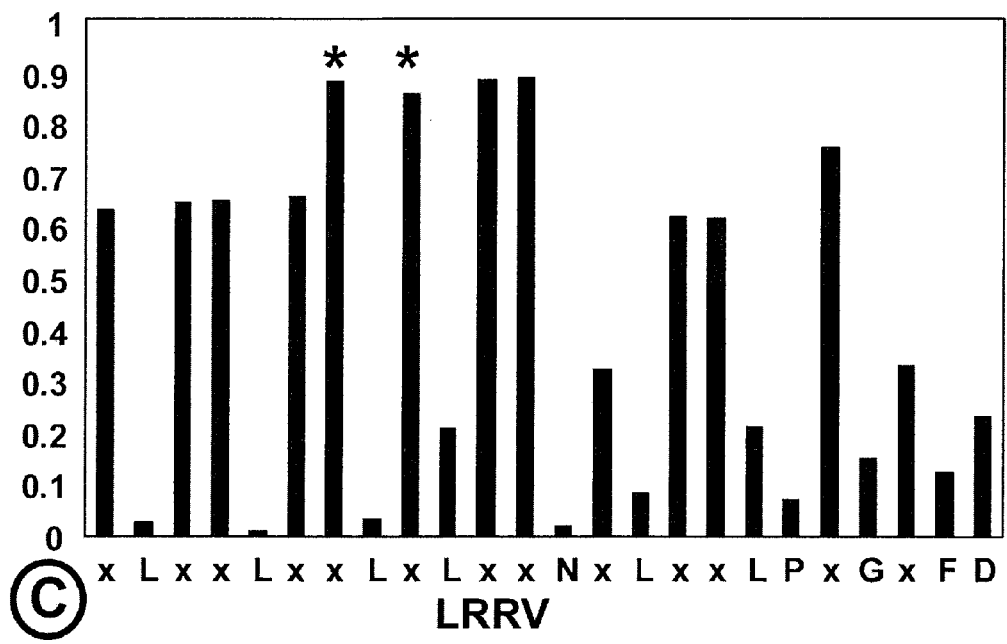
Figure 1 B and C

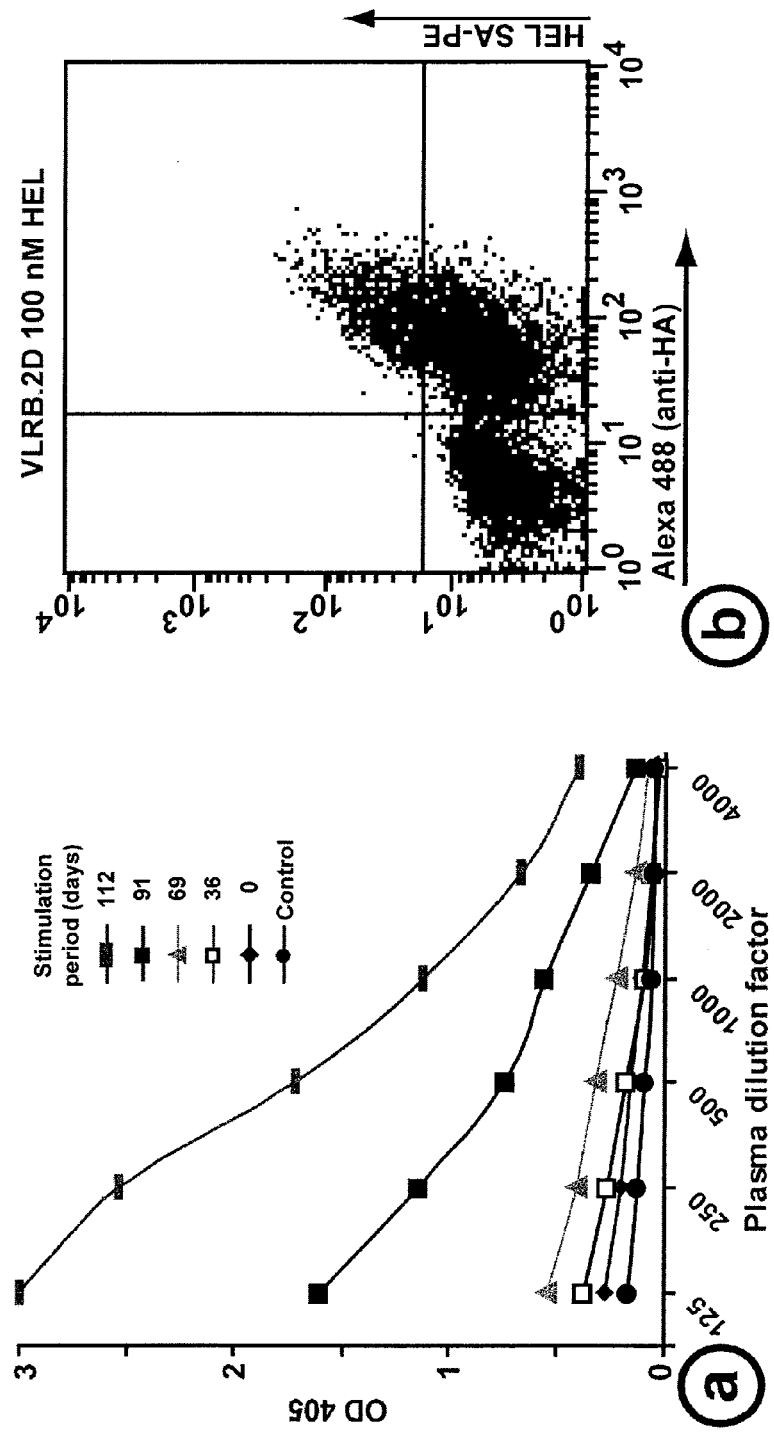
Figure 2 A and B

```
         <---- LRRNT ---->< ---- LRR1 ---->< ---- LRRV1 ---->< ---- LRRV2
VLRB.2D  ACPSQCSCSGTTVDCSGKSLASVPTGIPTTQVLIYLYDNQITKLEPGVFDRLTQLTRLDLDNNQLTVLPAGVFDKLTQLTQLSLNDNQLK
2DMut.1  ..................R......................................L.............................
2DMut.11 ...........................................................N...........................
2DMut.12 .........................................................................................
2DMut.13 ..............................................R..........................................
2DMut.14 .........................................................................................
2DMut.15 ...............................................................................v.........

----><---- CP ----><---- LRRCT ---------------------->
VLRB.2D  SIPRGAFDNLKSLTHWLLNNPWDCACSDILYLSRWISQHPGLVFGYLNLDPDSARCSGTNTPVRAVTEASTSPSKCP  168
2DMut.1  .............................................................................  168
2DMut.11 ..........................W................H...............................  168
2DMut.12 ..........................W................H...............................  168
2DMut.13 .....R....................W................H............K..................  168
2DMut.14 ............................................Y...............T..............  168
2DMut.15 ............................................Y..............................  168
                                                 Hairpin
```

Figure 2D

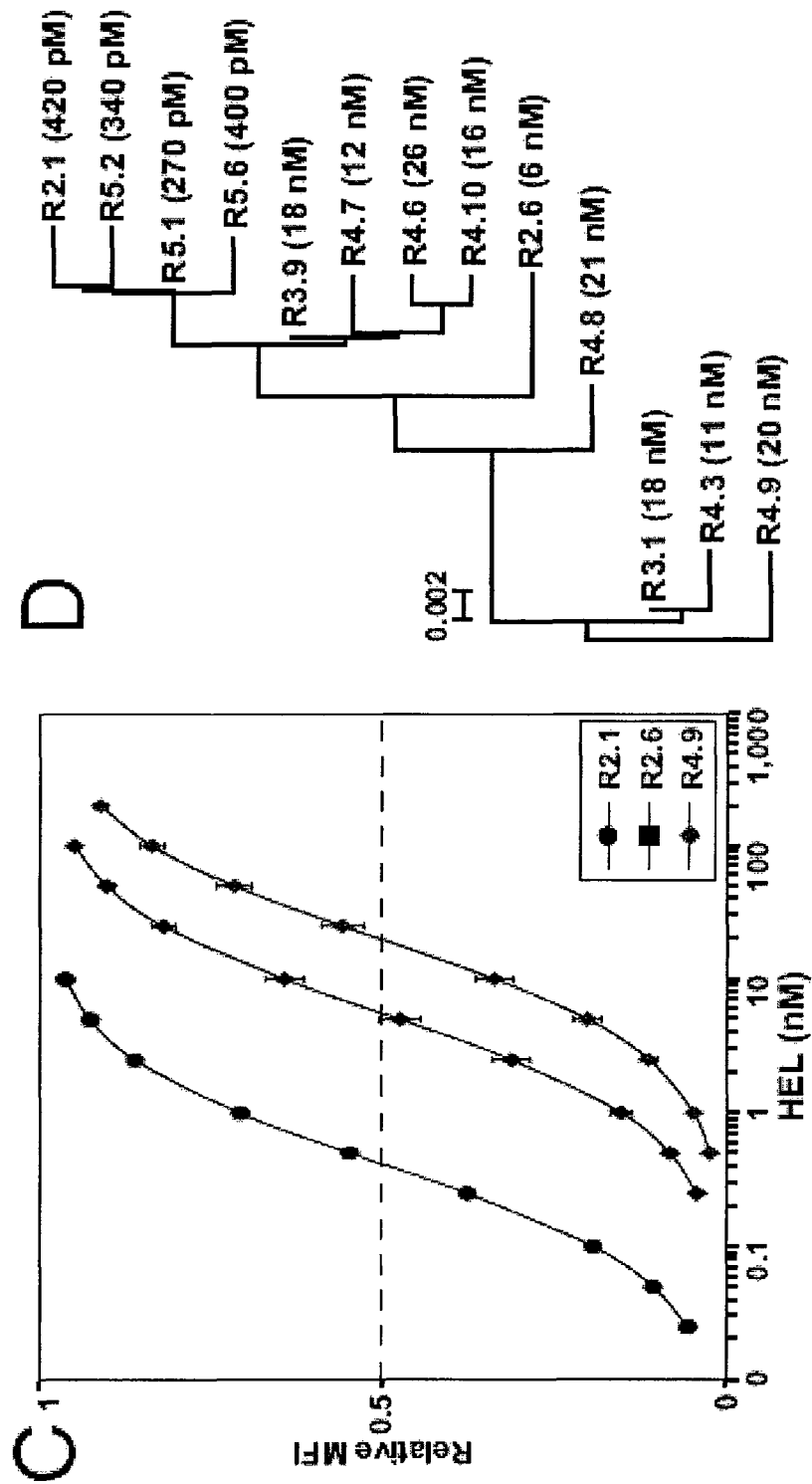
Figure 7 C and D

HIGH AFFINITY RECOMBINANT SEA LAMPREY ANTIBODIES SELECTED BY A YEAST SURFACE DISPLAY PLATFORM

CROSS-REFERENCE TO RELATED APPLICATIONS

This application is filed under the provisions of 35 U.S.C. 0371 and claims the priority of International Patent Application No. PCT/US2009/065852 filed on Nov. 25, 2009, which in turn claims priority to U.S. Provisional Application No. 61/118,922 filed on Dec. 1, 2008, the contents of all are incorporated by reference herein.

STATEMENT OF GOVERNMENT RIGHTS

This invention was made with government support under Grant Number MCB-0614672 awarded by the National Science Foundation. The government has certain rights in the invention.

BACKGROUND OF THE INVENTION

1. Field of the Invention

The present invention relates generally to the field of immunology and, more particularly, the present invention relates to an expression vector for the display of lamprey VLR proteins on a yeast cell surface for selection of high affinity proteins for use in combinatorial libraries.

2. Description of the Related Art Technical Field

At least 10,000 antibodies (Abs) are commercially available for biomedical and biotechnology applications. Abs are used in various medical applications including in vivo diagnostics; as inhibitors of extracellular proteases; as antagonists of cellular receptors or soluble factors; as tissue-targeting vehicles that deliver linked toxic molecules, cytokines or enzymes; or as scavengers of toxic compounds (28). In 2007, the FDA approved 21 Ab-based biopharmaceuticals, mainly for treatment of cancer and autoimmune diseases, approached annual sales of $20 billion (46). Other biotechnology applications for Abs include detection reagents in immunochemical assays such as ELISA, immunoprecipitation, Western blotting, flow cytometry, as biosensors in chip technology and for separation of analytes.

The application of recombinant Abs, as recognition molecules has pitfalls because immunoglobulins (Igs) are large molecules consisting of light and heavy chains linked by disulfide bonds, which requires elaborate and expensive steps for recombinant expression. The complex architecture of the antigen-binding site, formed by six hypervariable loops, three from each chain, further complicates the manipulations required for generation of synthetic Ab libraries. In addition, subunits of Ab fragments often dissociate, or tend to aggregate when fused to effector domains. These technical limitations, as well as major patent restrictions, have driven an intensive search for alternatives to Abs in the form of synthetic binding scaffolds such as ankyrin repeats, fibronectins, lipocalins, protein A, src homology domains and thioredoxin (27, 28). But none of these are natural antigen receptors.

Jawed vertebrates, such as sharks, birds, and mammals, mount a robust humoral response on immune stimulation with foreign antigens. Typically, naïve B lymphocytes bind antigens with low affinity via surface IgM. Subsequently, antibody genes undergo somatic hypermutation, and those clones with highest affinity are selected to produce effective immune responses and form the memory pool (1, 2). Lamprey and hagfish are jawless fish, representatives of the ancestral vertebrate taxon, which evolved rearranging antigen receptors convergently with the jawed vertebrates. But instead of the Ig superfamily domains found in Ig-based antibodies and T cell receptors (TCRs), the variable lymphocyte receptors (VLRs) of lamprey and hagfish consist of highly diverse leucine-rich repeat (LRR) modules (3, 6). LRRs are ancient protein modules that are prevalent building blocks of animal and plant pattern recognition molecules, such as Toll and Toll-like receptors, nucleotide oligomerization domain (NOD), LRRs, and plant disease-resistance genes, which are triggered by an exceptionally diverse array of ligands (7). Interestingly, however, VLRs are not related to these pattern recognition molecules, but instead are closely related to the vertebrate-specific von Willebrand factor receptor GpIbα, a member of the family of platelet LRR-containing hemostatic receptors (6). Jawless vertebrates thus evolved their rearranging antigen receptors from LRR scaffolds, elaborating the only known adaptive immune system not based on Ig or on TCR (6).

However, little is known about the antigen-binding properties of VLRs, or about how the naïve VLR repertoire develops into a protective shield in immune-stimulated animals. Thus it would be advantageous to use the natural antigen antigen-binding properties of VLRs to develop systems and methods for diagnostic applications, immunoaffinity purification, and engineering novel fusion proteins that do not include the shortcomings of Ig antibodies.

SUMMARY OF THE INVENTION

The present invention relates to the use of the only natural adaptive immune system that is not based on Igs and found in lamprey and hagfish that are jawless vertebrates that produce VLRs. VLRs have great biotechnological potential in diagnostic applications (e.g., protein chip, immunohistochemistry, flow cytometry), for immunoaffinity purification, and for engineering novel fusion proteins. Thus, the present invention provides for the production of high affinity VLR for diverse ligands having dissociation constants ($K_D$) in the micrometers and nanometer In one aspect, the present invention relates to a Yeast Surface Display (YSD) vector for expression of a VLR protein comprising:
  a) a nucleotide sequence encoding for the VLR protein;
  b) nucleotide sequences encoding the leader and C-terminal of yeast flocculation protein Flo1p or segments having substantially the same activity or function thereof; and
  c) a homologous recombination cassette consisting of two direct repeats separated by a linker with a restriction site for plasmid linearization.

A further improvement in the YSD vector is the inclusion of a geneticin/kanamycin resistance gene and using a growth medium that includes yeast peptone and sugar, supplemented with G418 for plasmid selection.

In another aspect, the present invention relates to a Yeast Surface Display (YSD) vector for expression of a VLR protein comprising:
  a) a nucleotide sequence encoding for the VLR protein;
  b) nucleotide sequences encoding the leader and C-terminal of yeast flocculation protein Flo1p comprising of SEQ ID NOs.: 6 and 7 respectively or sequences having at least 90% homology and having substantially the same activity or function; and a homologous recombination cassette consisting of two direct repeats separated by a linker.

In yet another aspect, the present invention relates to a high-throughput platform for selection of recombinant antigen-binding VLR proteins, the system comprising:
a) providing yeast strains of *Saccharomyce cerevisiae* and
b) transfecting the yeast with an expression vector comprising:
   a nucleotide sequence encoding for at least one VLR protein;
   nucleotide sequences encoding for both the leader and C-terminal of yeast flocculation protein Flo1p; and a homologous recombination cassette consisting of two direct repeats separated by a linker with a restriction site for plasmid linearization; and
c) culturing the yeast for expression and displaying of the VLR proteins on the surface of the yeast.

Another aspect relates to the production of VLR proteins having high affinity for an antigen of choice, the method comprising:
a) immunizing a Lamprey with the antigen and collecting plasma containing the VLR proteins formed in response to the antigen;
b) determining nucleotide sequence encoding such VLR proteins;
c) preparing an expression vector comprising:
   i. a nucleotide sequence encoding for the VLR protein;
   ii. nucleotide sequences encoding for both the leader and C-terminal of yeast flocculation protein Flo1p; and a homologous recombination cassette consisting of two direct repeats separated by a linker with a restriction site for plasmid linearization;
d) transfecting a yeast strain;
e) culturing the yeast for expression and displaying of the VLR proteins on the surface of the yeast; and
f) measuring the binding affinity.

The method for determining binding affinity may further include subjecting such nucleotide sequence encoding the VLR protein to mutagenesis and repeat until affinity increases for antigen of choice.

Other aspects and advantages of the invention will be more fully apparent from the ensuing disclosure and appended claims.

DETAILED DESCRIPTION OF THE INVENTION

Figure 1:
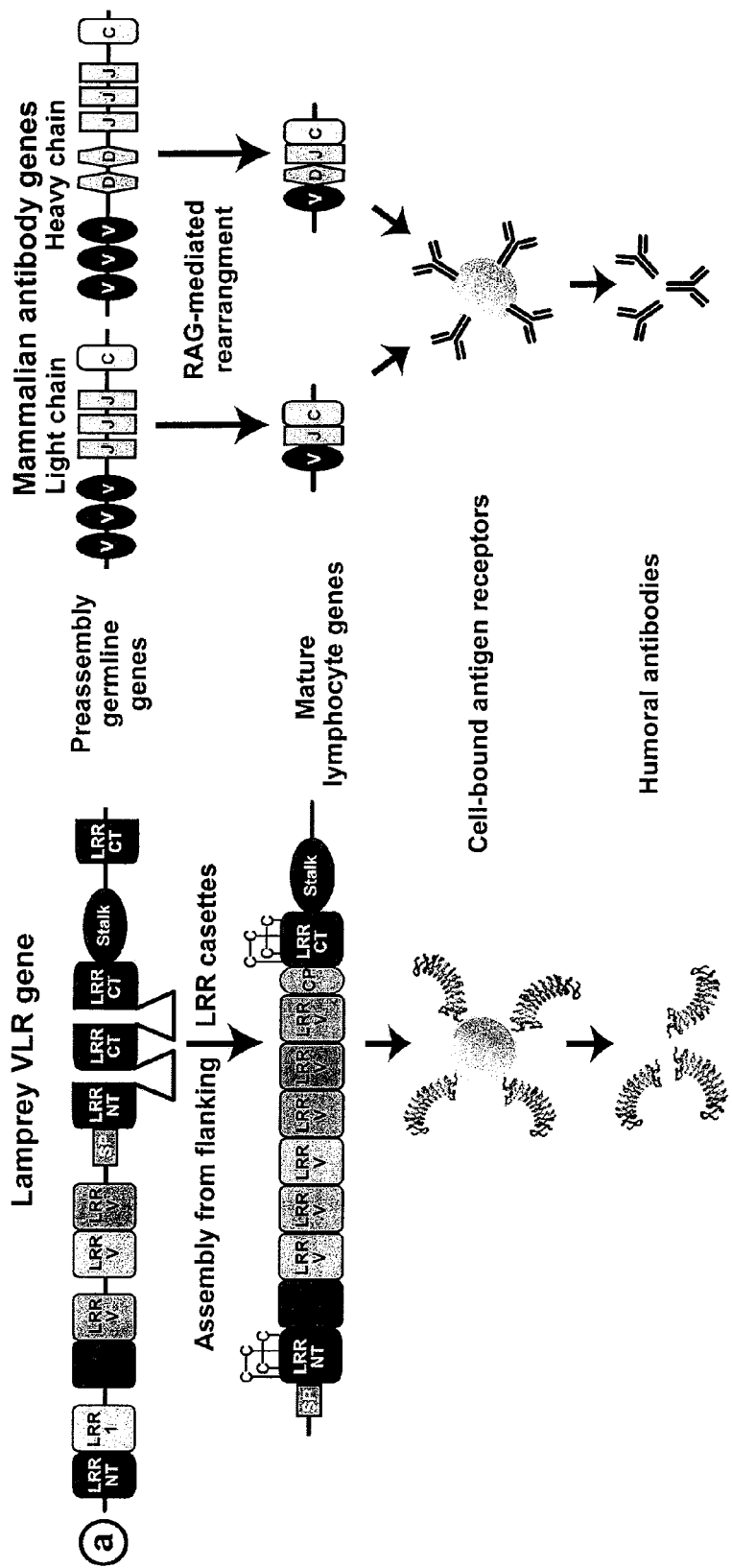
FIG. 1 shows in A the assembly of lamprey VLRs, compared with the V(D)J-rearrangement of mammalian Abs. VLR genes are assembled by sequential insertion of LRR cassettes from flanking arrays into the incomplete germline gene, via gene conversion. Ab genes are assembled via RAG-mediated joining of Ig gene fragments. Mature antigen receptors in both cases are expressed on the surface of lymphocytes, and can be secreted to the plasma. A VLR comprises a set of highly diverse LRR modules capped by disulfide-bonded N-terminal and C-terminal LRR modules (LRRNT, LRRCT). The 25-residue LRR1 is followed by up to nine 24-residue LRRVs, and a 16-residue LRR, the connecting peptide (CP). The invariant portions of VLRs include a secretion peptide (SP) and an 81-residue C-terminus that contains a threonine/proline-rich stalk and a GPI surface anchorage motif. B. Alignment of consensus LRR sequences from animal, yeast and bacterial proteins. (Lamprey SEQ ID NO: 56, Toll Like (SEQ ID NO: 57; CD42b SEQ ID NO: 58; RI SEQ ID NO: 59; Yeast SEQ ID NO: 60; Bacterial SEQ ID NO: 61) RI—ribonuclease inhibitor; x—any residue; φ—hydrophobic residue (modified from 31). C. Variability plots for the lamprey LRRV module. The mean of pairwise differences in residues per site, calculated for modules from 517 unique VLR sequences. Consensus residues are indicated; variability values: 0=single residue in that position, 1=all 20 residues equally represented; *—positively selected residue predicted on the β-strand (SEQ ID NO 62).

In accordance with the present invention there may be employed conventional molecular biology, microbiology, and recombinant DNA techniques within the skill of the art. Such techniques are explained fully in the literature and the contents hereby incorporated by reference herein. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

As used herein, the term "affinity maturation" shall refer to a process of successive mutation and selection by which antibodies such as VLRA and/or VLRB of higher affinity are selected.

As used herein, the term "ligand" shall refer to a molecule that is bound specifically by a particular protein.

As used herein, the term "antigen" shall refer to a ligand that is bound specifically by an antibody of the present invention.

As used herein, the term "Fluorescence Activated Cell Sorting" or "flow cytometry" shall refer to a method for sorting cell populations on the basis of differential fluorescent labeling.

As used herein the term "DNA coding sequence" shall refer to a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

As used herein, the terms "polypeptide," "protein" and "peptide" are used interchangeably to denote a sequence polymer of at least two amino acids covalently linked by an amide bond, regardless of length or post-translational modification (e.g., glycosylation, phosphorylation, lipidation, myristilation, ubiquitination, etc.). D- and L-amino acids, and mixtures of D- and L-amino acids are also included.

As used herein, the term "substantially the same activity or function," when used in reference to a flo1p leader or C-terminal protein so modified, means that the polypeptide retains most, all or more of the activity associated with the unmodified polypeptide, as described herein or known in the art.

Modified flo1p leader or C-terminal proteins having substantially the same activity or function, included herein can be identified through a routine functional assay. For example, by using antibody binding assays or co-receptor binding assays.

As used herein, the terms "homology" or "homologous," used in reference to polypeptides, refers to amino acid sequence similarity between two polypeptides. When an amino acid position in both of the polypeptides is occupied by identical amino acids, they are homologous at that position. Thus, by "substantially homologous" means an amino acid sequence that is largely, but not entirely, homologous, and which retains most or all of the activity as the sequence to which it is homologous.

As the modified flo1p leader or C-terminal protein will retain activity or function associated with unmodified flo1p leader or C-terminal protein, modified flo1p leader or C-terminal protein polypeptides will generally have an amino acid sequence "substantially identical" or "substantially homologous" with the amino acid sequence of the unmodified polypeptide. As used herein, the term "substantially identical" or "substantially homologous," when used in reference to a polypeptide sequence, means that a sequence of the polypeptide is at least 70%, alternatively 85%, more likely 90%, and most likely 95% homology to a reference polypeptide. For polypeptides, the length of comparison to obtain the above-described percent homologies between sequences will generally be at least 25 amino acids or alternatively at least 50 amino acids, more likely at least 100 amino acids, and most likely 200 amino acids or more.

As set forth herein, substantially identical or homologous polypeptides include additions, truncations, internal deletions or insertions, conservative and non-conservative substitutions, or other modifications located at positions of the amino acid sequence which do not destroy the function of the flo1p leader or C-terminal protein (as determined by functional assays, e.g., as described herein). A particular example of a substitution is where one or more amino acid is replaced by another, chemically or biologically similar residue. As used herein, the term "conservative substitution" refers to a substitution of one residue with a chemically or biologically similar residue. Examples of conservative substitutions include the replacement of a hydrophobic residue, such as isoleucine, valine, leucine, or methionine for another, the replacement of a polar residue for another, such as the substitution of arginine for lysine, glutamic for aspartic acids, or glutamine for asparagine, and the like. Those of skill in the art will recognize the numerous amino acids that can be modified or substituted with other chemically similar residues without substantially altering activity.

As used herein, the terms "nucleic acid," "polynucleotide," "oligonucleotide," and "primer" are used interchangeably to refer to deoxyribonucleic acid (DNA) or ribonucleic (RNA), either double- or single-stranded, linear or circular. RNA can be unspliced or spliced mRNA, rRNA, tRNA, or antisense RNAi. DNA can be complementary DNA (cDNA), genomic DNA, or an antisense. Specifically included are nucleotide analogues and derivatives, such as those that are resistant to nuclease degradation, which can function to encode the invention flo1p leader and/or C-terminal proteins. Nuclease resistant oligonucleotides and polynucleotides are particularly useful for the present nucleic acid vaccines described herein.

As used herein the terms "transcriptional and translational control sequences" shall refer to DNA regulatory sequences, such as promoters, enhancers, polyadenylation signals, terminators, and the like, that provide for the expression of a coding sequence in a host cell.

As used herein the terms "promoter sequence" shall refer to a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein the "primer" shall refer to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

For propagation or expression in cells, polynucleotides described herein can be inserted into a vector of the present invention. The term "vector" refers to a plasmid, virus, or other vehicle known in the art that can be manipulated by insertion or incorporation of a nucleic acid. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including promoters present within an expression vector, are included to facilitate proper transcription and translation (e.g., splicing signal for introns, maintenance of the correct reading frame of the gene to permit in-frame translation of mRNA and stop codons). In vivo or in vitro expression of the polynucleotides described herein can be conferred by a promoter operably linked to the nucleic acid.

As used herein, the term "reporter gene" shall refer to a coding sequence attached to heterologous promoter or enhancer elements and whose product is easily and quantifiably assayed when the construct is introduced into tissues or cells.

As stated above, jawless fish are members of the ancestral vertebrate taxon and the only remaining sister group of jawed vertebrates such as shark, birds and mammals. Like all other vertebrates, lamprey and hagfish have circulating lymphocytes equipped with highly diverse cell surface and secreted antigen receptors (FIG. 1A). Instead of Ig domains however, VLRs consist of leucine-rich repeats (LRRs)—structural modules that form a horseshoe-shaped fold with an interior parallel β-sheet and an exterior array of helices (10). The LRR modules are ancient motifs found in over 2,000 proteins from viruses, bacteria, archaea and eukaryotes (FIG. 1B), including many of the cardinal innate microbial recognition proteins of animals and plants, such as Toll-like receptors (TLRs), the cytoplasmic nucleotide-binding site (NBS)-LRR proteins and the LRR-containing plant Disease Resistance genes (7).

VLRs are generated in lymphocytes by a process of DNA recombination (FIG. 1A). Each VLR is assembled from multiple LRR-encoding cassettes, selected from an array of several hundred cassettes that flank the germline VLR gene. The selected cassettes are sequentially incorporated into the germline gene framework by gene conversion, to form a functional mature VLR with a unique diversity region. The diversity region of VLRs consists of a set of LRR modules, each with a highly variable amino acid sequence: a 27-31 residue N-terminal LRR (LRRNT), one 25-residue LRR (LRR1), up to nine 24-residue LRRs (LRRVs), one 16-residue truncated LRR designated connecting peptide (CP) and a 48-63 residue C-terminal LRR (LRRCT). The LRRNT and LRRCT are stabilized by two sets of intramodular disulfide bonds and cap both ends of the solenoid fold of the diversity region.

The assembly of VLRs by iterated cassette insertions, with frequent recombination events within the boundaries of the LRR modules, generates a vast repertoire of receptors estimated at over $10^{14}$ unique VLRs, which is sufficiently diverse to recognize molecular determinants of most, if not all, potential pathogens (5, 6). The most diverse LRR module is the 24-residue LRRV, which is a mosaic of conserved scaffold residues and highly variable sites, similar to most types of LRR modules from animals, plants, yeast and bacteria (FIGS. 1 B and C). The LRRVs consist of 11 conserved residues that are interspersed with hypervariable sites, some of which are positively selected sites located on the predicted solvent exposed β-strand that forms the concave surface of the VLR. The conserved residues form the hydrophobic core of the LRR module, whereas the canonical structure of the LRR is unaffected by physiochemical properties of residues in the hypervariable sites, and these may account for much of the diversity in VLR ligand binding sites (5).

The LRRNT and LRRCT modules, which cap both sides of the horseshoe-shaped solenoid fold, are also highly diverse in sequence. In the LRRCT, most of the diversity maps to a predicted 5-14 residue hairpin loop located between the α-helix and the first β-strand of the module. This distinctive loop is absent from the LRRCT of other animal LRR-containing proteins, except for the platelet glycoprotein receptor GPIbα, which has a 17-residue insert in its LRRCT (6). Interestingly, the crystal structure of human GPIbα in complex with the vWA domain of von Willebrand factor, showed the LRRCT insert forming an extended hairpin that projects across the concave surface in contact with the vWF (38). The highly variable loops in LRRCT of the VLRs may therefore similarly interact with antigens, regulating size and affinity of ligands accommodated by the concave surface.

The LRR-containing innate immune receptors of vertebrates are triggered by a remarkably diverse array of ligands. A short list of TLR ligands includes lipopeptide, lipoteichoic acid, mycobacterial lipoarabinomannan, neisserial porins, bacterial tripalmitoylated and mycoplasmal diacylated lipoproteins, lipopolysaccharide, peptidoglycan, bacterial flagellin, single-stranded and double-stranded RNA, unmethylated CpG-DNA motifs, heme motifs, pathogen and host derived proteins and oligosaccharides derived from heperan sulfate and hyaluronic acid (42, 34, 36, 40, 45, 44). The prevalence of LRRs in pattern recognition receptors of both plants and animals underscores their extraordinary competence for microbial recognition (7).

The VLRs were only recently discovered (3) but there is already solid evidence for antigen recognition by VLRs from immunized lamprey. Within several weeks after intraperitoneal injection of *Bacillus anthracis* spore coats, the lamprey plasma contained VLRs that reacted specifically with the anthrax spores, and with the BclA glycoprotein component of the spore, which is the major antigenic determinant in mice (5). Lamprey larvae and adults were immunized with hen egg lysozyme (HEL), which is commonly used in structural studies of the antigen-binding properties of jawed vertebrate Abs (13). Within four months the lamprey produced a high titer anti-HEL VLR response in plasma (FIG. 2A). Recently it was reported that lamprey immunized with human blood group O erythrocytes, produced VLRs that specifically recognized the H-trisaccharide antigen (8). Also secreted recombinant VLRs were produced in the cell line HEK-293T, which were cloned from lamprey immunized with the anthrax spore coat. Of 212 VLR transfectants that were assayed for antigen recognition, 14 were identified as positive for BclA, seven of which could discriminate between the C-terminal BclA domain of *B. anthracis* and that of *B. cereus*, which differ by only 14 of 134 residues (11). The nucleotide sequences of these VLRs were closely related and, as predicted, the few variable positions mapped to the β-sheet at the VLR concave surface, and to the predicted hairpin loop region in LRRCT. The secreted anti-BclA VLRs were oligomeric, comprising four or five disulfide-linked dimeric subunits, somewhat akin to vertebrate IgM antibodies. They were extremely stable, retaining antigen-binding activity after elution from a BclA affinity column at pH>11 and after storage for one year in the refrigerator, one month at room temperature or 36 h at 56° C. Remarkably, one of these VLRs agglutinated anthrax spores 1,000-fold more efficiently than an equivalent amount of a mouse monoclonal antibody, demonstrating its high avidity for the antigen.

These preliminary studies show an adaptive immune response mediated by non-Ig receptors, and pave the way to biotechnological applications of the VLRs, which may turn to be excellent protein scaffolds for molecular recognition (27, 43). VLRs can be used for diagnostic applications (e.g., protein chip, flow cytometry, immunohistochemistry, enzyme-linked immunosorbent assays), for immunoaffinity purification and for the creation of novel fusion proteins. In addition, lamprey VLRs can provide a rich source of reagents that recognize mammalian antigens invisible to Ig-based Abs due to self-tolerance. The fact that VLRs are modular single-chain polypeptides makes them amenable to molecular engineering, and the presence of usually two or three hypervariable solvent-exposed sites per module should facilitate targeting of these residues by random mutagenesis in vitro to increase affinity or alter specificity. However, in order to fully explore the potential of VLRs as novel binding proteins, an expression platform is necessary to screen VLR libraries that are orders of magnitude larger than is possible with the HEK-293T system (11).

Figure 8:
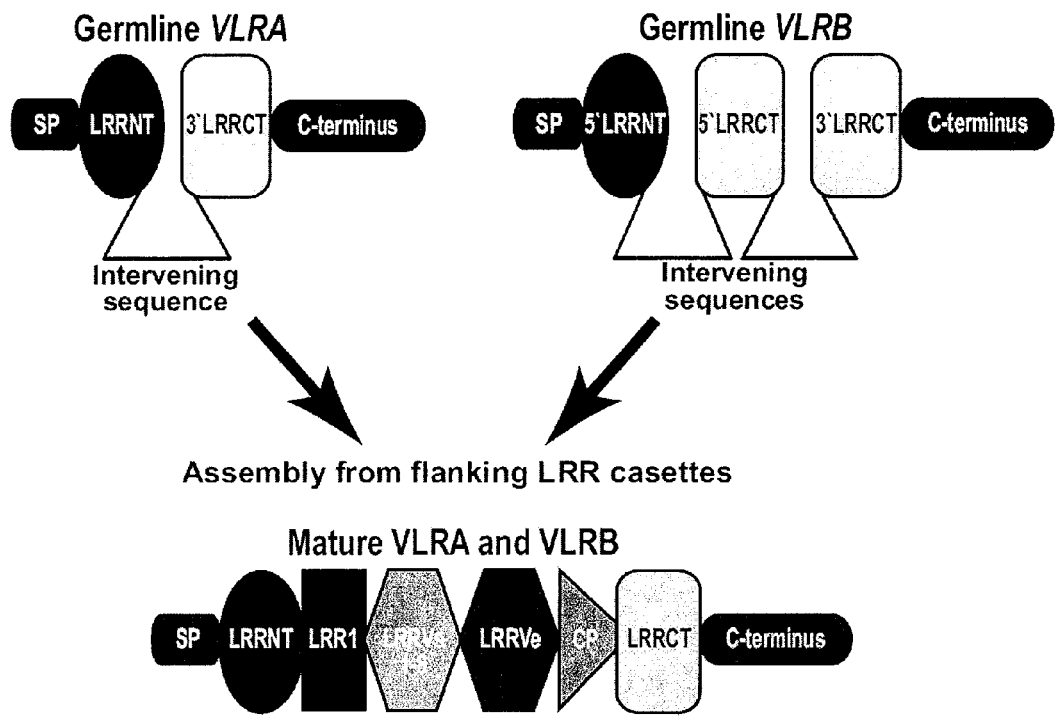
FIG. 8 shows assembly of lamprey germline VLR genes into mature VLRs. The germline genes are nonfunctional, consisting only of the invariant portions: N-terminal signal peptide (SP), a complete or 3'-truncated portion of the LRRNT, 1 or 2 noncoding intervening sequences, 1 or 2 truncated portions of the LRRCT, and a stalk-like C terminus that includes a glycosyl phosphatidylinositol (GPI) membrane anchorage motif, which tethers the VLR to the lymphocyte surface. The diversity regions of mature VLR genes consist of LRRNT of 27-34 residues, one 25-residue LRR (LRR1), up to nine 24-residue LRRs (LRRVs, the terminal one designated LRRVe), one 16-residue truncated LRR designated CP, and 48-63 residue LRRCT. The mature VLR genes are assembled by sequential insertion of LRR-encoding cassettes, from arrays of the hundreds of cassettes flanking each gene (not shown), into the incomplete germline genes via a gene conversion-like process. The germline VLR gene portions of LRRNT and LRRCT serve as docking sites for the incoming LRR cassettes.

There are 2 types of VLR genes (4, 6), VLRA and VLRB, expressed by mutually exclusive lymphocyte populations (8). To form mature functional receptors, germline VLR genes undergo DNA recombination, whereby each VLR is assembled from multiple LRR-encoding cassettes selected from arrays of several hundred cassettes flanking each VLR gene. Mature VLRs consist of N-terminal leaders and C-terminal stalk-like cell surface-anchoring domains encoded by the germline VLR genes. Each VLR has a unique diversity region. Only small amino- and carboxy-terminal portions of the diversity regions are contributed by the germline genes (FIG. 8); these serve as docking sites for the sequential incorporation of LRR cassettes via a gene conversion-like process (6, 9).

The diversity regions in VLRA and VLRB consist of sets of LRR modules, each with a highly variable sequence: a 27- to 34-residue N-terminal LRR (LRRNT), one 25-residue LRR (LRR1), up to nine 24-residue LRRs (LRRVs; the terminal one designated LRRVe), one 16-residue truncated LRR designated the connecting peptide (CP), and a 48- to 63-residue C-terminal LRR (LRRCT). The LRRNT and LRRCT are stabilized by 2 sets of intramodular disulfide bonds that serve to cap both ends of the curved, solenoid-shaped diversity region (10). The assembly of VLRs by iterated cassette insertions, with frequent recombination events within boundaries of the LRR modules, generates a vast repertoire of receptors estimated at more than $10^{14}$ unique VLRs, of comparable magnitude to mammalian antibodies and TCRs (5, 6). Thus, VLRs may be excellent single-chain alternatives to Ig-based antibodies for biotechnology applications, because both antigen receptors were optimized over hundreds of millions of years of evolution.

Recent evidence indicates antigen recognition by plasma VLRB from immunized lamprey. Within 4-8 weeks after i.p. injection of Bacillus anthracis spores, the lamprey plasma contained VLRB antibodies that reacted specifically with the spores and with their BclA glycoprotein component (5, 11). Recombinant VLRBs from anthrax-immunized larvae were cloned and expressed in a mammalian cell line. Some of these could discriminate between the C-terminal domain of BclA of *B. anthracis* and *B. cereus*, which differ by only 14 of 134 residues, indicating the high specificity that VLRs can achieve. Both plasma VLRB and the recombinant antianthrax antibodies formed multimers, comprising 4 or 5 disulfide-linked dimeric subunits, which avidly bound BclA. But monomeric forms of the antianthrax VLRB were weak BclA binders, indicating that high-avidity binding requires oligomerization (11).

The present invention relates to the antigen-binding properties of lamprey VLRA and VLRB antibodies obtained from large VLR yeast surface display (YSD) libraries, which were constructed from antigen-stimulated and naïve animals and using the novel vector of the present invention. This powerful high-throughput platform enabled the isolation of monoclonal VLRs that specifically bind proteins and carbohydrates with affinities ranging from micromolar to subnanomolar. Also in vitro affinity maturation of VLRB antibodies was demonstrated with up to a 1,300-fold improvement in antigen-binding properties.

Notably, for high-throughput cloning of antigen-binding VLRs the *E. coli*-based phage display system (41) was initially used. However, this system was unsuccessful, as nearly all the putative antigen-binders were subsequently found to be completely non-specific. This lack of specificity ("stickiness") can be attributed to the inability of most VLRs to fold properly in the reducing environment of *E. coli* cytoplasm, which may prevent formation of disulfide bonds in the capping modules, resulting in misfolding and aggregation of VLRs. Nonetheless, a single true antigen-binding clone, VLRB.2D, was identified which was found to recognize HEL with a dissociation constant ($K_D$) of 20 μM, as measured by surface plasmon resonance (SPR) (FIG. 3A).

To overcome the shortcomings of the *E. coli*-based phage display system, yeast surface display (YSD) was tested for the VLR proteins in *Saccharomyces cerevisiae*. YSD is a eukaryotic expression platform with an efficient secretory oxidative protein folding machinery and glycosylation pathway, which is amenable to high-throughput screens. The YSD vector pCTCON2 and yeast strains were initially used. The pCTCON2 vector was created for expression of various native and engineered Ig-containing proteins as well as other synthetic ligand-binding protein scaffolds. However, upon attempting to sort antigen-binding VLRs using a fluorescence activated cell sorter (FACSort, BD Biosciences), irreproducible results were repeatedly encountered. Sorted populations did not enrich in spite of being selected from distinct populations of seemingly high-level antigen binders. It seemed that unstable phenotypes were being enriched instead of stable genotypes.

To overcome this difficulty, a custom tailored YSD vector was constructed for VLR expression (FIG. 4A), based on N-terminal fusion to the yeast flocculation protein Flo1p (16). The Flo1p is 1537 amino acids long, (SEQ ID NO.: 3) with a 24-residue leader (SEQ ID NO.: 4), then residues 1000-1081 feature a mannose-binding lectin-like domain and 18 flocculin repeats, which are important for yeast flocculation. Residues 1085-1537 (SEQ ID NO.: 5) encode a predicted stalk-like structure and a C-terminal GPI cell surface anchorage motif. Portions of the Flo1p C-terminus were previously shown to improve yeast surface expression of a test hemagglutinin (HA) tag (32).

As such, the novel vector of the present invention includes the Flo1p leader connected via a short linker to the cloning sites region, followed by a set of detection and processing tags and then the C-terminal Flo1p stalk and anchor (FIG. 4B). The vector includes a geneticin/kanamycin resistance gene for selection both in yeast and *E. coli*, instead of the TRP1 gene in pCTCON2 used to complement tryptophan deficiency in the yeast host. The expensive and labor intensive preparation of defined selective synthetic culture media has now been replaced with a simple formula of rich yeast peptone and sugar, supplemented with 50-100 μg/ml G418 for plasmid selection.

The new vector was tested and a remarkable improvement in the display of Flo1p-anchored VLRs was evident compared with pCTCON2. VLR displaying cells now appeared in a narrow and sharp flow cytometry profile, with clearly distinct ligand-binding populations (FIGS. 2 B, C and D). The last innovation in the novel vector of the present invention is a cassette for intra-plasmid homologous recombination (FIG. 4C). To take advantage of the high efficiency of yeast transformation with linear DNA, a cassette was created in the pYSD2 consisting of two 49-bp direct repeats, separated by an 8-bp recognition site for the PmeI endonuclease. The linearized plasmid is circularized in vivo by homologous recombination between the two direct repeats, leaving a single repeat in the recombined pYSD2 plasmid.

The present invention discloses a powerful new system for engineering antibody affinity and specificity, by constructing a microbial analog of the mammalian immune system's B cell repertoire. VLR were displayed on the surface of yeast cells by genetic fusion with Flop1p segments, that being the C-terminal and leader segments. After mutation, variants were selected on the basis of improved binding characteristics with fluorescently labeled targets.

EXAMPLES

Methods and Materials

Antigens: 13-gal (Calbiochem), CTB (Invitrogen), HEL (Sigma), RPE (Pierce), and blood group antigen type A (tri)-PAA-biotin and type B (tri)-PAA-biotin (Glycotech). Proteins were biotinylated with an EZ-Link NHS-PEO4 biotinylation kit (Pierce) a level of 1-3 mols of biotin per mol of antigen.

Lamprey Immunization. Metamorphosed lamprey, 20-25 cm long, were purchased from Acme Lamprey Co. Five animals were sedated by immersion for 10 min in 200 mg/L of MS222 (Sigma) and injected i.p. with a mixture of 100 L of 10 mg/mL of HEL in 0.67×PBS, emulsified with 100 L of FCA (Pierce), per animal. On days 36, 69, and 91 post immunization, 3 of the animals were boosted i.p. with the same antigen dose in FCA, and 2 lamprey were boosted i.v. via the tail vain, with 1 mg of HEL in 300 L of 0.67×PBS. Before immunization and boosting, a 0.5-mL blood sample was individually drawn from the tail vain into a syringe filled with 0.5 mL of anticoagulant PBS (0.57×PBS and 30 mM EDTA). On day 112, the lamprey were euthanized by immersion in 5 g/L of MS222 for 10 min, after which their blood was collected and diluted with an equal volume of anticoagulant PBS. There were $1-3 \times 10^6$ lymphocytes per mL of blood, and 5-8 mL of blood was collected per animal. Buffy coat leukocytes were collected by 5 min of centrifugation at 50×g, and the plasma was separated from leukocytes by a 5-min spin at 300×g. Leukocytes were saved for RNA extraction, and the plasma was tested in ELISA with an anti-VLRB mAb (29). Anti-HEL VLRB reactivity was strong in the plasma of 1 of the 2 surviving animals that were boosted with antigen in FCA; the other plasma showed weak signals. No response was detected in plasma from the i.v.-boosted lamprey.

Lamprey larvae, 10-15 cm long, were purchased from Lamprey Services. Sedated larvae were immunized by i.p. injections of 100 g of antigen in 75 L of 0.67×PBS containing $10^7$ E. coli BL21 cells (Novagen) heat-killed by a 10-min exposure to 65° C. Immunizations of 5-10 larvae with HEL, 13-gal, or $10^7$ sheep erythrocytes (Colorado Serum) were repeated 4 times at biweekly intervals. After 9-10 weeks, the animals were euthanized, their tails were severed, and blood was collected and treated as for the adults. There were $1-3 \times 10^6$ lymphocytes per mL of larval blood, and about 0.25 mL of blood was collected per animal. All animal procedures were approved by the University of Maryland Biotechnology Institute's Institutional Animal Care and Use Committee.

pYSD2 Vector: Plasmid pYSD2 (FIG. 4A) was constructed on the backbone of pPICZ-a (Invitrogen). The NcoI+ BmgBI Zeocin gene was replaced with kanamycin, PCR amplified from pET24b (Novagen) using Expand High Fidelity (Roche). The GAL1 promoter region (positions 361-816 in gb K02115.1) was amplified from plasmid pCTCON2 (from K.D.W.) and inserted instead of the AOX1 promoter. Oligonucleotides encoding the Flo1p leader peptide and Flo1p C terminus amplified from yeast DNA (positions 1497-1574 (SEQ ID NO.: 6) and 4756-6114 (SEQ ID NO.: 7) in gb EF670005.1, (SEQ ID NO.: 8) (nucleotide)) were assembled with a spacer containing 2 different SfiI sites, for directional cloning of VLR, and an HA tag. The BspHI CEN6/ARS4 insert from pCTCON2 was then cloned into the PciI site. A cassette for intraplasmid homologous recombination, consisting of two 49-bp direct repeats separated by a linker with the PmeI restriction site, was generated from oligonucleotides and cloned into the BspHI site.

YSD Library Construction. Lymphocyte RNA was extracted with TRIzol reagent (Invitrogen), and mRNA was selected with Dynabeads (Dynal Biotech). First-strand cDNA synthesis was primed with random hexamers (SuperScript III; Invitrogen). VLRs were PCR-amplified from lymphocyte cDNA or genomic DNA extracted from whole larvae or livers of adults, using primers that anneal near the first and last residues of LRRNT and LRRCT, respectively: VLRA.F 5-aaaaaaggccaccggggccAAAACGTGTGAAACGGTC (SEQ ID NO.: 9); VLRA.R 5-aaaaaaggccccagaggccccCTC-CACGAATGGGCACT (SEQ ID NO.: 10); VLRB.F aaaaaaggccaccggggccGCATGTCCCTCGCAGTGT (SEQ ID NO.: 11); and VLRB. R aaaaaaggccccagaggc-cccTGGGCATTTCGAGGGGCT (SEQ ID NO.: 12). These primers carry overhangs with unique SfiI sites (italicized). The SfiI-digested library and pYSD2 were ligated at an insert-to vector molar ratio of 5:1 overnight at 16° C. Then 10 ng of the ligated library was amplified in a 10-L reaction of TempliPhi 100 (GE Healthcare) for 4 h at 30° C. The reaction volume was increased to 400 L, including 100 pmol of primers HR.F 5-AAACGGAATTAACCCTCCACT (SEQ ID NO.: 13) and HR.R 5-AAACCGGCGTAGAGGATGCA (SEQ ID NO.: 14) (FIG. 4A), 16 L of dNTPs (25 mM; Roche), 8 L of BSA (10 mg/mL; New England Biolabs), 4 L of pyrophosphatase (100 units/mL; New England Biolabs), buffer, and 8 L of phi29 DNA polymerase (10 units/L; New England Biolabs). After 16 h at 30° C., 100 pmol of primers HR.F and HR.R were again added, along with 6 L of PmeI restriction enzyme (10 units/L; New England Biolabs). The reaction was incubated for 3 h at 30° C., for 1 h at 37° C., and then for 20 min at 65° C. The amplified DNA was purified (QIAquick PCR; Qiagen), yielding 10-20 g of the linearized library.

The libraries were used to transform yeast strain BJ5464 (ATCC 208288) using LiAc (DSY Yeast Transformation Kit; Dualsystems Biotech), yielding $5-50 \times 10^6$ individual clones, which is the typical library size dictated by yeast transformation efficiency (15). Transformed libraries and individual clones were cultured at 30° C. in YPD (2% Bacto Peptone, 1% Bacto Yeast Extract, and 2% glucose; BD Biosciences) with 100 g/mL of G418 (American Bioanalytical). The YPD agar plates included 300 g/mL of G418. For YSD, cultures in YPD supplemented with 100 g/mL of G418 were grown to OD600=2-4, diluted to OD600=0.1 in YPG (2% Bacto Peptone, 1% Bacto Yeast Extract, 0.1% glucose, and 2% galactose) and cultured to OD600=2-4.

Sequence Analysis: Sequences of individual clones in pYSD2 were determined from plasmids transformed into E. coli. MEGA 3.1 was used for nucleotide sequence analysis and generation of the neighbor-joining tree (23). Corresponding VLRA genomic cassettes (GenBank accession numbers EF528588-EF529434) were tiled to the transcripts as reported previously (30).

pSCS Vector for Yeast-Secreted VLR: The pSCS plasmid was constructed on the backbone of pYSD2. The yeast 2 origin of replication, a BspHI fragment from pESC-TRP (Stratagene), was cloned into the PciI site instead of CEN6/ARS4. In pSCS2-a (5.1 kb), the AMF leader and prepro from pRS314-alphapp D1.3-cmyc (from K.D.W.) replaced the Flo1p leader. Downstream from the SfiI cloning sites, the following tags were added: FLAG, 6-His, c-myc, and Avi, the 14-residue synthetic substrate of E. coli BirA biotin ligase (29). For in vivo biotinylation of secreted VLR, BirA was coexpressed with the VLR in vector pSCS3-a (7 kb). BirA was PCR amplified from E. coli DNA, and the BirA 5' end was fused to the AGA2 leader from pCTCON2. At the 3' end, BirA was fused to the golgi-localization KEX2 C terminus (positions 2297-2614 in gb M22870.1), amplified from yeast DNA, essentially as described previously (30). In pSCS3-a, the ADH1 terminator, MCS1, and GAL10/GAL1 dual promoter were amplified from pESC-TRP, replacing the GAL1 promoter in pSCS2-a. The chimeric AGA2-BirA-KEX2 was cloned into EcoRI+SacI in MCS1 under the GAL10 promoter and VLR expression was under the GAL1 promoter.

Yeast strain YVH10, transformed using the YEAST-1 transformation kit (Sigma), was used for VLR secretion. Colonies were cultured for 72 h at 30° C. in BYPDG, pH 6.7 (2% Bacto Peptone, 1% Bacto Yeast Extract, 44 mM Na2HPO4~7H2O, 56 mM NaH2PO4, 2% glucose, 2% galactose, and 100 g/mL G418), with 2% galactose added daily. The BYPDG also included 0.05% of detergent, either Tween 20 (USB) or n-octyl-J3-D-glucopyranoside (Sigma). For Ni-NTA agarose (Qiagen) purification, 5 N NaOH was added to reach pH 8, and NaCl to 0.3 M. Typical IMAC yields of VLR expressed in pSCS2-a were 10-50 mg/L, and 2-10 mg/L biotinylated VLR from pSCS3-a.

YSD Library Screening: Libraries were enriched for antigen-binding clones by 1 or 2 rounds of MACS using 0.5-1 µM biotinylated antigen, antibiotin microbeads, and a MiniMACS separation unit (Miltenyi). The wash buffer consisted of PBS, 0.5% BSA, 2 mM EDTA, and 0.1% Tween 20. Propagated MACS output cells were enriched by 1-3 rounds of FACS, labeled with 2-500 nM biotinylated antigen and 100 ng/mL of rat anti-HA (clone 3F10; Roche). The cells were rotated for 25 min at room temperature and then placed on ice for 5 min. Cells were washed 3 times and incubated with 1:200 dilutions of Alexa Fluor-488 donkey anti-rat IgG (Invitrogen) and SAPE (Invitrogen) for 20 min on ice. Cells were then washed 3 times with PBS and 0.1% BSA, and then sorted using a FACSort equipped with a cell concentration module (BD Biosciences).

Figure 6A:
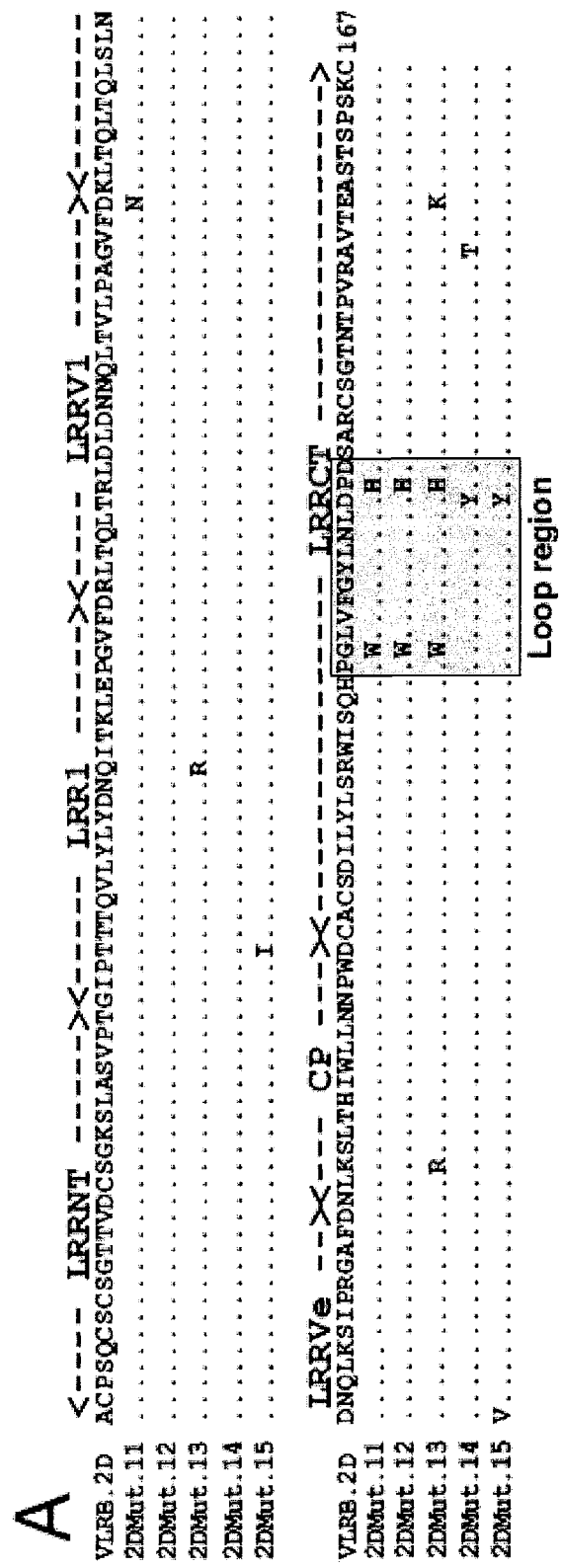
FIG. 6 shows the affinity maturation in vitro of VLRB antibodies. (A) The sequence of VLRB.HEL.2D (SEQ ID NO: 34) aligned with 5 mutant clones selected after in vitro random mutagenesis (2DMut.11 SEQ ID NO. 35; 2DMut.12 SEQ ID NO: 36; 2DMut.13 SEQ ID NO: 37; 2DMut.14 SEQ ID NO: 38; 2DMut.15 SEQ ID NO: 39). Dots indicate identity to the top sequence. The LRRCT hypervariable loop region is shaded yellow. (B) Sorting LRRCT loop-swapped mutants. The second MACS output was labeled with 1 nM HEL, and a representative mutant clone VLRB.CTMut.5 was stained with HEL as indicated. (C) The sequence of VLRB- .HEL.1 (SEQ ID NO: 40) aligned with mutant clone VLR-B.CTMut.5 (SEQ ID NO.: 25). The swapped LRRCT region is delineated by PCR primers (forward, reverse). (D) SPR sensogram of the interaction between immobilized NeutrAvidin-biotin-VLRB.CTMut.5 with 2-fold HEL serial dilutions (7.66-0.00299 nM). $K_D$=119 pM. RU, resonance units.
Figure 6B:
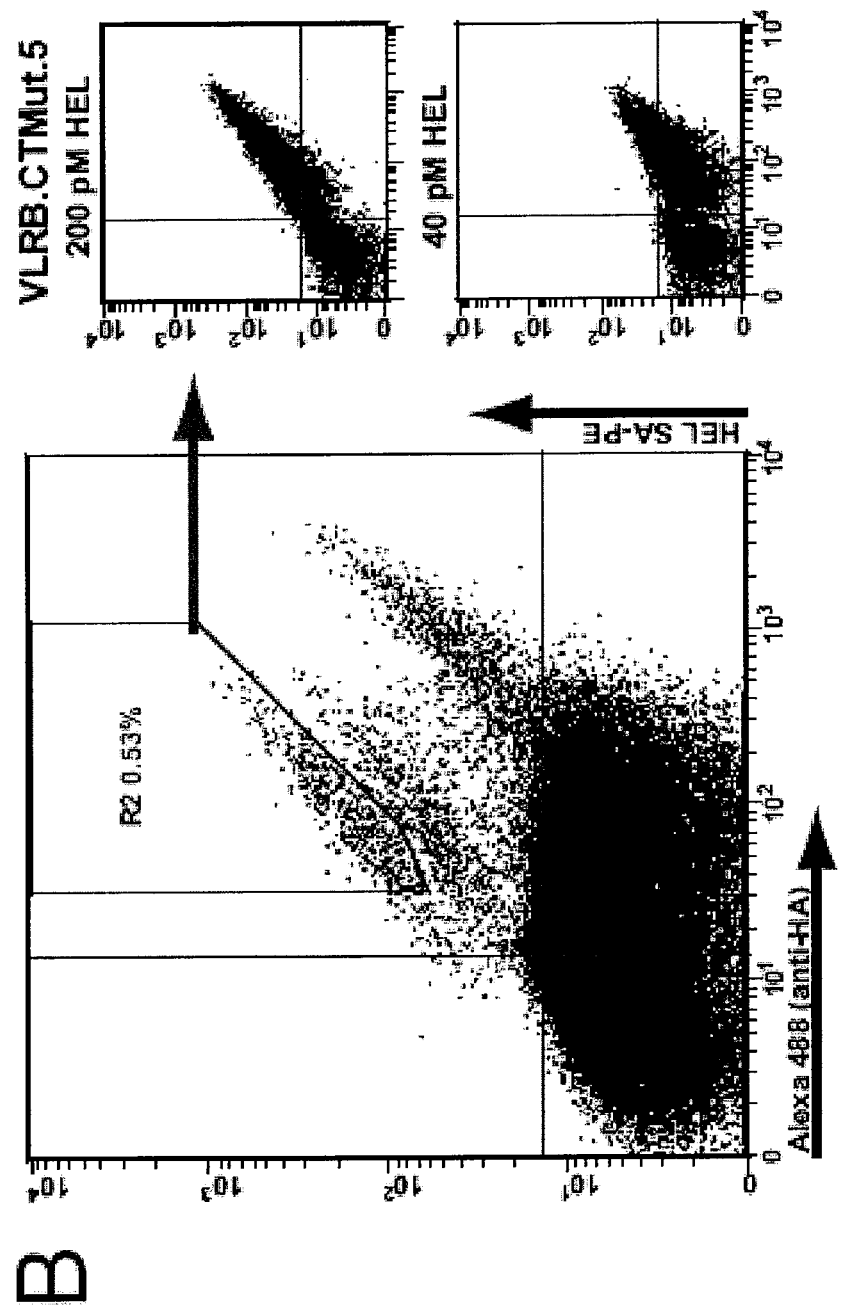
Figure 6C:
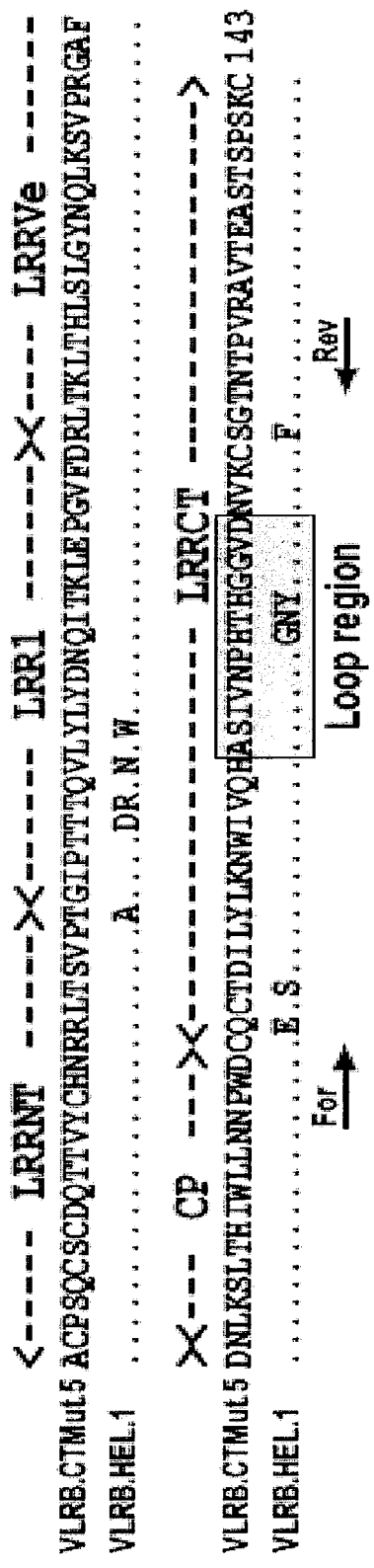

VLRB In Vitro Mutagenesis: The VLRB.HEL.2D amplicon at 15 ng/µL was diluted 7,000-fold, and 1 µL was used as a template for PCR using a GeneMorph II kit (Stratagene). Average residue substitutions were determined from 16 mutagenized clones. To swap the LRRCT loop region, the VLRB 5' region, from LRRNT to CP, was amplified with primers LRRNTS.F 5-GCATGTCCCTCGCA (SEQ ID NO.: 15) and CP.R 5-CAGTCCCAGGGGTT (SEQ ID NO.: 16). The hypervariable loop region (112-148 bp) was amplified from pooled VLRB amplicons using primers CP.F 5-AAC-CCCTGGGACTG (SEQ ID NO.: 17) and 3LRRCT.R 5-GGACGGGGGTATTG (SEQ ID NO.: 18) (FIG. 6C). The resulting amplicons were assembled by overlap extension PCR using primers LRRNT.F 5-GCATGTCCCTCGCAGT-GTTC (SEQ ID NO.: 19) and LRRCT.R 5-TGGGCATTTC-GAGGGGCTAGTGCTGGCCTCGGTGACCG-CACGGACGGGGGTAT TG (SEQ ID NO.: 20). The resulting amplicons were amplified with primers VLRB.F+ VLRB.R and cloned in pYSD2.

Equilibrium Dissociation Constants: YSD antigen titrations of VLRs were preformed as described previously (18). Triplicate aliquots of $10^5$ yeast cells were labeled with antigen concentrations ranging from 10-fold above to 10-fold below the dissociation constant. Equilibrium dissociation constants were obtained by plotting total mean fluorescence (PE channel) against antigen concentration, using nonlinear least squares to fit the curve. A BIAcore T100 biosensor (GE Healthcare) was used for affinity analysis of VLR-ligand interactions. Secreted biotinylated VLRs were desalted (Hi-Trap column; GE Healthcare) and captured onto NeutrAvidin (Pierce) amine-coupled to a CM5 chip (GE Healthcare). Analytes were injected at 40 µL/min in FIBS-EP buffer (GE Healthcare). Immobilized VLRs were regenerated by injection of 10 mM glycine-HCl (pH 2) and 0.005% Tween at 10 µL/min for 20 s. SPR data were fitted to a predefined 1:1 kinetic binding model to obtain the on and off rates.

For ITC measurements, VLRs were cloned in pT7-7 (Novagen), and expressed as inclusion bodies in *Escherichia coli* BL21-CodonPlus(DE3)-RIL (Stratagene). Induced bacteria were sonicated in 50 mM Tris-HCl (pH 8), 0.1 M NaCl, and 2 mM EDTA. Inclusion bodies were washed with 50 mM Tris-HCl (pH 8), 0.1 M NaCl, and 0.5% (vol/vol) Triton X-100, then solubilized in 8 M urea and 100 mM Tris-HCl (pH 8.5). Proteins were diluted to 10 mg/L with 0.8 M arginine, 100 mM Tris-HCl (pH 8.5), 2 mM EDTA, 3 mM reduced glutathione, and 0.3 mM oxidized glutathione. After 3 days at 4° C., folding mixtures were concentrated, dialyzed against 20 mM Tris-HCl (pH 8.5), and applied to a MonoQ column (GE Healthcare). A Superdex 75 HR column (GE Healthcare) was used for purification. ITC measurements were carried out at 25° C. in a MicroCal VP-ITC unit (GE Healthcare). Purified VLRs and HEL were dialyzed against 5 mM phosphate (pH 7.2), 136 mM NaCl, and 4 mM KCl. Typically, 3-µL aliquots of 0.638-3.95 mM HEL were injected from a 250-µL syringe rotating at 290 rpm into the sample cell containing 1.37 mL of 0.025-0.060 mM VLR solution. Corrections for buffer dilution were subtracted from the binding data. $K_D$ values were calculated by nonlinear least squares fits of ITC data for a single-site binding model. Data were acquired and analyzed using ORIGIN software.

Results and Discussion

To test the novel vector, a VLR library in pYSD2 of $8\times10^6$ individual colons was generated from HEL-immunized larvae. The library was screened using 500 nM HEL, and among several unique clones VLRB.2D was identified. (FIGS. 2B and C).

Figure 2C:
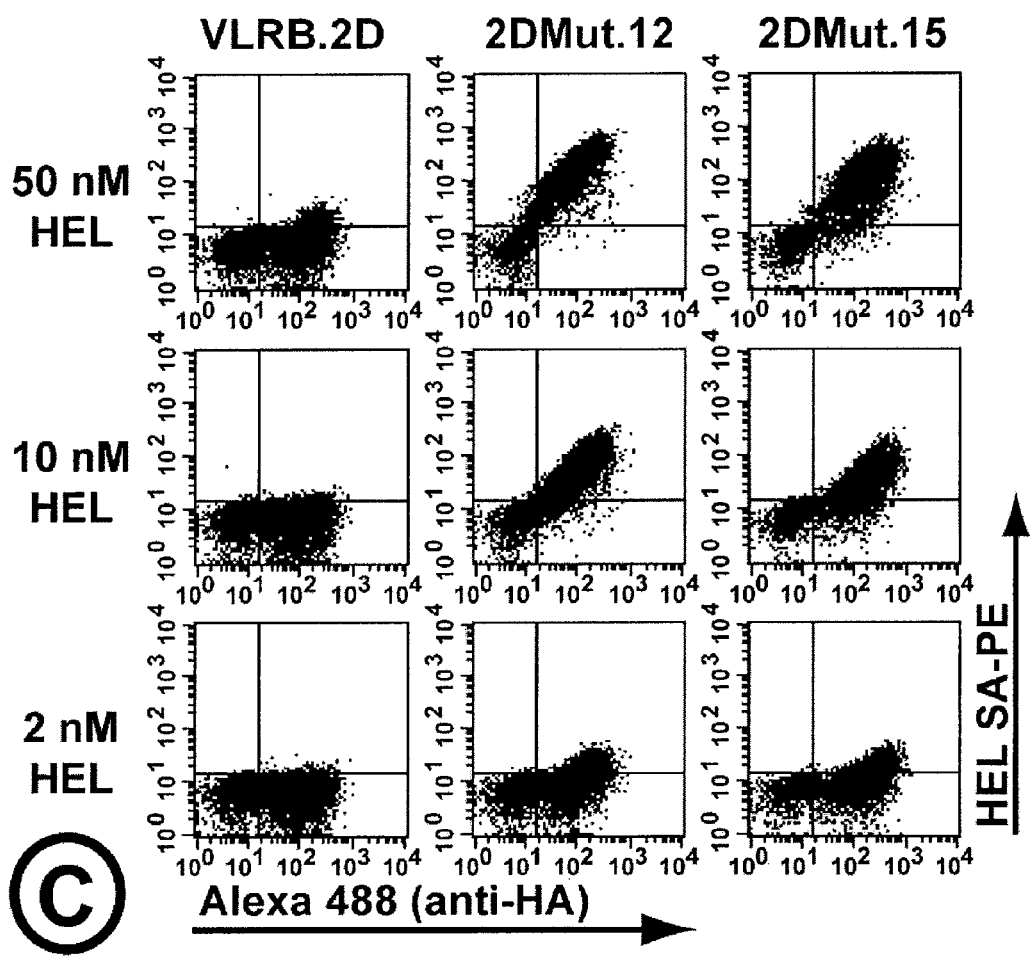
FIG. 2. A. Plasma VLR response of adult lamprey repeatedly immunized with hen egg lysozyme (HEL) and sampled at the indicated time points. ELISA assay with a mAb against the conserved VLR stalk used for detection. B. Yeast surface display of HEL-binder clone VLRB.2D. FACS analysis using 100 nM biotinylated HEL and R-phycoerythrin-conjugated streptavidin (SA-PE), and rat anti-HA mAb to detect the VLR C-terminal hemagglutinin tag and anti-rat Alexa 488 labeled Abs. C. VLRB.2D and two of its in vitro mutagenized versions, 2DMut.12 and 2DMut.15, labeled with HEL at the indicated concentrations. D. Alignment of VLRB.2D (SEQ ID No: 22) and six clones selected following one round of mutagenesis. Identical residues are marked by dots (2dMutt.1 SEQ ID NO: 28; 2DMUt.11 SEQ ID NO: 29; 2DMut.12 SEQ ID NO.: 30; 2DMut.13 SEQ ID NO: 31; 2DMut. 14 SEQ ID No 32; 2dMut. 15 SEQ ID NO: 33). The predicted hypervariable hairpin loop region in LRRCT is shaded yellow (Rogozin et al., 2007). E. An anti-RPE VLR clone labeled with the indicated concentrations R-phycoerythrin (R-PE).
Figure 3:
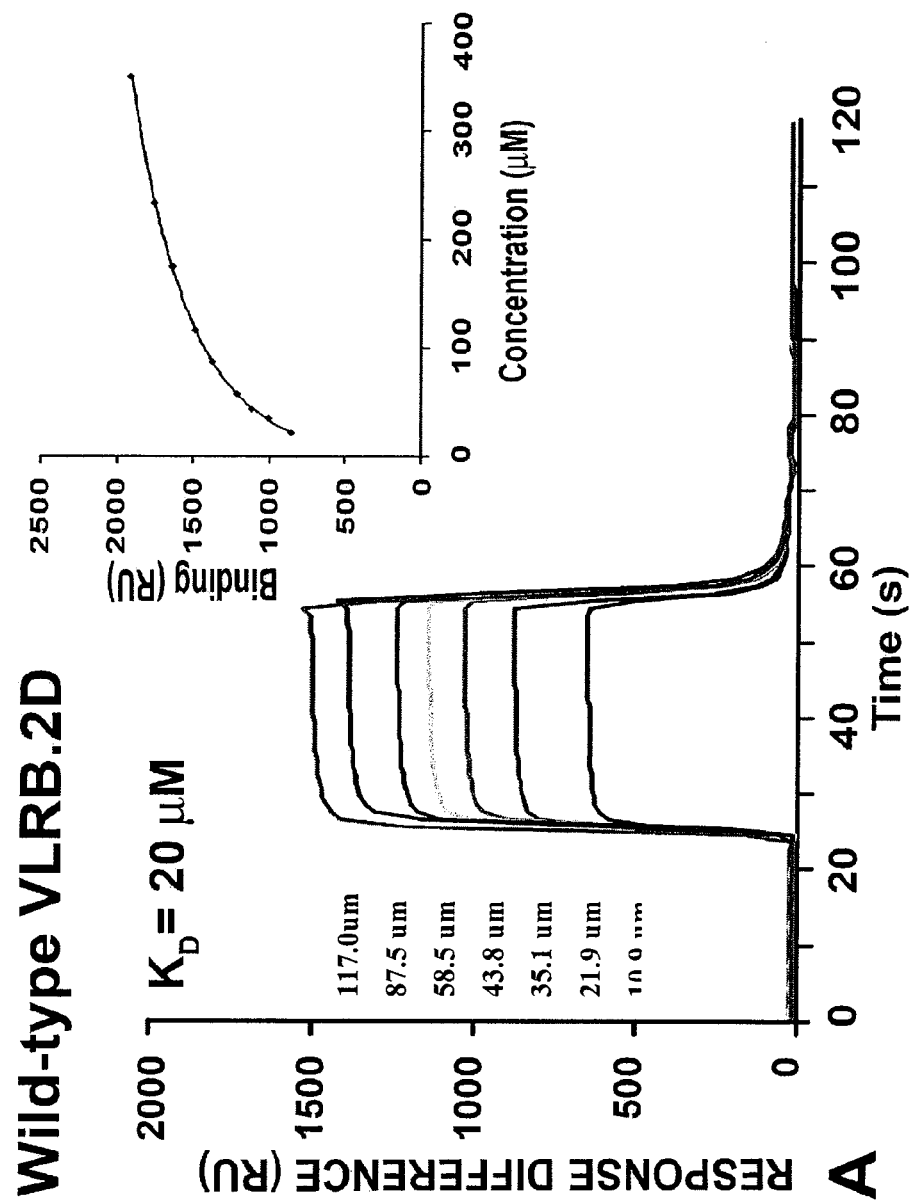
FIG. 3 shows equilibrium binding of wild-type and mutant VLRB.2D to HEL. SPR sensograms for the interaction of (A) wild-type VLRB.2D (117.0, 87.5, 58.5, 43.8, 35.1, 21.9, 10.9 µM) and (B) mutant 2DMut.12 (30.8, 24.5, 15.4, 7.5, 3.8, 1.9, 1.0 µM) with immobilized HEL after correction for non-specific binding. Inset plots show non-linear steady-state affinity analysis of the equilibrium binding data.
Figure 3B:
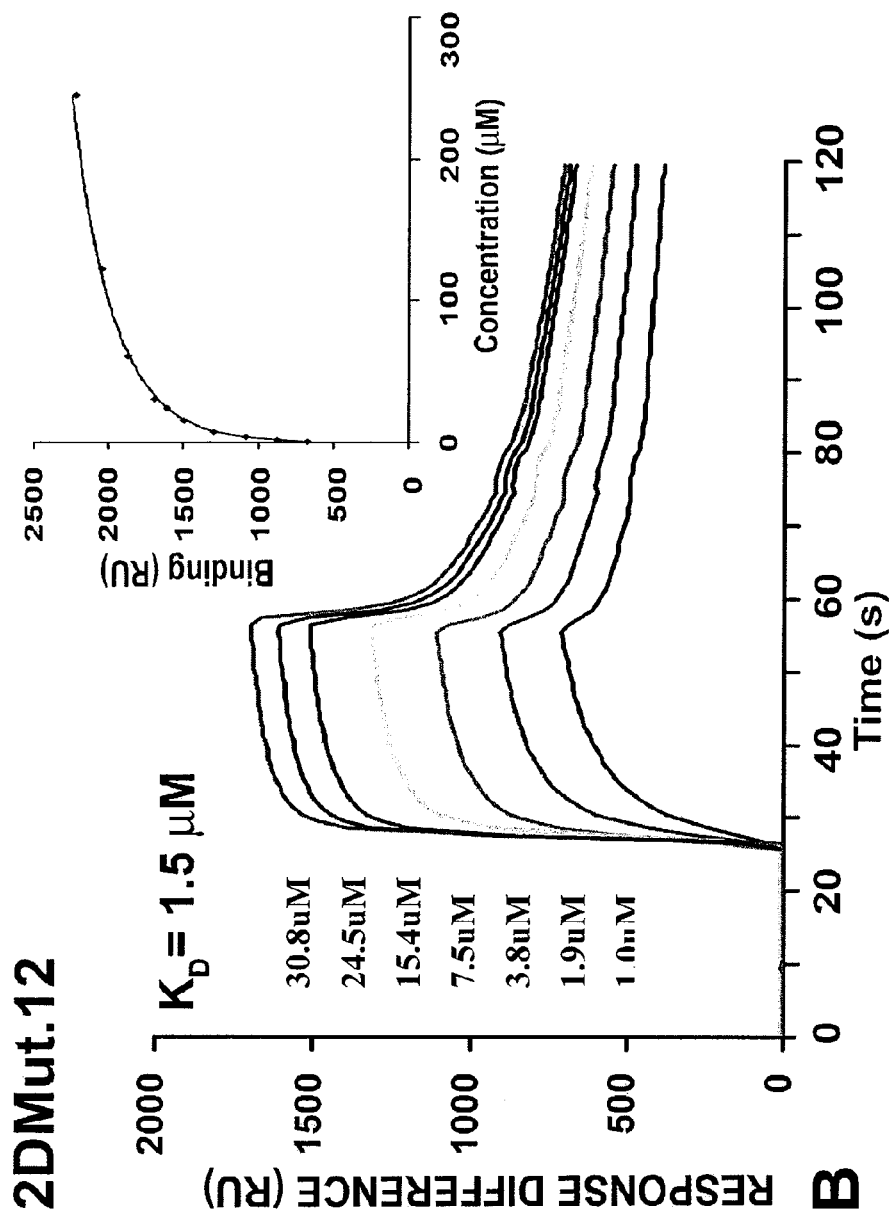

The novel vector was used to determine whether YSD could be used to select affinity matured mutants of the HEL-binding clone VLRB.2D ($K_D$=20 uM by SPR). In vitro random mutagenesis was performed on the wild-type VLRB.2D using the GeneMorph II kit (Stratagene). Sequences of 16 clones of the mutagenized amplicon revealed an average of 2.8 amino acid substitutions along the 168-residue diversity region. Then a YSD library of $2\times10^6$ individual clones was constructed and selected high affinity HEL binders, with one round of sorting at 50 nM HEL and then one at 10 nM HEL. Of six unique sequence clones, five showed increased affinity for HEL compared with the original VLRB.2D clone (FIG. 2C). Interestingly, all five clones had one or two substitutions in the LRRCT (FIG. 2D), indicating a possible role for this module in antigen recognition. As measured by SPR, one of these clones (2DMut.12) bound HEL with $K_D$=1.5 uM (FIG. 3B), corresponding to a 13-fold improvement over wild-type. Hence, even one round of in vitro mutagenesis of VLRs can clearly enhance ligand affinity. Based on these results, it is highly likely that additional rounds of mutagenesis, using 2DMut.12 as the starting template, will yield HEL binders with $K_D$s in the nanomolar range.

Figure 2E:
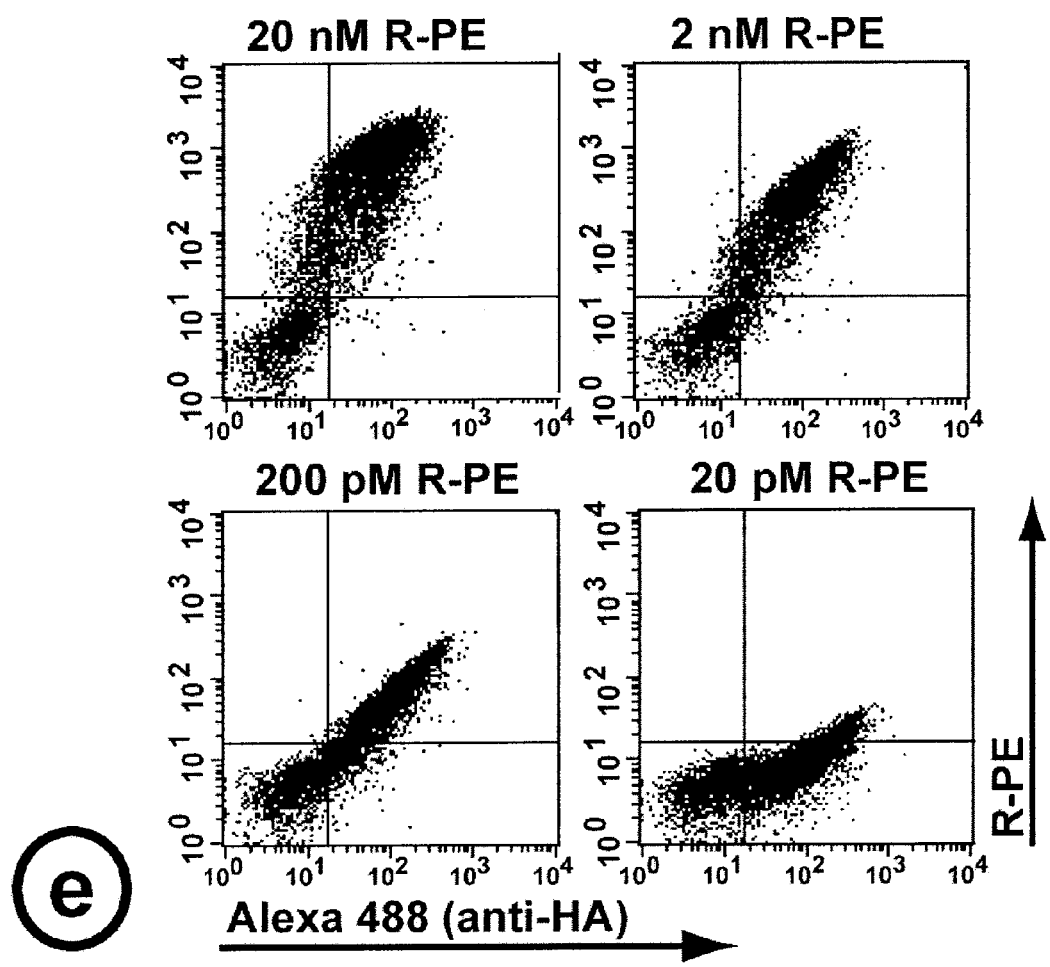

Next it was questioned whether VLRs recognizing ligands other than HEL could be isolated by YSD. Of special interest would be a ligand against which the lamprey had not been previously immunized, since a positive result would obviate the need for immunization. Accordingly, a VLR YSD library was generated of $3\times10^7$ clones from an HEL-immunized adult lamprey, and this library screened for binding to R-phycoerythrin (R-PE) as an arbitrary ligand. R-PE is one of the components of the light-harvesting antenna system in algae, whose crystal structure has been resolved (39, 33). Remarkably, a high affinity clone was isolated using 20 nM R-PE for labeling, which can efficiently bind as low as 200 pM R-PE (FIG. 2E). Since photosynthetic algae are not known as pathogens, it was estimated that R-PE binders may originate from the naïve VLR repertoire of this animal. VLRs from immunized or naïve lamprey can thus be a rich source for moderate to high affinity antigen binders, which can be subjected to in vitro affinity maturation in order to produce highly valuable biotechnology products.

Thus, it is now possible to produce recombinant VLRs that can bind a broad array of chemically and structurally diverse ligands with high affinity and specificity. Lamprey can be immunized against most, if not all, antigens, following biweekly or monthly intraperitoneal challenges for 8-16 weeks (FIGS. 2A and 5). It is also conceivable, as suggested by our isolation of R-PE binders (FIG. 2E), that the naïve VLR repertoire is sufficiently diverse to include at least micromolar affinity binders for most ligands. For example, single-chain antibody fragments with $K_D$s in the low micromolar or high nanomolar range, affinities comparable to those obtained by hybridoma techniques, can be enriched for most antigens by phage display or YSD (18, 41).

Immune Response to Soluble Antigens: To study the role of VLRB in lamprey immunity, an adult and larvae was immunized to hen egg lysozyme (HEL), a soluble monovalent antigen commonly used to study the antigen-binding properties of jawed vertebrate Ig-based antibodies (13, 14). For strong and persistent stimulation of lamprey immune responses, a Freund's complete adjuvant (FCA) or heat-killed bacteria was used. Within 2-4 months, high-titer anti-HEL VLRB responses were evident in plasma from the immunized animals (FIG. 2A); larvae immunized with β-galactosidase (β-gal) responded similarly. These data provide bona fide evidence of the adaptive immune responses of lamprey against soluble antigens. Interestingly, ELISA assays with plasma VLRB from HEL-immunized lamprey showed strong reactivity only when HEL was coated onto the ELISA plate, likely due to avidity, but only weak signals when immobilized VLRB was reacted with soluble HEL. This further indicates that native multimeric VLRBs are high-avidity receptors that may have evolved to opsonize and neutralize invading pathogens akin to IgM antibodies (8, 11).

Figure 4A:
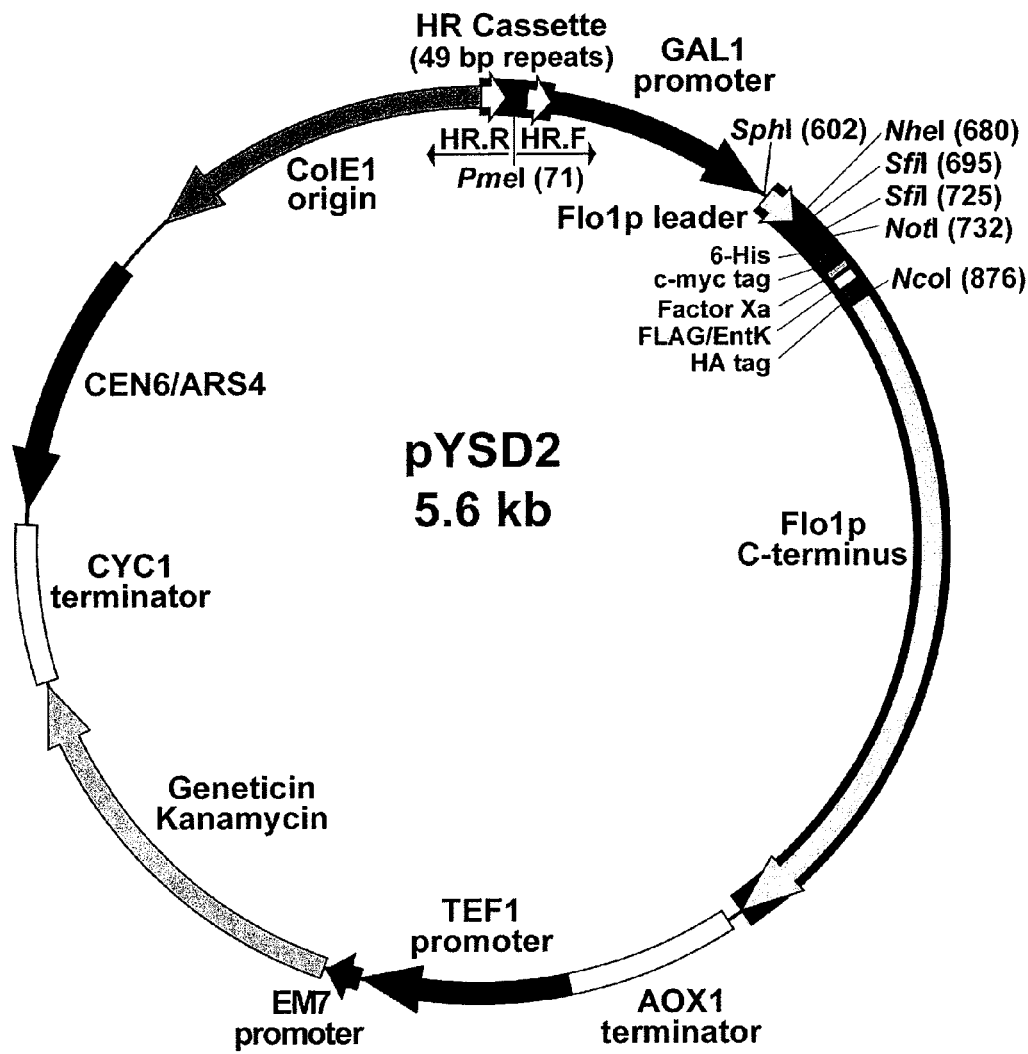
FIG. 4. A. The pYSD2 vector for yeast surface display of VLRs by N-terminal fusion to the yeast Flo1p C-terminus, using the authentic secretion leader, controlled by the tightly regulated GAL1 promoter. The vector replicates in bacteria and yeast (ColE1, CEN6/ARS4), selected by kanamycin/geneticin resistance. B. VLRs are cloned directionally between two different SfiI sites. Detection and processing tags, and location of primers indicated (YSD.F, YSD.R) (SEQ ID NO.: 23) amino acid coding (SEQ ID NO: 41). C. The homologous recombination cassette consists of two 49-bp direct repeats, separated by a linker with a PmeI restriction site for plasmid linearization. HR.F, HR.R—primers for PCR across of the whole plasmid (SEQ ID NO.: 24 and SEQ ID NO.: 55).
Figure 4B:
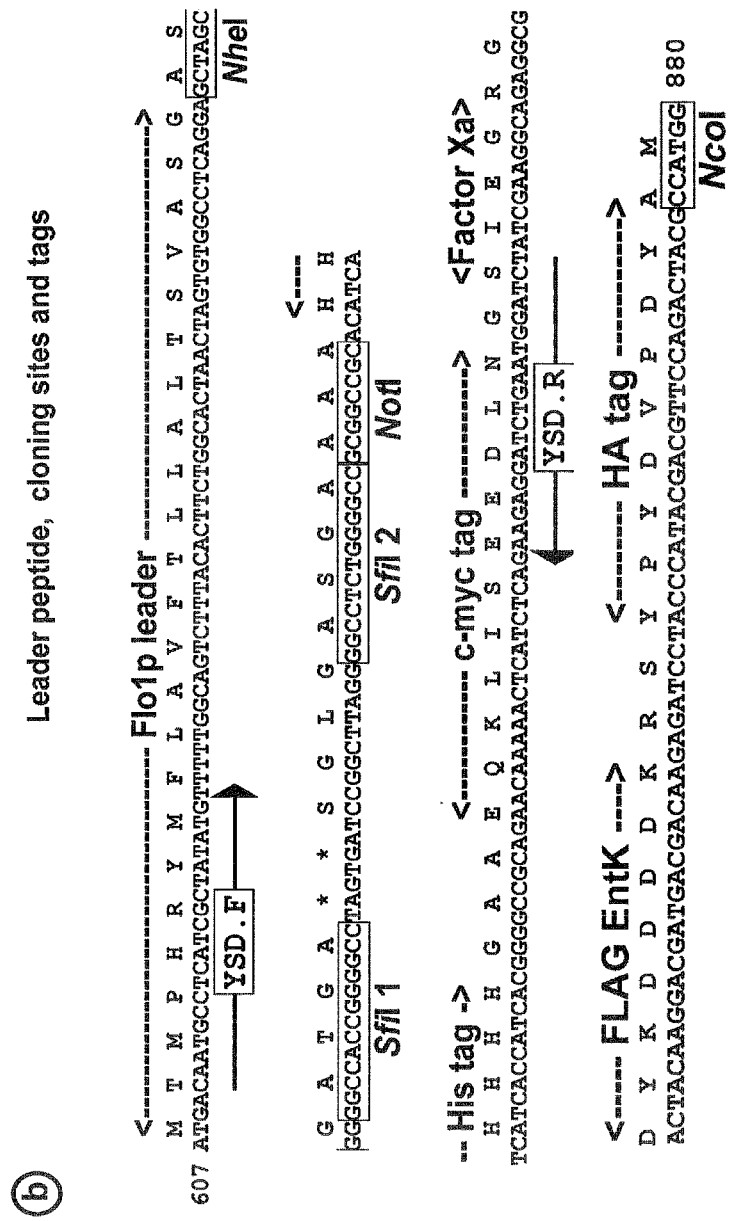
Figure 4C:
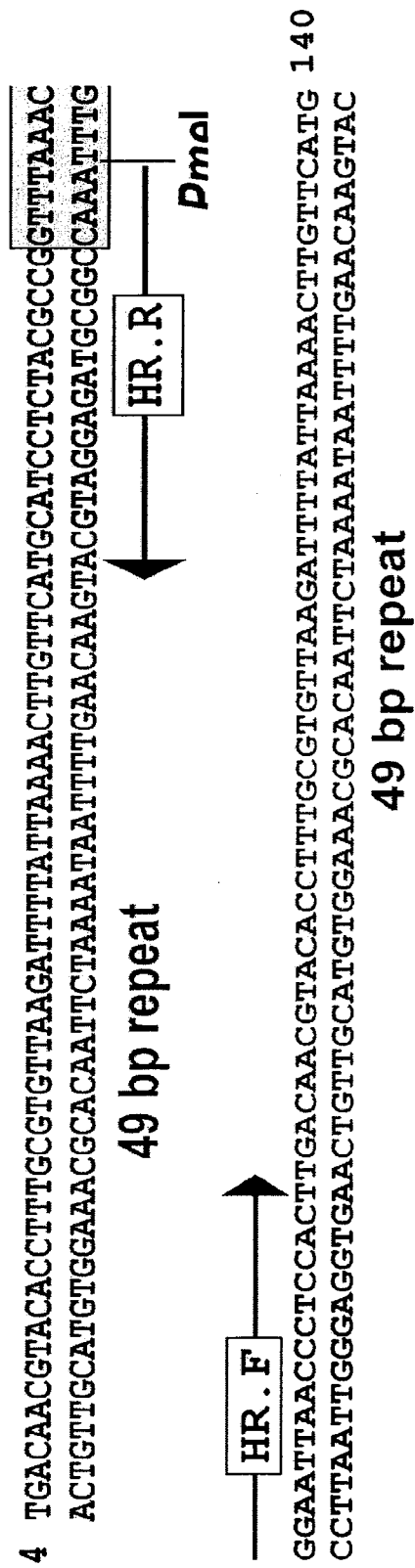
Figure 5A:
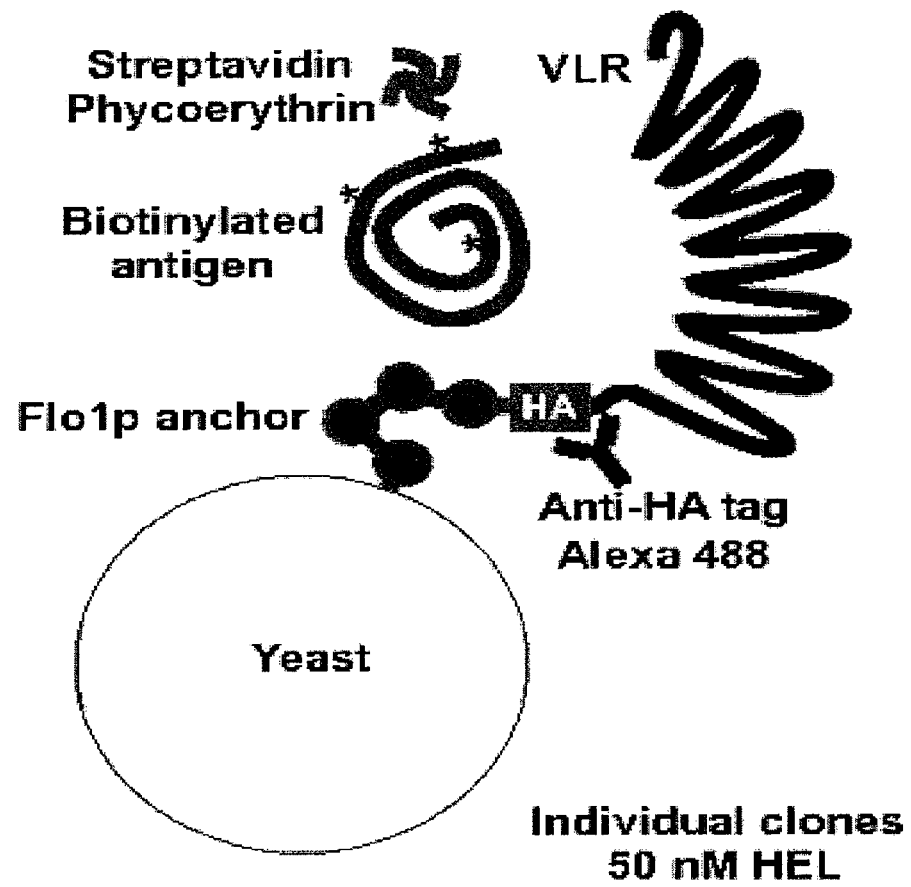
FIG. 5 shows antigen binding by VLRB antibodies. (A) Yeast surface display of VLR fused to the Flo1p anchor. The HA-tag served for VLR detection via Alexa 488-conjugated antibodies. Biotinylated ligands were detected via SAPE. (B) Enrichment of HEL-binding VLRB clones from HEL-immunized larval library. From left to right: the unsorted library, enrichment by antibiotin magnetic microbeads (with MACS), sorting of the double-positive cells in the gate, output of the first sort, output of the second sort, and the resulting clones. (C). Comparison of naïve and immune YSD libraries enriched for binders of β-gal, CTB, and B-trisaccharide. A representative clone for each antigen is shown.
Figure 5B:
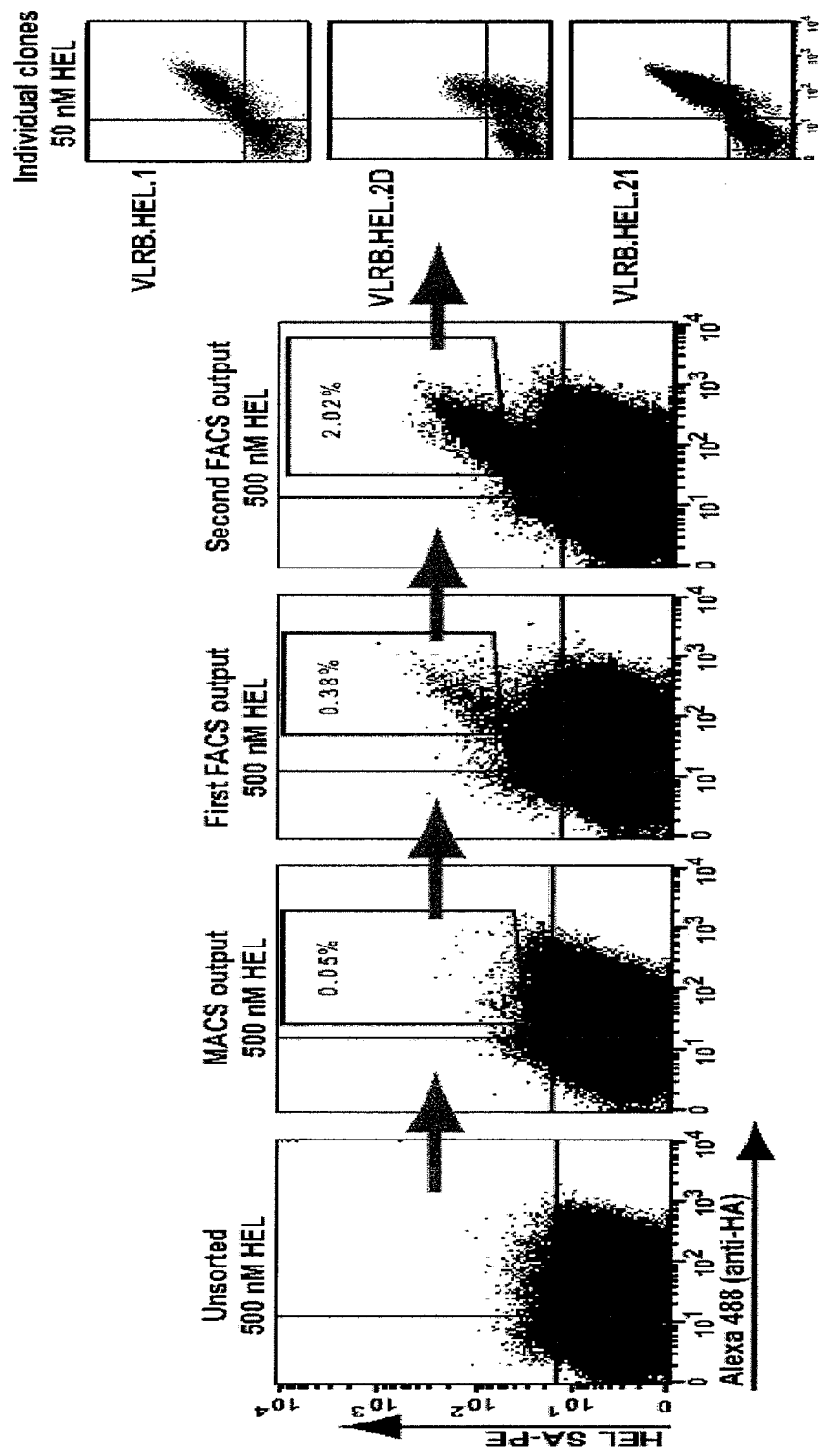

VLR Yeast Surface Display Platform: To access the lamprey VLR repertoire, the novel YSD vector of the present invention was constructed for high-sensitivity screening of large VLR libraries for specific ligand-binding clones (FIGS. 4A and 5A). The display of recombinant proteins on the surface of Saccharomyces cerevisiae was developed as a high-throughput eukaryotic platform that features oxidative protein-folding machinery, glycosylation, and an efficient secretory pathway (15). The initial experiments indicated that VLR diversity regions could be displayed C-terminally anchored on the yeast surface, with the N-termini free. In the pYSD2 vector, VLRs were fused to residues 1086-1537 from yeast flocculation protein Flo1p, which has a stalk-like structure and a C-terminal GPI cell surface anchorage motif (16) that can be used to display recombinant proteins on the surface of yeast (17). The N-terminally displayed VLRs were separated from the Flo1p anchor by a spacer that encoded a hemagglutinin (HA) tag, which served to quantify the level of surface VLR via Alexa 488-conjugated antibodies, using a fluorescence activated cell sorter (FACSort; BD Biosciences). Test ligands were biotinylated, and those bound by yeast were detected by R-phycoerythrin (RPE)-conjugated streptavidin (SAPE). The VLR-antigen complexes appear as double-positive cells in the upper-right quadrants of the dot plots (FIG. 5B).

VLR diversity regions were expressed on the surface of yeast as monomers at $2.5$-$10 \times 10^3$ copies per cell, as determined by FACS with reference beads (QuantiBRITE PE; BD Biosciences). Although the surface density of Flo1p fusions is lower than the density of $1$-$10 \times 10^4$ Aga2p fusions in the traditional YSD system (15), as shown below, libraries displaying VLR-Flo1p fusions can be efficiently screened for binders of both monovalent and polyvalent antigens. This indicates sufficient proximity of VLRs on the yeast surface to allow for cooperative binding of multivalent antigens by several VLRs, creating an avidity effect.

Monoclonal VLRB: VLRB YSD libraries were constructed from lymphocyte cDNA of HEL-immunized larvae ($8 \times 10^6$ clones) and adults ($6 \times 10^7$ clones) and screened both libraries for HEL binders (FIG. 5B). An initial enrichment by magnetic-activated cell sorting (MiniMACS; Miltenyi), with biotin-HEL and antibiotin magnetic beads, was followed by 2 successive rounds of FACS, with 5- to 7-fold enrichment of the double-positive population per round. Three clones from the larval library—VLRB.HEL.1, VLRB.HEL.2D, and VLRB.HEL.21—were selected for further analysis; all bound HEL with affinities in the range of 455-117 nM, as shown below in Table 1:

TABLE 1

VLR affinity measured by YSD antigen titration, ITC, and SPR

| Clone | YSD $K_D \pm$ SE, nM | ITC $K_D \pm$ E, nM* | SPR $K_D \pm$ SE, nM |
|---|---|---|---|
| VLRB.HEL.2D | 659 ± 42 | 427 ± 36 | 455 ± 1 |
| VLRB.2DMut.12 | 6.9 ± 0.2 | 28 ± 2 | 4.3 ± 0.13 |
| VLRB.2DMut.13 | ND | 34 ± 3 | 55.1 ± 6.8 |
| VLRB.2DMut.15 | ND | 8 ± 1 | 20.2 ± 2.1 |
| VLRB.HEL.1 | ND | 602 ± 58 | 155 ± 19 |
| VLRB.CTMut.5 | ND | ND | 0.119 ± 0.005 |
| VLRB.HEL.21 | ND | 685 ± 41 | 117 ± 18 |
| VLRB.Bg.1 | 0.03 ± 0.01 | ND | 0.0034 ± 0.0011 |
| VLRA.R2.1 | 0.42 ± 0.01 | 7 ± 1 | 0.182 ± 0.016 |
| VLRA.R2.6 | 5.6 ± 0.7 | 16 ± 2 | 1.73 ± 0.15 |
| VLRA.R3.1 | 17.6 ± 2.3 | 129 ± 12 | 10.2 ± 1.0 |
| VLRA.R4.9 | 20.1 ± 2.6 | ND | 8.38 ± 0.49 |
| VLRA.R5.1 | 0.267 ± 0.015 | 3.5 ± 0.6 | 0.124 ± 0.08 |

SE, standard error of triplicate samples;
E, uncertainties of fit;
ND, not determined.
*For all ITC measurements, molar stoichiometries (n values) ranged from 0.94 to 1.14.

The affinity of VLRs for their cognate ligands was calculated from antigen titration curves produced by 3 methods. Flow cytometry measurements of the mean fluorescence were used of surface-displayed VLR in a complex with SAPE-biotin-antigen, along with surface plasmon resonance (SPR), to measure the affinities of yeast-secreted biotinylated VLR immobilized onto NeutrAvidin-coated chips. Also affinity was measured by isothermal titration calorimetry (ITC) using VLRs that were refolded in vitro from bacterial inclusion bodies. The most convenient method was antigen titration in the YSD format, which produces dissociation constants ($K_D$) in the same range as SPR (15, 18), whereas ITC becomes progressively less precise in the low and subnanomolar range, as discussed previously (19). Thus, clones were ranked based on YSD antigen titrations, and then calculated dissociation constants for selected clones using all 3 methods as shown in Table 1.

Figure 5C:
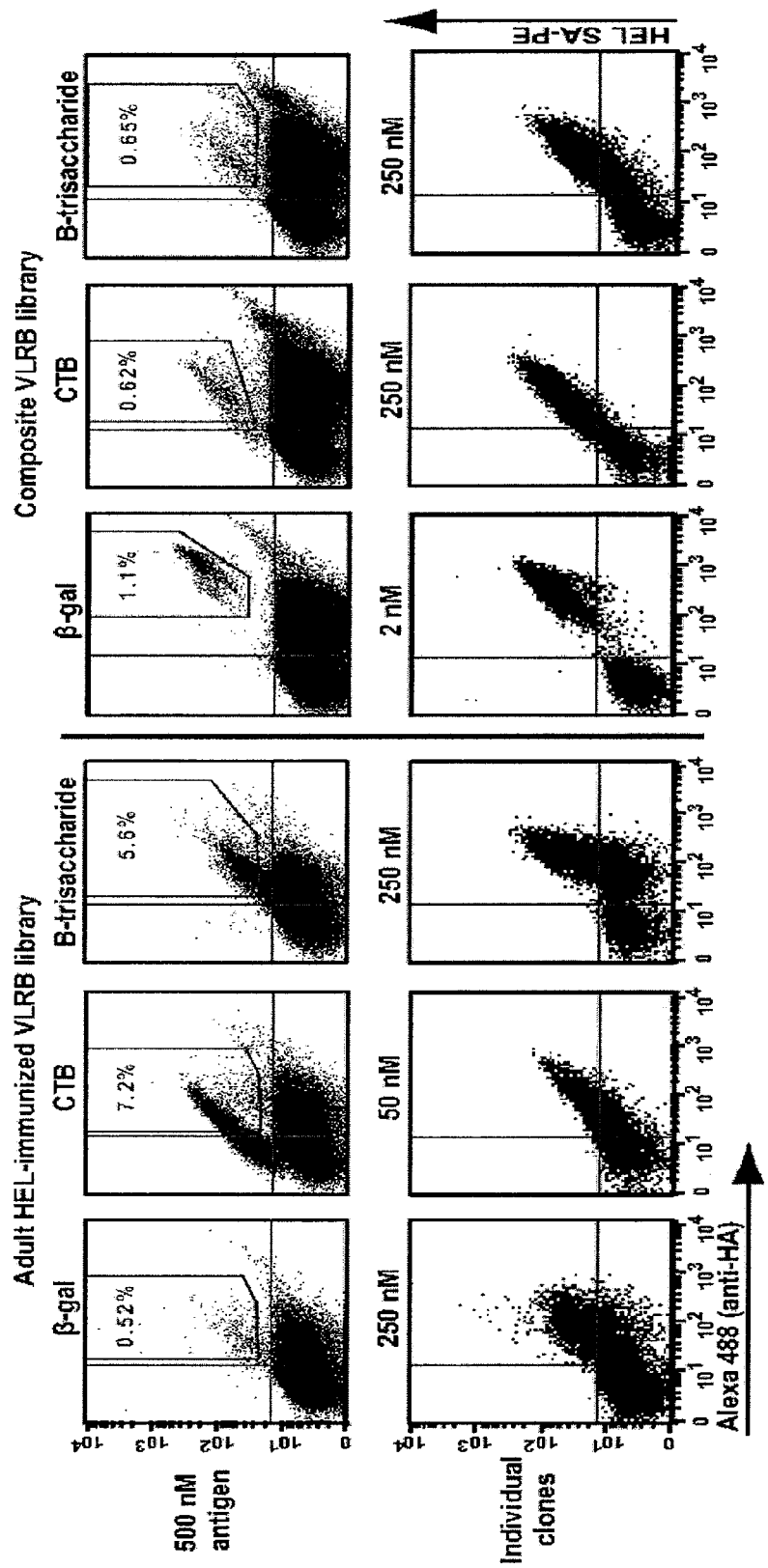

VLR affinity measured by YSD antigen titration, ITC, and SPR: To isolate binders of a broader range of antigens, a composite VLRB YSD library ($4.5 \times 10^7$ clones) was constructed from lymphocyte cDNA of approximately 100 lamprey, including animals immunized with β-gal and sheep erythrocytes, and from genomic DNA of 16 lamprey extracted from whole larvae and leukocyte-rich adult livers. The composite and HEL-immunized adult libraries were screened for binders of several multivalent antigens: β-gal (460-kDa tetramer), cholera toxin subunit B (CTB; 57-kDa pentamer), RPE (240-kDa multimer), and blood group trisaccharides A and B (≈30 kDa with 10-12 trisaccharides). The HEL-immunized adult was considered naïve with respect to all of these antigens, whereas the composite library was considered nonimmune with respect to CTB and RPE. Binders were isolated from both libraries, regardless of whether they originated from antigen-stimulated or naïve lamprey (FIG. 5C, Table 2). A high-avidity anti-β-gal VLRB was cloned from the composite library ($K_D$=3.4 pM by SPR) and an anti-RPE VLRB from the adult library ($K_D$=1.2 nM by YSD), with affinities characteristic of Ig-based single-chain antibodies isolated from immune libraries (20). Other VLRB clones bound antigens with affinities ranging from low micromolar to high nanomolar, similar to the affinities of Ig-based antibodies isolated from naïve libraries. Of the 7 trisaccharide binders that were characterized, 6 clones had 1.6- to 4.3-fold higher affinity for B-trisaccharide than for A-trisaccharide, which differs from B-trisaccharide only in the C3 saccharide, an N-acetylgalactosamine instead of galactose. To further test the ligand specificity of these carbohydrate-binding VLRB clones, antigen titration assays were conducted for trisaccharides A or B in the presence of 10-fold excess H-trisaccharide, the basic O-antigen that lacks a C3-linked saccharide. H-trisaccharide did not inhibit binding of the cognate ligands, indicating the high specificity of these clones, as shown below with results set forth in Table 2.

TABLE 2

Antigen specificity of VLRB clones

| Antigen | Number of clones | Immune library, yes/no | Affinity by YSD, nM |
|---|---|---|---|
| HEL | 4 | Yes | 400-700 |
| B-trisaccharide | 4 | Yes | 10-400 |
| A/B-trisaccharide | 1 | No | 110 |
| B-trisaccharide | 2 | No | 50, 900 |
| CTB | 3 | No | 800-10,000 |
| β-galactosidase | 1 | Yes | 0.03 |
| β-galactosidase | 1 | No | 300 |
| R-phycoerythrin | 1 | No | 1.17 |

Affinity Maturation In Vitro: For biomedical applications, the affinity of Ig-based antibodies for their ligands can be improved by in vitro mutagenesis, a process resembling in vivo affinity maturation by somatic hypermutation in jawed vertebrates (20). However, no such data are available for any member of the LRR protein superfamily. Because no high-affinity anti-HEL VLRB could be isolated directly from the prepared libraries, the feasibility of improving the affinity of VLRB.HEL.2D was considered because it was the clone with the lowest affinity among the anti-HEL VLRB clones ($K_D$=455 nM; Table 1 SPR). Error-prone PCR was used to introduce an average of 2.8 residue substitutions along the 167-codon diversity region of VLRB.HEL.2D, and constructed a mutant YSD library ($2\times10^6$ clones). The best HEL binders from this library were enriched by 2 FACS rounds, resulting in 5 unique clones (FIG. 6A) with improved affinity for HEL compared with wild-type VLRB.HEL.2D ($K_D$=55-4.3 nM; Table 1 SPR), which for clone VLRB.2DMut.12 represented a 100-fold improvement.

Figure 6D:
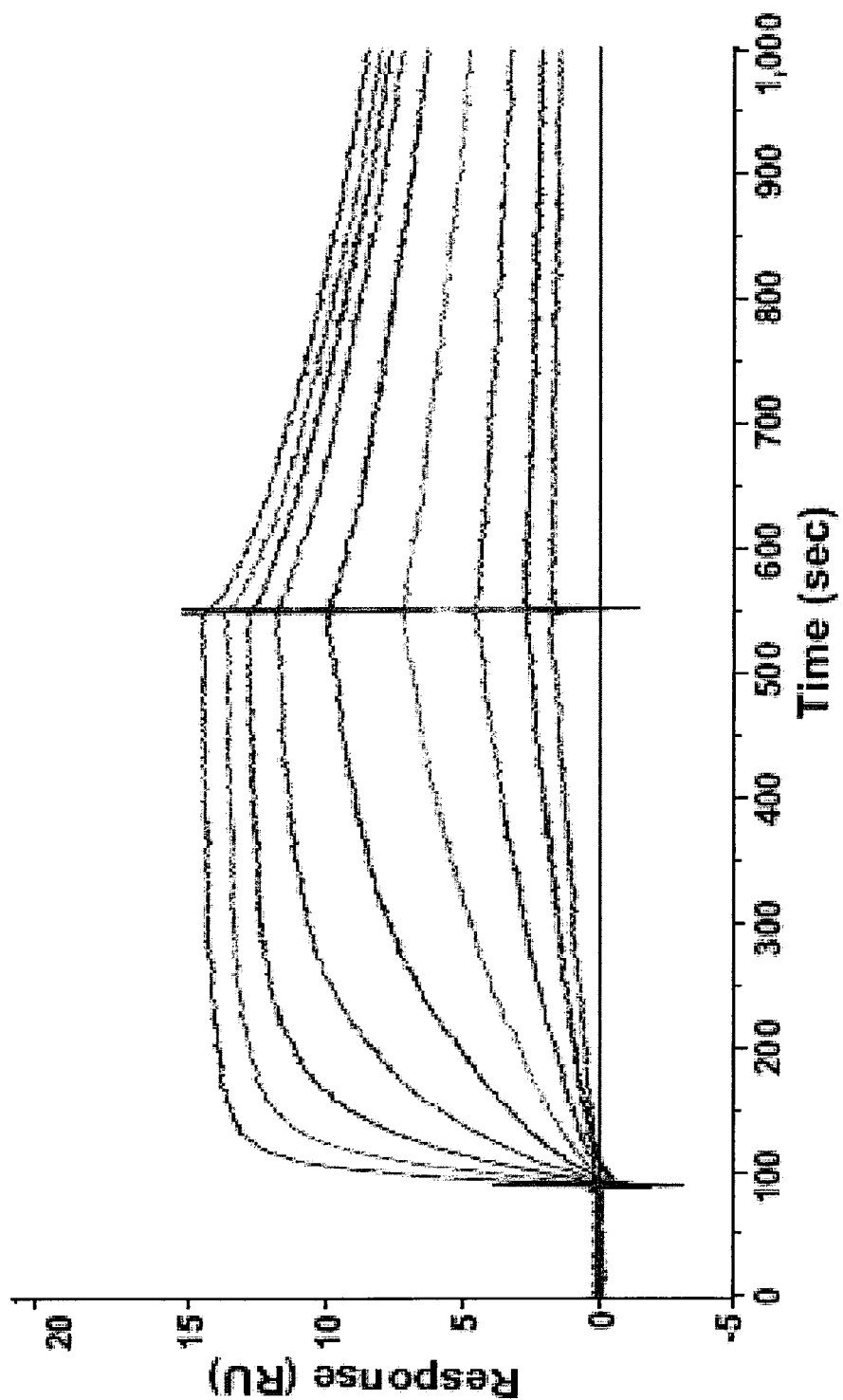

Interestingly, all of these VLRB.HEL.2D mutants had 1 or 2 substitutions in the hypervariable loop region of LRRCT, a distinctive insert following the α-helix of this LRR module that is uniquely shared by the lamprey and hagfish VLRs and the von Willebrand factor receptor GpIbα (6). Thus the hypervariable loop can contribute to antigen binding as recently validated by the crystal structure of VLRB.HEL.2D bound to HEL (21). The LRRCT loop plays a major role in this complex, where it penetrates deep into the active site cleft of the enzyme. Analysis of 517 unique VLRB sequences revealed 115 unique LRRCT loop peptides (22%); thus, it was attempted to improve affinities of VLRB clones by swapping the LRRCT loop region with corresponding PCR amplicons from a large pool of VLRB cDNA. Simultaneously, the LRRCT loop in 4 wild-type HEL-binding clones was swapped and a mutant YSD library ($2\times10^7$ clones) was constructed and then enriched it for improved binders by 2 rounds of MACS and 1 round of FACS (FIG. 6B). One of the resulting isolates was VLRB.CTMut.5, a clone derived from VLRB.HEL.1 with 6 residue substitutions in the LRRCT module, 3 of which were in the loop region (FIG. 6C). There were also 5 substitutions in the LRRNT-LRR1 region, which were derived from clone VLRB.HEL.2D, apparently by recombinational domain swapping during one of the overlap extension PCR reactions. Remarkably, the affinity of clone VLRB.CTMut.5 improved 1,300-fold, from 155 nM to 119 pM, during a single cycle of in vitro affinity maturation (FIG. 6D; Table 1 SPR), whereas 4 cycles of mutagenesis and enrichment were required for an 1,800-fold improvement of the best reported affinity-matured antifluorescein antibody (22). This indicates that a small number of residue substitutions can readily convert low-affinity monomeric VLRB into high-affinity antibodies comparable to the highest-affinity IgG.

Figure 7A:
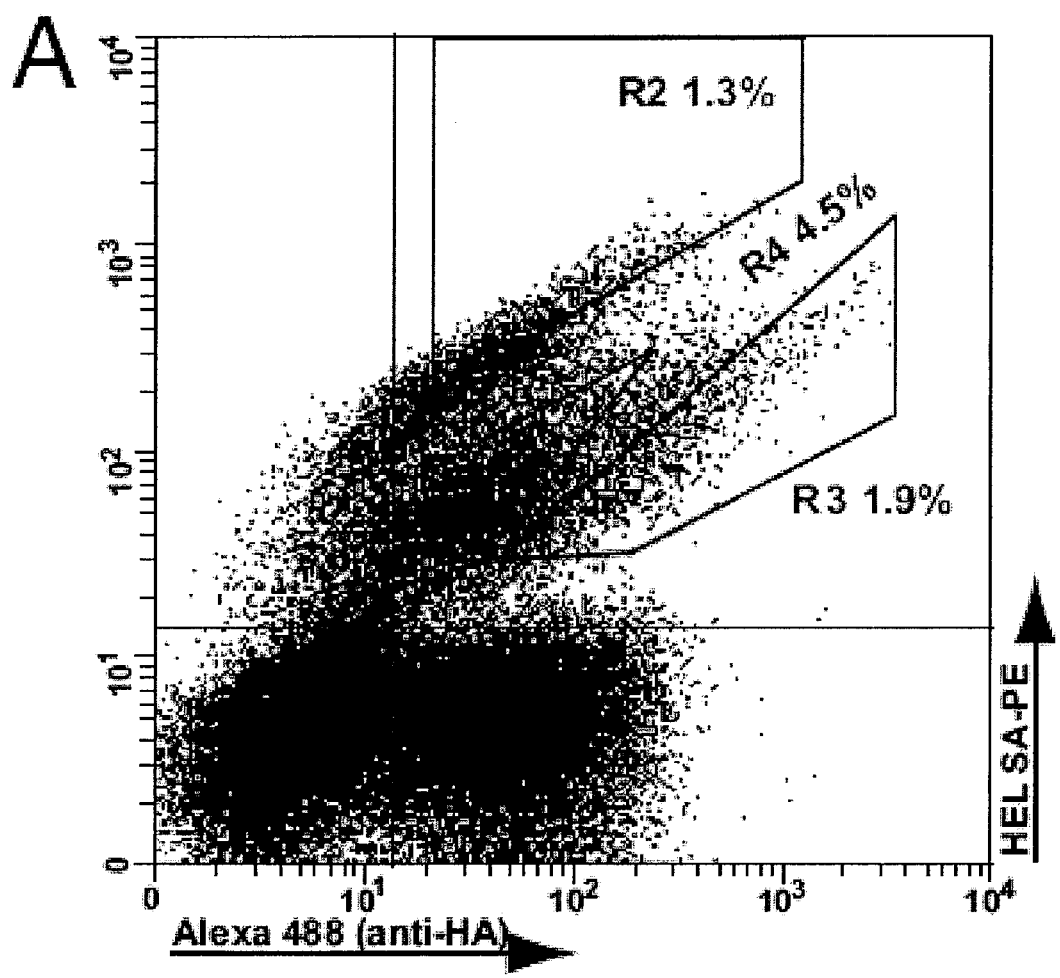
FIG. 7 show monoclonal VLRA antibodies cloned from a HEL-immunized adult lamprey. (A) Sorting anti-HEL VLRA. The second MACS output was labeled with 20 nM HEL. Clones were sorted using gates R2-R4. (B) Protein sequence alignment of 13 anti-HEL VLRA; only residues 3-246 are shown (R2.1 SEQ ID NO.: 26; R5.1 Seq ID No: 42; R5.2 SEQ ID NO: 43; R5.6 SEQ ID NO: 44; R2.6 SEQ ID NO: 45; R3.9 SEQ ID NO: 46; R4.7 SEQ ID NO 47; R4.10 SEQ ID NO: 48; R4.6 SEQ ID NO: 49; R4.8 SEQ ID NO: 50; R3.1 SEQ ID NO: 51; R4.3 SEQ ID NO: 52; R4.9 SEQ ID NO: 53; Genomic SEQ ID NO: 54). Tiled below: germline VLRA gene portions (boxes 1 and 12) and the corresponding genomic LRR cassettes (boxes 2-11; 3a and 3b alternative cassettes). Dots indicate identity to the top sequence. (C) VLRA YSD antigen titrations. Normalized mean fluorescence intensity of biotin-HEL-SAPE plotted against 2-fold serial HEL dilutions (for R2.1, 10-0.025 nM; for R2.6, 100-0.25 nM; for R4.9, 200-0.5 nM). Bars indicate SEs of triplicate samples. (D) Neighbor-joining tree of the VLRA nucleotide sequences. The corresponding $K_D$ values calculated by YSD antigen titration are given in parentheses.
Figure 7B:
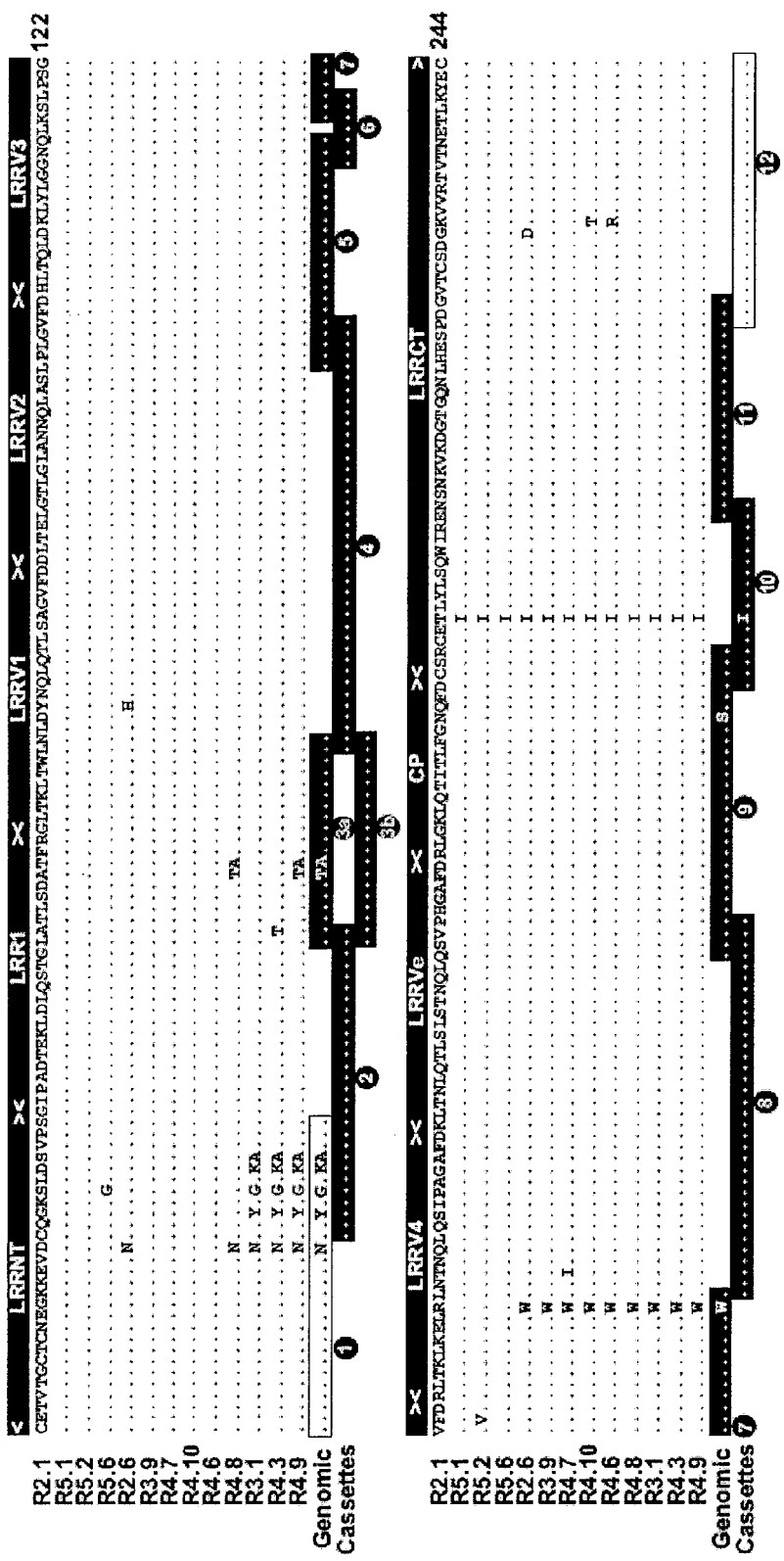

Monoclonal VLRA: The lamprey VLRA was discovered only recently (6), and no information on its antigen-binding properties is available. To access the VLRA repertoire, a VLRA YSD library was constructed from the HEL-immunized adult lamprey ($5\times10^7$ clones) and screened it for HEL binders. After 2 MACS rounds, a heterogeneous cell population stained brightly with HEL at 20 nM (FIG. 7A). Of the 50 clones analyzed, 14 had unique nucleotide sequences, 13 of which encoded unique proteins (FIG. 7B). Interestingly, these 13 VLRA clones differed at only 22 out of 732 nucleotide positions, which affected 15 variable codon positions along the 244-residue diversity region. The 1.46-fold overabundance in nonsynonymous over synonymous residue substitutions may indicate that these proteins diverged under positive selection, as further suggested by the nearly 100-fold augmentation, from 26 nM to 270 pM, in ligand-binding affinity among these VLRAs (FIGS. 7 C and D). To determine whether these mature VLRA genes were mutated in the lamprey lymphocytes or whether mutations were unintentionally introduced during YSD library construction, the sequences of YSD VLRAs were compared to PCR-amplified clones from the same lymphocyte cDNA sample. The forward PCR primer was designed based on the LRRNT of VLRA.R2.1 (5-CCAAGGCAAGAGCTTGGATTC (SEQ ID NO.: 1)), and the reverse primer was based on a unique region in the LRRCT loop (5-TTCCATCTTTTACTTTGTTGGAG (SEQ ID NO.: 2)). The distribution of variable nucleotide and residue substitutions was similar among the VLRAs selected by YSD and the unselected PCR clones, indicating that these mutations occurred in the lamprey lymphocytes.

It has been previously shown that lamprey VLRs are assembled from flanking genomic LRR-encoding cassettes via a gene conversion-like process (6). The same method was used herein to search for "footprints" of gene conversion among the variant VLRA clones by tiling the corresponding portions of germline VLRA genes and genomic LRR cassettes along the mature VLRA sequences. Several potential recombination events were evident; for example, the LRRNT of clones R4.8, R3.1, R4.3, and R4.9 was identical to the germline gene portion (FIG. 7B, box 1), whereas in all other sequences, the C-terminal half of LRRNT was identical to genomic cassette 2 at all 6 variant nucleotides. In the region corresponding to cassette 3, 4 nucleotides distinguished cassette 3a from cassette 3b; clone R4.9 was identical to cassette 3a, and clone R4.8 had 3 of the 4 unique nucleotides of cassette 3a, whereas all other clones had sequences identical to cassette 3b in this region. The simultaneous substitution of clusters of codons in these mature VLRA genes (4 in LRRNT and 2 in LRR1) is consistent with a process of gene conversion between the mature VLRA gene and 1 or more of the VLRA genomic LRR cassettes. Thus, these variant VLRAs appear to be derived from a single lymphocyte progenitor, which has a mature VLRA gene most closely to the sequence of VLRA.R4.9 in our sample. Interestingly, a phylogenetic neighbor-joining tree (23) drawn for the VLRA sequences clustered all of the subnanomolar HEL-binding clones (R2.1, R5.1, R5.2, and R5.6) based on a single substitution of the hydrophobic tryptophan at position 136 to a charged hydrophilic arginine. Alignment of these VLRA sequences based on the available VLR structures revealed that residue 136 is located at a solvent-exposed position in the LRRV4 β-strand, which is part of the concave antigen-binding surface of VLRs (12, 21).

Thus, VLRA antibodies are capable of very high-affinity interactions with antigens. For instance, the best VLRA HEL-binding clone (R5.1) had a $K_D$ of 124 pM, approaching the 100 pM affinity ceiling of Ig-based antibodies produced during mammalian immune responses (1, 24).

In conclusion, the powerful YSD platform described herein has allowed the exploration of the role of VLR in lamprey immunity by screening large libraries for specific antigen-binding VLR clones. After conversion to VLR display via the Flo1p leader and C-terminal Flo1p anchor, the optimized system allowed highly sensitive library screening for clones with binding affinities, or avidities, in the range of $10^{-6}$ to $10^{-12}$ M. The broad spectrum of antigens that VLR can specifically recognize, including monovalent and multivalent proteins and saccharides, and the binding affinities achieved, clearly attest to the remarkable diversity of the VLR repertoire in both naïve and antigen-stimulated lamprey. This suggests that the naïve VLRB repertoire includes at least low-affinity binders of many antigens. The monomeric YSD VLRB diversity regions that were assayed actually could have been derived from native high-avidity multimeric VLRB binders of these antigens. Furthermore, the analysis of anti-HEL VLRA variants and in vitro matured VLRB clones has shown that mutations can significantly enhance the affinities of these LRR-based adaptive immune receptors. Thus, the VLR system of jawless vertebrates truly behaves like the Ig-based system of jawed vertebrates, with the potential to provide an effective humoral antipathogen shield.

VLRs also hold considerable potential as natural non-Ig antibodies for various biotechnology applications (27, 28). These highly stable modular single-chain polypeptides of relatively small size (15-25 kDa) can bind a broad range of antigenic determinants with high affinity and specificity, and can be readily engineered for improved binding properties. VLR antibodies can serve in such diagnostic applications as biosensors, bioimaging, flow cytometry, immunohistochemistry, and ELISA, as well as in affinity purification. In addition, lamprey VLR can provide a rich source of reagents that recognize mammalian antigens invisible to Ig-based antibodies because of self-tolerance.

REFERENCES

The contents of all references cited herein are incorporated by reference herein for all purposes.
1. Batista F D, Neuberger M S (1998) Affinity dependence of the B cell response to antigen: A threshold, a ceiling, and the importance of off-rate. *Immunity* 8:751-759.
2. Dooley H, Stanfield R L, Brady R A, Flajnik M F, (2006) First molecular and biochemical analysis of in vivo affinity maturation in an ectothermic vertebrate. *Proc Natl Acad Sci USA* 103:1846-1851.
3. Pancer Z, et al., (2004) Somatic diversification of variable lymphocyte receptors in the agnathan sea lamprey. *Nature* 430:174-180.
4. Pancer Z, et al., (2005) Variable lymphocyte receptors in hagfish. *Proc Natl Acad Sci USA* 102:9224-9229.
5. Alder M N, et al., (2005) Diversity and function of adaptive immune receptors in a jawless vertebrate. *Science* 310:1970-1973.
6. Rogozin I B, et al., (2007) Evolution and diversification of lamprey antigen receptors: Evidence for involvement of an AID-APOBEC family cytosine deaminase. *Nat Immunol* 8:647-656.
7. Pancer Z, Cooper M D, (2006) The evolution of adaptive immunity. *Annu Rev Immunol* 24:497-518.
8. Alder M N, et al., (2008) Antibody responses of variable lymphocyte receptors in the lamprey. *Nat Immunol* 9:319-327.
9. Nagawa F, et al., (2007) Antigen-receptor genes of the agnathan lamprey are assembled by a process involving copy choice. *Nat Immunol* 8:206-213.
10. Kim H M, et al., (2007) Structural diversity of the hagfish variable lymphocyte receptors. *J Biol Chem* 282:6726-6732.
11. Herrin B R, et al., (2008) Structure and specificity of lamprey monoclonal antibodies. *Proc Natl Acad Sci USA* 105:2040-2045.
12. Han B W, Herrin B R, Cooper M D, Wilson I A, (2008) Antigen recognition by variable lymphocyte receptors. *Science* 321:1834-1837.
13. Sundberg E J, Mariuzza R A., (2003) Molecular recognition in antigen-antibody complexes. *Adv Protein Chem* 61:119-160.
14. Stanfield R L, Dooley H, Flajnik M F, Wilson I A., (2004) Crystal structure of a shark single-domain antibody V region in complex with lysozyme. *Science* 305:1770-1773.
15. Chao G, et al., (2006) Isolating and engineering human antibodies using yeast surface display. *Nat Protoc* 1:755-768.
16. Teunissen A W, Holub E, van der Hucht J, van den Berg J A, Steensma H Y., (1993) Sequence of the open reading frame of the FLO1 gene from *Saccharomyces cerevisiae*. *Yeast* 9:423-427.
17. Sato N, et al., (2002) Long anchor using Flo1 protein enhances reactivity of cell surface-displayed glucoamylase to polymer substrates. *Appl Microbiol Biotechnol* 60:469-474.
18. Feldhaus M J, et al., (2003) Flow-cytometric isolation of human antibodies from a nonimmune *Saccharomyces cerevisiae* surface display library. *Nat Biotechnol* 21:163-170.
19. Velázquez-Campoy A, Freire E., (2005) ITC in the post-genomic era? Priceless. *Biophys Chem* 115:115-124.
20. Wark K L, Hudson P J., (2006) Latest technologies for the enhancement of antibody affinity. *Adv Drug Delivery Rev* 58:657-670.
21. Velikovsky C A, et al., (2009) Structure of a lamprey variable lymphocyte receptor in complex with a protein antigen. *Nat Struc Mol Biol* 16:725-730.
22. Boder E T, Midelfort K S, Wittrup K D., (2000) Directed evolution of antibody fragments with monovalent femtomolar antigen-binding affinity. *Proc Natl Acad Sci USA* 97:10701-10705.
23. Kumar S, Tamura K, Nei M., (2004) MEGA3: Integrated software for molecular evolutionary genetics analysis and sequence alignment. *Brief Bioinform* 5:150-163.
24. Foote J, Eisen H N., (1995) Kinetic and affinity limits on antibodies produced during immune responses. *Proc Natl Acad Sci USA* 92:1254-1256.

25. Becker R S, Knight K L., (1990) Somatic diversification of immunoglobulin heavy-chain VDJ genes: Evidence for somatic gene conversion in rabbits. *Cell* 63:987-997.
26. Reynaud C A, Garcia C, Hein W R, Weill J C., (1995) Hypermutation generating the sheep immunoglobulin repertoire is an antigen-independent process. *Cell* 80:115-125.
27. Binz H K, Amstutz P, Plückthun A., (2005) Engineering novel binding proteins from nonimmunoglobulin domains. *Nat Biotechnol* 23:1257-1268.
28. Skerra A., (2007) Alternative non-antibody scaffolds for molecular recognition. *Curr Opin Biotechnol* 18:295-304.
29. Beckett D, Kovaleva E, Schatz P J (1999) A minimal peptide substrate in biotin holoenzyme synthetase-catalyzed biotinylation. *Protein Sci* 8:921-929.
30. Scholler N, Garvik B, Quarles T, Jiang S, Urban N (2006) Method for generation of in vivo biotinylated recombinant antibodies by yeast mating. *J Immunol Methods* 317:132-143.
31. Bell, J. K., Mullen, G. E., Leifer, C. A., Mazzoni, A., Davies, D. R. & Segal D M. (2003) Leucine-rich repeats and pathogen recognition in Toll-like receptors. *Trends Immunol.* 24, 528-33.
32. Breinig, F. & Schmitt, M. J. (2002) Spacer-elongated cell wall fusion proteins improve cell surface expression in the yeast *Saccharomyces cerevisiae*. *Appl. Microbiol. Biotechnol.* 58, 637-44.
33. Contreras-Martel, C., Martinez-Oyanedel, J., Bunster, M., Legrand, P., Piras, C., Vernede, X. & Fontecilla-Camps, J. C. (2001) Crystallization and 2.2 A resolution structure of R-phycoerythrin from *Gracilaria chilensis*: a case of perfect hemihedral twinning. *Acta Crystallogr. D. Biol. Crystallogr.* 57, 52-60.
34. Cornelie, S., Hoebeke, J., Schacht, A. M., Bertin, B., Vicogne, J., Capron, M. & Riveau, G. (2004) Direct evidence that toll-like receptor 9 (TLR9) functionally binds plasmid DNA by specific cytosine-phosphate-guanine motif recognition. *J. Biol. Chem.* 279, 15124-9.
35. Deng, L., Langley, R. J., Brown, P. H., Xu, G., Teng, L., Wang, Q., Gonzales, M. I., Callender, G. G., Nishimura, M. I., Topalian, S. L. & Mariuzza, R. A. (2007) Structural basis for the recognition of mutant self by a tumor-specific, MHC class II-restricted T cell receptor. *Nat. Immunol.* 8, 398-408.
36. Diebold, S. S., Kaisho, T., Hemmi, H., Akira, S. & Reis e Sousa, C. (2004) Innate antiviral responses by means of TLR7-mediated recognition of single-stranded RNA. *Science* 303, 1529-31.
37. Gai, S. A. & Wittrup, K. D. (2007) Yeast surface display for protein engineering and characterization. *Curr. Opin. Struct. Biol.* 17, 467-73.
38. Huizinga, E. G., Tsuji, S., Romijn, R. A., Schiphorst, M. E., de Groot, P. G., Sixma, J. J. & Gros, P. (2202) Structures of glycoprotein Ibalpha and its complex with von Willebrand factor A1 domain. *Science* 297, 1176-9.
39. Jiang, T., Zhang, J. & Liang, D. (1999) Structure and function of chromophores in R-Phycoerythrin at 1.9 Å resolution. *Proteins* 34, 224-31.
40. Lund, J. M., Alexopoulou, L., Sato, A., Karow, M., Adams, N. C., Gale, N. W., Iwasaki, A. & Flavell, R. A. (2004) Recognition of single-stranded RNA viruses by Toll-like receptor 7. *Proc. Natl. Acad. Sci. USA* 101, 5598-603.
41. Marks, J. D. & Bradbury, A. (2004) Selection of human antibodies from phage display libraries. *Methods Mol. Biol.* 248, 161-76.
42. Meng, G., Grabiec, A., Vallon, M., Ebe, B., Hampel, S., Bessler, W., Wagner, H. & Kirschning, C. J. (2003) Cellular recognition of tri-/di-palmitoylated peptides is independent from a domain encompassing the N-terminal seven leucine-rich repeat (LRR)/LRR-like motifs of TLR2. *J. Biol. Chem.* 278, 39822-9.
43. Pancer Z, Mariuzza R A. (2008) The oldest antibodies newly discovered. Nat Biotechnol. 26:402-3.
44. Roach, J. C., Glusman, G., Rowen, L., Kaur, A., Purcell, M. K., Smith, K. D., Hood, L. E. & Aderem, A. (2005) The Evolution of Vertebrate Toll-like Receptors. *Proc. Nat. Acad. Sci. USA* 102, 9577-82.
45. Rutz, M., Metzger, J., Gellert, T., Luppa, P., Lipford, G. B., Wagner, H. & Bauer, S. (2004) Toll-like receptor 9 binds single-stranded CpG-DNA in a sequence- and pH-dependent manner. *Eur. J. Immunol.* 34, 2541-50.
46. Sheridan, C. (2007) Pharma consolidates its grip on post-antibody landscape. *Nat. Biotechnol.* 25, 365-6.
47. Swers, J. S., Kellogg, B. A. & Wittrup, K. D. (2004) Shuffled antibody libraries created by in vivo homologous recombination and yeast surface display. *Nucleic Acids Res.* 32, e36.
48. Teunissen, A. W., Holub, E., van der Hucht, J., van den Berg, J. A. & Steensma, H. Y. (1993) Sequence of the open reading frame of the FLO1 gene from *Saccharomyces cerevisiae*. *Yeast* 9, 423-7.

That which is claimed is:

1. A Yeast Surface Display (YSD) vector for expression of a variable lymphocyte receptor (VLR) protein positioned on the surface of a yeast cell comprising:
   a nucleotide sequence encoding for the VLR protein, wherein the VLR protein was formed in response to an antigen and having affinity for the antigen;
   nucleotide sequences encoding a leader and C-terminal segment of yeast flocculation protein Flo1p, wherein the nucleotide sequence encoding for the VLR protein is positioned therebetween; and
   a homologous recombination cassette consisting of two same number of base-pair direct repeats separated by a linker wherein the linker comprises a restriction site for plasmid linearization.

2. The YSD of claim 1, further comprising the inclusion of a geneticin/kanamycin resistance gene.

3. The YSD of claim 1, wherein the two base-pair direct repeats consists of 49 base-pairs.

4. The YSD of claim 1, wherein the nucleotide sequence encoding the leader and C-terminal of yeast flocculation protein Flo1p is SEQ ID NOs.: 6 and 7, respectively.

5. The YSD of claim 1, wherein the yeast is a strain of *Saccharomyce cerevisiae*.

6. A method for providing a high-throughput platform for selection of recombinant antigen-binding VLR proteins, the system comprising:
   a) providing yeast strains of *Saccharomyce cerevisiae* and
   b) transfecting the yeast with the YSD vector of claim 1; and
   c) culturing the yeast for expression and displaying of the VLR proteins on the surface of the yeast.

7. The method of claim 6, wherein the culturing of the yeast further comprising the use of a growth medium that includes yeast peptone and sugar.

8. The method of claim 6, further comprising the inclusion of a geneticin/kanamycin resistance gene.

9. The method of claim 6, wherein the nucleotide sequence encoding the leader and C-terminal of yeast flocculation protein Flo1p is SEQ ID NOs.: 6 and 7, respectively.

10. A method of producing VLR proteins having high affinity for an antigen of choice, the method comprising:
    a) immunizing a Lamprey with the antigen and collecting plasma containing the VLR proteins formed in response to the antigen;
    b) determining nucleotide sequence encoding such VLR proteins;
    c) preparing the YSD vector of claim 1:
    d) transfecting a yeast strain;
    e) culturing the yeast for expression and displaying of the VLR proteins on the surface of the yeast; and
    f) measuring the binding affinity.

11. The method of claim 10, wherein the culturing of the yeast further comprising the use of a growth medium that includes yeast peptone and sugar.

12. The method of claim 10, further comprising the inclusion of a geneticin/kanamycin resistance gene.

13. The method of claim 10, wherein the nucleotide sequence encoding the leader and C-terminal of yeast flocculation protein Flo1p is SEQ ID NOs.: 6 and 7, respectively.

14. The method of claim 10, further comprising subjecting the nucleotide sequence encoding for the VLR protein to mutagenesis and repeat steps (c) to (f) until affinity increases for antigen of choice.

15. The YSD vector of claim 1, wherein the nucleotide sequence encoding the VLR protein comprises nucleotide sequence encoding for the stalk C-terminal of the VLP protein.

* * * * *

SEQUENCE LISTING

<160> NUMBER OF SEQ ID NOS: 62

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
ccaaggcaag agcttggatt c                                            21

<210> SEQ ID NO 2
<211> LENGTH: 23
<212> TYPE: DNA
<213> ORGANISM: Artificial Sequence
<220> FEATURE:
<223> OTHER INFORMATION: Synthetic construct -continued

<400> SEQUENCE: 2 ttccatctttt tactttgttg gag                                             23

<210> SEQ ID NO 3
<211> LENGTH: 1537
<212> TYPE: PRT
<213> ORGANISM: Saccharomyces cerevisiae

<400> SEQUENCE: 3

Met Thr Met Pro His Arg Tyr Met Phe Leu Ala Val Phe Thr Leu Leu
1               5                   10                  15

Ala Leu Thr Ser Val Ala Ser Gly Ala Thr Glu Ala Cys Leu Pro Ala
            20                  25                  30

Gly Gln Arg Lys Ser Gly Met Asn Ile Asn Phe Tyr Gln Tyr Ser Leu
        35                  40                  45

Lys Asp Ser Ser Thr Tyr Ser Asn Ala Ala Tyr Met Ala Tyr Gly Tyr
    50                  55                  60

Ala Ser Lys Thr Lys Leu Gly Ser Val Gly Gly Gln Thr Asp Ile Ser
65                  70                  75                  80

Ile Asp Tyr Asn Ile Pro Cys Val Ser Ser Gly Thr Phe Pro Cys
                85                  90                  95

Pro Gln Glu Asp Ser Tyr Gly Asn Trp Gly Cys Lys Gly Met Gly Ala
            100                 105                 110

Cys Ser Asn Ser Gln Gly Ile Ala Tyr Trp Ser Thr Asp Leu Phe Gly
        115                 120                 125

Phe Tyr Thr Thr Pro Thr Asn Val Thr Leu Glu Met Thr Gly Tyr Phe
    130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                165                 170                 175

Ala Gln Gln Gln Pro Pro Ile Thr Ser Thr Asn Phe Thr Ile Asp Gly
            180                 185                 190

Ile Lys Pro Trp Gly Gly Ser Leu Pro Pro Asn Ile Glu Gly Thr Val
        195                 200                 205

Tyr Met Tyr Ala Gly Tyr Tyr Tyr Pro Met Lys Val Val Tyr Ser Asn
    210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
                245                 250                 255

Asp Leu Ser Gln Ser Asn Cys Thr Val Pro Asp Pro Ser Asn Tyr Ala
            260                 265                 270

Val Ser Thr Thr Thr Thr Thr Glu Pro Trp Thr Gly Thr Phe Thr
        275                 280                 285

Ser Thr Ser Thr Glu Met Thr Thr Val Thr Gly Thr Asn Gly Val Pro
    290                 295                 300

Thr Asp Glu Thr Val Ile Val Ile Arg Thr Pro Thr Thr Ala Ser Thr
305                 310                 315                 320

Ile Ile Thr Thr Thr Glu Pro Trp Asn Ser Thr Phe Thr Ser Thr Ser
                325                 330                 335

Thr Glu Leu Thr Thr Val Thr Gly Thr Asn Gly Val Arg Thr Asp Glu
            340                 345                 350

-continued

```
Thr Ile Ile Val Ile Arg Thr Pro Thr Thr Ala Thr Ala Ile Thr
            355                 360                 365
Thr Thr Glu Pro Trp Asn Ser Thr Phe Thr Ser Thr Ser Thr Glu Leu
370                 375                 380
Thr Thr Val Thr Gly Thr Asn Gly Leu Pro Thr Asp Glu Thr Ile Ile
385                 390                 395                 400
Val Ile Arg Thr Pro Thr Thr Ala Thr Thr Ala Met Thr Thr Thr Gln
            405                 410                 415
Pro Trp Asn Asp Thr Phe Thr Ser Thr Ser Thr Glu Leu Thr Thr Val
            420                 425                 430
Thr Gly Thr Asn Gly Leu Pro Thr Asp Glu Thr Ile Ile Val Ile Arg
            435                 440                 445
Thr Pro Thr Thr Ala Thr Thr Ala Met Thr Thr Thr Gln Pro Trp Asn
            450                 455                 460
Asp Thr Phe Thr Ser Thr Ser Thr Glu Leu Thr Thr Val Thr Gly Thr
465                 470                 475                 480
Asn Gly Leu Pro Thr Asp Glu Thr Ile Ile Val Ile Arg Thr Pro Thr
            485                 490                 495
Thr Ala Thr Thr Ala Met Thr Thr Thr Gln Pro Trp Asn Asp Thr Phe
            500                 505                 510
Thr Ser Thr Ser Thr Glu Ile Thr Thr Val Thr Gly Thr Asn Gly Leu
            515                 520                 525
Pro Thr Asp Glu Thr Ile Ile Val Ile Arg Thr Pro Thr Thr Ala Thr
            530                 535                 540
Thr Ala Met Thr Thr Pro Gln Pro Trp Asn Asp Thr Phe Thr Ser Thr
545                 550                 555                 560
Ser Thr Glu Met Thr Thr Val Thr Gly Thr Asn Gly Leu Pro Thr Asp
            565                 570                 575
Glu Thr Ile Ile Val Ile Arg Thr Pro Thr Thr Ala Thr Thr Ala Ile
            580                 585                 590
Thr Thr Thr Glu Pro Trp Asn Ser Thr Phe Thr Ser Thr Ser Thr Glu
            595                 600                 605
Met Thr Thr Val Thr Gly Thr Asn Gly Leu Pro Thr Asp Glu Thr Ile
            610                 615                 620
Ile Val Ile Arg Thr Pro Thr Thr Ala Thr Thr Ala Ile Thr Thr Thr
625                 630                 635                 640
Gln Pro Trp Asn Asp Thr Phe Thr Ser Thr Ser Thr Glu Met Thr Thr
            645                 650                 655
Val Thr Gly Thr Asn Gly Leu Pro Thr Asp Glu Thr Ile Ile Val Ile
            660                 665                 670
Arg Thr Pro Thr Thr Ala Thr Thr Ala Met Thr Thr Thr Gln Pro Trp
            675                 680                 685
Asn Asp Thr Phe Thr Ser Thr Ser Thr Glu Ile Thr Thr Val Thr Gly
            690                 695                 700
Thr Thr Gly Leu Pro Thr Asp Glu Thr Ile Ile Val Ile Arg Thr Pro
705                 710                 715                 720
Thr Thr Ala Thr Thr Ala Met Thr Thr Thr Gln Pro Trp Asn Asp Thr
            725                 730                 735
Phe Thr Ser Thr Ser Thr Glu Met Thr Thr Val Thr Gly Thr Asn Gly
            740                 745                 750
Val Pro Thr Asp Glu Thr Val Ile Val Ile Arg Thr Pro Thr Ser Glu
            755                 760                 765
Gly Leu Ile Ser Thr Thr Thr Glu Pro Trp Thr Gly Thr Phe Thr Ser
```

```
                    770             775             780
Thr Ser Thr Glu Met Thr Thr Val Thr Gly Thr Asn Gly Gln Pro Thr
785             790             795             800

Asp Glu Thr Val Ile Val Ile Arg Thr Pro Thr Ser Glu Gly Leu Val
                805             810             815

Thr Thr Thr Thr Glu Pro Trp Thr Gly Thr Phe Thr Ser Thr Ser Thr
            820             825             830

Glu Met Thr Thr Ile Thr Gly Thr Asn Gly Val Pro Thr Asp Glu Thr
            835             840             845

Val Ile Val Ile Arg Thr Pro Thr Ser Glu Gly Leu Ile Ser Thr Thr
850             855             860

Thr Glu Pro Trp Thr Gly Thr Phe Thr Ser Thr Ser Thr Glu Met Thr
865             870             875             880

Thr Ile Thr Gly Thr Asn Gly Gln Pro Thr Asp Glu Thr Val Ile Val
                885             890             895

Ile Arg Thr Pro Thr Ser Glu Gly Leu Ile Ser Thr Thr Thr Glu Pro
            900             905             910

Trp Thr Gly Thr Phe Thr Ser Thr Ser Thr Glu Met Thr His Val Thr
            915             920             925

Gly Thr Asn Gly Val Pro Thr Asp Glu Thr Val Ile Val Ile Arg Thr
930             935             940

Pro Thr Ser Glu Gly Leu Ile Ser Thr Thr Thr Glu Pro Trp Thr Gly
945             950             955             960

Thr Phe Thr Ser Thr Ser Thr Glu Val Thr Thr Ile Thr Gly Thr Asn
                965             970             975

Gly Gln Pro Thr Asp Glu Thr Val Ile Val Ile Arg Thr Pro Thr Ser
            980             985             990

Glu Gly Leu Ile Ser Thr Thr Thr Glu Pro Trp Thr Gly Thr Phe Thr
            995             1000            1005

Ser Thr Ser Thr Glu Met Thr Thr Val Thr Gly Thr Asn Gly Gln
    1010            1015            1020

Pro Thr Asp Glu Thr Val Ile Val Ile Arg Thr Pro Thr Ser Glu
    1025            1030            1035

Gly Leu Val Thr Thr Thr Thr Glu Pro Trp Thr Gly Thr Phe Thr
    1040            1045            1050

Ser Thr Ser Thr Glu Met Ser Thr Val Thr Gly Thr Asn Gly Leu
    1055            1060            1065

Pro Thr Asp Glu Thr Val Ile Val Val Lys Thr Pro Thr Thr Ala
    1070            1075            1080

Ile Ser Ser Ser Leu Ser Ser Ser Ser Gly Gln Ile Thr Ser
    1085            1090            1095

Ser Ile Thr Ser Ser Arg Pro Ile Ile Thr Pro Phe Tyr Pro Ser
    1100            1105            1110

Asn Gly Thr Ser Val Ile Ser Ser Ser Val Ile Ser Ser Ser Val
    1115            1120            1125

Thr Ser Ser Leu Phe Thr Ser Ser Pro Val Ile Ser Ser Ser Val
    1130            1135            1140

Ile Ser Ser Ser Thr Thr Thr Ser Thr Ser Ile Phe Ser Glu Ser
    1145            1150            1155

Ser Lys Ser Ser Val Ile Pro Thr Ser Ser Ser Thr Ser Gly Ser
    1160            1165            1170

Ser Glu Ser Glu Thr Ser Ser Ala Gly Ser Val Ser Ser Ser Ser
    1175            1180            1185
```

-continued

```
Phe Ile Ser Ser Glu Ser Ser Lys Ser Pro Thr Tyr Ser Ser Ser
    1190            1195                1200

Ser Leu Pro Leu Val Thr Ser Ala Thr Thr Ser Gln Glu Thr Ala
    1205            1210                1215

Ser Ser Leu Pro Pro Ala Thr Thr Thr Lys Thr Ser Glu Gln Thr
    1220            1225                1230

Thr Leu Val Thr Val Thr Ser Cys Glu Ser His Val Cys Thr Glu
    1235            1240                1245

Ser Ile Ser Pro Ala Ile Val Ser Thr Ala Thr Val Thr Val Ser
    1250            1255                1260

Gly Val Thr Thr Glu Tyr Thr Thr Trp Cys Pro Ile Ser Thr Thr
    1265            1270                1275

Glu Thr Thr Lys Gln Thr Lys Gly Thr Thr Glu Gln Thr Thr Glu
    1280            1285                1290

Thr Thr Lys Gln Thr Thr Val Val Thr Ile Ser Ser Cys Glu Ser
    1295            1300                1305

Asp Val Cys Ser Lys Thr Ala Ser Pro Ala Ile Val Ser Thr Ser
    1310            1315                1320

Thr Ala Thr Ile Asn Gly Val Thr Thr Glu Tyr Thr Thr Trp Cys
    1325            1330                1335

Pro Ile Ser Thr Thr Glu Ser Arg Gln Gln Thr Thr Leu Val Thr
    1340            1345                1350

Val Thr Ser Cys Glu Ser Gly Val Cys Ser Glu Thr Ala Ser Pro
    1355            1360                1365

Ala Ile Val Ser Thr Ala Thr Ala Thr Val Asn Asp Val Val Thr
    1370            1375                1380

Val Tyr Pro Thr Trp Arg Pro Gln Thr Ala Asn Glu Glu Ser Val
    1385            1390                1395

Ser Ser Lys Met Asn Ser Ala Thr Gly Glu Thr Thr Thr Asn Thr
    1400            1405                1410

Leu Ala Ala Glu Thr Thr Thr Asn Thr Val Ala Ala Glu Thr Ile
    1415            1420                1425

Thr Asn Thr Gly Ala Ala Glu Thr Lys Thr Val Val Thr Ser Ser
    1430            1435                1440

Leu Ser Arg Ser Asn His Ala Glu Thr Gln Thr Ala Ser Ala Thr
    1445            1450                1455

Asp Val Ile Gly His Ser Ser Val Val Ser Val Ser Glu Thr
    1460            1465                1470

Gly Asn Thr Lys Ser Leu Thr Ser Ser Gly Leu Ser Thr Met Ser
    1475            1480                1485

Gln Gln Pro Arg Ser Thr Pro Ala Ser Ser Met Val Gly Tyr Ser
    1490            1495                1500

Thr Ala Ser Leu Glu Ile Ser Thr Tyr Ala Gly Ser Ala Asn Ser
    1505            1510                1515

Leu Leu Ala Gly Ser Gly Leu Ser Val Phe Ile Ala Ser Leu Leu
    1520            1525                1530

Leu Ala Ile Ile
    1535

<210> SEQ ID NO 4
<211> LENGTH: 28
<212> TYPE: PRT
<213> ORGANISM: Saccharomyces cerevisiae
```

```
<400> SEQUENCE: 4

Glu Leu Thr Thr Val Thr Gly Thr Asn Gly Leu Pro Thr Asp Glu Thr
1               5                   10                  15

Ile Ile Val Ile Arg Thr Pro Thr Thr Ala Thr Thr
            20                  25

<210> SEQ ID NO 5
<211> LENGTH: 453
<212> TYPE: PRT
<213> ORGANISM: Saccharomyces cerevisiae

<400> SEQUENCE: 5

Ser Ser Ser Leu Ser Ser Ser Ser Gly Gln Ile Thr Ser Ser Ile
1               5                   10                  15

Thr Ser Ser Arg Pro Ile Ile Thr Pro Phe Tyr Pro Ser Asn Gly Thr
            20                  25                  30

Ser Val Ile Ser Ser Ser Val Ile Ser Ser Val Thr Ser Ser Leu
        35                  40                  45

Phe Thr Ser Ser Pro Val Ile Ser Ser Val Ile Ser Ser Thr
    50                  55                  60

Thr Thr Ser Thr Ser Ile Phe Ser Glu Ser Ser Lys Ser Ser Val Ile
65                  70                  75                  80

Pro Thr Ser Ser Ser Thr Ser Gly Ser Ser Glu Ser Glu Thr Ser Ser
                85                  90                  95

Ala Gly Ser Val Ser Ser Ser Phe Ile Ser Ser Glu Ser Ser Lys
            100                 105                 110

Ser Pro Thr Tyr Ser Ser Ser Leu Pro Leu Val Thr Ser Ala Thr
        115                 120                 125

Thr Ser Gln Glu Thr Ala Ser Ser Leu Pro Pro Ala Thr Thr Lys
    130                 135                 140

Thr Ser Glu Gln Thr Thr Leu Val Thr Val Thr Ser Cys Glu Ser His
145                 150                 155                 160

Val Cys Thr Glu Ser Ile Ser Pro Ala Ile Val Ser Thr Ala Thr Val
                165                 170                 175

Thr Val Ser Gly Val Thr Thr Glu Tyr Thr Thr Trp Cys Pro Ile Ser
            180                 185                 190

Thr Thr Glu Thr Thr Lys Gln Thr Lys Gly Thr Thr Glu Gln Thr Thr
        195                 200                 205

Glu Thr Thr Lys Gln Thr Thr Val Val Thr Ile Ser Ser Cys Glu Ser
    210                 215                 220

Asp Val Cys Ser Lys Thr Ala Ser Pro Ala Ile Val Ser Thr Ser Thr
225                 230                 235                 240

Ala Thr Ile Asn Gly Val Thr Thr Glu Tyr Thr Thr Trp Cys Pro Ile
                245                 250                 255

Ser Thr Thr Glu Ser Arg Gln Gln Thr Thr Leu Val Thr Val Thr Ser
            260                 265                 270

Cys Glu Ser Gly Val Cys Ser Glu Thr Ala Ser Pro Ala Ile Val Ser
        275                 280                 285

Thr Ala Thr Ala Thr Val Asn Asp Val Val Thr Val Tyr Pro Thr Trp
    290                 295                 300

Arg Pro Gln Thr Ala Asn Glu Glu Ser Val Ser Ser Lys Met Asn Ser
305                 310                 315                 320

Ala Thr Gly Glu Thr Thr Thr Asn Thr Leu Ala Glu Thr Thr Thr
                325                 330                 335
```

```
Asn Thr Val Ala Ala Glu Thr Ile Thr Asn Thr Gly Ala Ala Glu Thr
                340                 345                 350
Lys Thr Val Val Thr Ser Ser Leu Ser Arg Ser Asn His Ala Glu Thr
            355                 360                 365
Gln Thr Ala Ser Ala Thr Asp Val Ile Gly His Ser Ser Ser Val Val
        370                 375                 380
Ser Val Ser Glu Thr Gly Asn Thr Lys Ser Leu Thr Ser Ser Gly Leu
385                 390                 395                 400
Ser Thr Met Ser Gln Gln Pro Arg Ser Thr Pro Ala Ser Ser Met Val
                405                 410                 415
Gly Tyr Ser Thr Ala Ser Leu Glu Ile Ser Thr Tyr Ala Gly Ser Ala
            420                 425                 430
Asn Ser Leu Leu Ala Gly Ser Gly Leu Ser Val Phe Ile Ala Ser Leu
        435                 440                 445
Leu Leu Ala Ile Ile
    450

<210> SEQ ID NO 6
<211> LENGTH: 84
<212> TYPE: DNA
<213> ORGANISM: Saccharomyces cerevisiae

<400> SEQUENCE: 6
acatccaaaa atgacaatgc ctcatcgcta tatgtttttg gcagtctttta cacttctggc    60 actaactagt gtggcctcag gagc                                           84

<210> SEQ ID NO 7
<211> LENGTH: 1859
<212> TYPE: DNA
<213> ORGANISM: Saccharomyces cerevisiae

<400> SEQUENCE: 7
tccagtttgt catcatcatc ttcaggacaa atcaccagct ctatcacgtc ttcgcgtcca    60
attattaccc cattctatcc tagcaatgga acttctgtga tttcttcctc agtaatttct   120
tcctcagtca cttcttctct attcacttct ctccagtca tttcttcctc agtcatttct   180
tcttctacaa caacctccac ttctatattt tctgaatcat ctaaatcatc cgtcattcca   240
accagtagtt ccacctctgg ttcttctgag agcgaaacga gttcagctgg ttctgtctct   300
tcttcctctt ttatctcttc tgaatcatca aaatctccta catattcttc ttcatcatta   360
ccacttgtta ccagtgcgac aacaagccag gaaactgctt cttcattacc acctgctacc   420
actacaaaaa cgagcgaaca aaccactttg gttaccgtga catcctgcga gtctcatgtg   480
tgcactgaat ccatctcccc tgcgattgtt ccacagctacc tgttactgt tagcggcgtc   540 acaacagagt ataccacatg gtgccctatt tctactacag agacaacaaa gcaaaccaaa   600
gggacaacag agcaaaccac agaaacaaca aacaaaccac cggtagttac aatttcttct   660
tgtgaatctg acgtatgctc taagactgct ctccagcca ttgtatcac aagcactgct   720 actattaacg gcgttactac agaatacaca acatggtgtc ctatttccac cacagaatcg   780
aggcaacaaa caacgctagt tactgttact tcctgcgaat ctggtgtgtg ttccgaaact   840
gcttcacctg ccattgtttc gacggccacg gctactgtga atgatgttgt tacggtctat   900
cctacatgga ggcccagac tgcgaatgaa gagtctgtca gctctaaaat gaacagtgct   960
accggtgaga caacaaccaa tactttagct gctgaaacga ctaccaatac tgtagctgct  1020
gagacgatta ccaatactgg agctgctgag acgaaaacag tagtcacctc ttcgctttca  1080
```

-continued

```
agatctaatc acgctgaaac acagacggct tccgcgaccg atgtgattgg tcacagcagt    1140
agtgttgttt ctgtatccga aactggcaac accaagagtc taacaagttc cgggttgagt    1200
actatgtcgc aacagcctcg tagcacacca gcaagcagca tggtaggata tagtacagct    1260
tctttagaaa tttcaacgta tgctggcagt gccaacagct tactggccgg tagtggttta    1320
agtgtcttca ttgcgtcctt attgctggca attatttaat aaaattcgcg ttcttttac     1380 gtatctgtgt atcttttctt tgctaattat acgctgacat gaattatttt ttaactgttt    1440
ctcctccata ctttcaaata ttcaaattga ctaaatgata attcttgcgc ttcttatttt    1500
gaaaaagtag atatgtgtat cataaagaaa acgttattat tattgtctta ggcaacaaaa    1560
atccatgaaa agaattttac cgttatcgat atcattgtat ttattttatt tatttattca    1620
attttttttt ttttggttta tatcctgcaa acaacacttc gaattcaatt cgatatttca    1680
taagttacaa ctaacactta tagaaaccga tgtatgagta cttattatta acgaggaaaa    1740
atgccctatt tctttagca attaatgaac catcgccaac ttttgcttta acaattattg     1800 ccatttttcag cagtactaac gtaagatcta gtgtggttcg cttaggatgt tttcgagta    1859
```

<210> SEQ ID NO 8
<211> LENGTH: 6614
<212> TYPE: DNA
<213> ORGANISM: Saccharomyces cerevisiae

<400> SEQUENCE: 8

```
tccgtctcaa ccaattttgt acaagtcgtt gaaaaggacg gctctactgt agacaggtcg     60
attcaaagtc tggtctcaaa atagaaggta aatattatt gaacaaaaga ccactaaaag     120
gctatggtat gtccaataag atgcaaaata gacatttcac tcgctaatcg ttagtgggat    180
tatatcttac tatactcctt atctcattga atggcactag tcgatcgagg aacaaaaaag    240
gatcgaaccg attagcacgg atttccttaa gtaatttaaa ttaccaaaga agatccacat    300
cagcagtcga atgttcaaga tgccgtaagt ttaaaatctt tcgtatcttt ccccgatcct    360
gtctttcatc aatgaacttg aatatcaaga gtgaaaaaaa ctcatatggc ttctcttgaa    420
gagttagaaa gataggcaca tgccaattgt gtgcatagca cttactactc aacgatttca    480
caacctagca taatacgcga aaaaaaaagt gcatttattt aggtaagtct cattacctaa    540
acgccagttt gtttcacgta attggtaacg atgagggaac cgcagtagaa aaaacttta    600 ttcacaaacg attaaagtgt tatgctagcc agtttcaggc ttttttgtttt atgcaagaga    660 acattcgact agatgtccag ttaagtgtgc gtcactttc ctacggtgcc tcgcacatga    720
atgttatccg gcgcacgata cttatcaccg aaaaaccctta ttctacggaa aaccttatttt   780 acattaaagt tggaaaaatt tcctcttttt cctaataagg tggagctttt ggcttccagt    840
atgctttcac ggaattattt ctcatgtaca tttagctcca tttccagtgc ctccgatagg    900
gaggcatcat ggtactaccg tgacggagaa tacgtaggct gacttttcg tcagtttgtt     960 gtccgtttac aaaattggtg aatgaattct agccttcctc tgctcattaa ttgccctcac    1020
aagaatttgg aagtgcgtag acaggtaaaa gattgtacta cagaggtatt gtggaacctt    1080
ctacagtact tcggaataca cctaaaaggt tgttggatgc taaatttagc aaaagtcttt    1140
tttagctcac tattaggctt gttaaagtct gaaattgttg aaaggcactc aaaaagataa    1200
atcaacaatc agcattaacg gcacagttga aagagtcacc cacttgaaat tagctcggtt    1260
atcaaatata attatctctg gtaaagagct ctgcagcagg gttaatctat tcgcatactt    1320
```

```
acgctgtagg aacattttat tattaggatc cgactactgc ctacatattt attcggaagg    1380
catgatgtcg aaaatttttg agcttataaa aggaacatat ttcactcttg ctcgttgatg    1440
taagctctct tccgggttct tattttaat tcttgtcacc agtaaacaga acatccaaaa    1500
atgacaatgc ctcatcgcta tatgttttg gcagtcttta cacttctggc actaactagt    1560
gtggcctcag gagccacaga ggcgtgctta ccagcaggcc agaggaaaag tgggatgaat    1620
ataaattttt accagtattc attgaaagat tcctccacat attcgaatgc agcatatatg    1680
gcttatggat atgcctcaaa aaccaaacta ggttctgtcg gaggacaaac tgatatctcg    1740
attgattata atattcctg tgttagttca tcaggcacat ttccttgtcc tcaagaagat    1800
tcctatggaa actggggatg caaaggaatg ggtgcttgtt ctaatagtca aggaattgca    1860
tactggagta ctgatttatt tggtttctat actaccccaa caaacgtaac cctagaaatg    1920
acaggttatt ttttaccacc acagacgggt tcttacacat tcaagtttgc tacagttgac    1980
gactctgcaa ttctatcagt aggtggtgca accgcgttca actgttgtgc tcaacagcaa    2040
ccgccgatca catcaacgaa ctttaccatt gacggtatca agccatgggg tggaagtttg    2100
ccacctaata tcgaaggaac cgtctatatg tacgctggct actattatcc aatgaaggtt    2160
gtttactcga acgctgtttc ttggggtaca cttccaatta gtgtgacact tccagatggt    2220
accactgtaa gtgatgactt cgaagggtac gtctattcct ttgacgatga cctaagtcaa    2280
tctaactgta ctgtccctga cccttcaaat tatgctgtca gtaccactac aactacaacg    2340
gaaccatgga ccggtacttt cacttctaca tctactgaaa tgaccaccgt caccggtacc    2400
aacgcgttc caactgacga aaccgtcatt gtcatcagaa ctccaacaac tgctagcacc    2460
atcataacta caactgagcc atggaacagc acttttacct ctacttctac cgaattgacc    2520
acagtcactg gcaccaatgg tgtacgaact gacgaaacca tcattgtaat cagaacacca    2580
acaacagcca ctactgccat aactacaact gagccatgga acagcacttt tacctctact    2640
tctaccgaat tgaccacagt caccggtacc aatggtttgc caactgatga gaccatcatt    2700
gtcatcagaa caccaacaac agccactact gccatgacta caactcagcc atggaacgac    2760
acttttacct ctacttctac cgaattgacc acagtcaccg gtaccaatgg tttgccaact    2820
gatgagacca tcattgtcat cagaacacca acaacagcca ctactgccat gactacaact    2880
cagccatgga cgacactttt acctctact tctaccgaat tgaccacagt caccggtacc    2940
aatggtttgc caactgatga gaccatcatt gtcatcagaa caccaacaac agccactact    3000
gccatgacta caactcagcc atggaacgac acttttacct ctacatccac tgaaatcacc    3060
accgtcaccg gtaccaatgg tttgccaact gatgagacca tcattgtcat cagaacacca    3120
acaacagcca ctactgccat gactacacct cagccatgga cgacactttt acctctaca    3180
tccactgaaa tgaccaccgt caccggtacc aacggtttgc caactgatga accatcatt    3240
gtcatcagaa caccaacaac agccactact gccataacta caactgagcc atggaacagc    3300
acttttacct ctacatccac tgaaatgacc accgtcaccg gtaccaacgg tttgccaact    3360
gatgaaacca tcattgtcat cagaacacca acaacagcca ctactgccat aactacaact    3420
cagccatgga cgacactttt acctctaca tccactgaaa tgaccaccgt caccggtacc    3480
aacggtttgc caactgatga accatcatt gtcatcagaa caccaacaac agccactact    3540
gccatgacta caactcagcc atggaacgac acttttacct ctacatccac tgaaatcacc    3600
accgtcaccg gtaccaccgg tttgccaact gatgagacca tcattgtcat cagaacacca    3660
acaacagcca ctactgccat gactacaact cagccatgga cgacactttt acctctaca    3720
```

```
tccactgaaa tgaccaccgt caccggtacc aacggcgttc caactgacga aaccgtcatt    3780
gtcatcagaa ctccaactag tgaaggtcta atcagcacca ccactgaacc atggactggt    3840
actttcacct ctacatccac tgagatgacc accgtcaccg gtactaacgg tcaaccaact    3900
gacgaaaccg tgattgttat cagaactcca accagtgaag gtttggttac aaccaccact    3960
gaaccatgga ctggtacttt tacttctaca tctactgaaa tgaccaccat tactggaacc    4020
aacggcgttc caactgacga aaccgtcatt gtcatcagaa ctccaaccag tgaaggtcta    4080
atcagcacca ccactgaacc atggactggt acttttactt ctacatctac tgaaatgacc    4140
accattactg gaaccaatgg tcaaccaact gacgaaaccg ttattgttat cagaactcca    4200
actagtgaag gtctaatcag cactacaacg gaaccatgga ccggtacttt cacttctaca    4260
tctactgaaa tgacgcacgt caccggtacc aacggcgttc caactgacga aaccgtcatt    4320
gtcatcagaa ctccaaccag tgaaggtcta atcagcacca ccactgaacc atggactggc    4380
actttcactt cgacttccac tgaggttacc accatcactg gaaccaacgg tcaaccaact    4440
gacgaaactg tgattgttat cagaactcca accagtgaag gtctaatcag caccaccact    4500
gaaccatgga ctggtacttt cacttctaca tctactgaaa tgaccaccgt caccggtact    4560
aacggtcaac caactgacga aaccgtgatt gttatcagaa ctccaaccag tgaaggtttg    4620
gttacaacca ccactgaacc atggactggt actttcactt cgacttccac tgaaatgtct    4680
actgtcactg gaaccaatgg cttgccaact gatgaaactg tcattgttgt caaaactcca    4740
actactgcca tctcatccag tttgtcatca tcatcttcag gacaaatcac cagctctatc    4800
acgtcttcgc gtccaattat taccccattc tatcctagca atggaacttc tgtgatttct    4860
tcctcagtaa tttcttcctc agtcacttct tctctattca cttcttctcc agtcatttct    4920
tcctcagtca tttcttcttc tacaacaacc tccacttcta tattttctga atcatctaaa    4980
tcatccgtca ttccaaccag tagttccacc tctggttctt ctgagagcga aacgagttca    5040
gctggttctg tctcttcttc ctcttttatc tcttctgaat catcaaaatc tcctacatat    5100
tcttcttcat cattaccact tgttaccagt gcgacaacaa gccaggaaac tgcttcttca    5160
ttaccacctg ctaccactac aaaaacgagc gaacaaacca ctttggttac cgtgacatcc    5220
tgcgagtctc atgtgtgcac tgaatccatc tcccctgcga ttgtttccac agctactgtt    5280
actgttagcg gcgtcacaac agagtatacc acatggtgcc ctatttctac tacagagaca    5340
acaaagcaaa ccaaagggac aacagagcaa accacagaaa caacaaaaca aaccacggta    5400
gttacaattt cttcttgtga atctgacgta tgctctaaga ctgcttctcc agccattgta    5460
tctacaagca ctgctactat taacggcgtt actacagaat acacaacatg gtgtcctatt    5520
tccaccacag aatcgaggca acaaacaacg ctagttactg ttacttcctg cgaatctggt    5580
gtgtgttccg aaactgcttc acctgccatt gtttcgacgg ccacggctac tgtgaatgat    5640
gttgttacgg tctatcctac atggaggcca cagactgcga atgaagagtc tgtcagctct    5700
aaaatgaaca gtgctaccgg tgagacaaca accaatactt tagctgctga aacgactacc    5760
aatactgtag ctgctgagac gattaccaat actggagctg ctgagacgaa acagtagtc    5820 acctcttcgc tttcaagatc taatcacgct gaaacacaga cggcttccgc gaccgatgtg    5880
attggtcaca gcagtagtgt tgtttctgta tccgaaactg gcaacaccaa gagtctaaca    5940
agttccgggt tgagtactat gtcgcaacag cctcgtagca caccagcaag cagcatggta    6000
ggatatagta cagcttcttt agaaatttca acgtatgctg gcagtgccaa cagcttactg    6060
```

-continued

```
gccggtagtg gtttaagtgt cttcattgcg tccttattgc tggcaattat ttaataaaat      6120
tcgcgttctt tttacgtatc tgtgtatctt ttctttgcta attatacgct gacatgaatt      6180
attttttaac tgtttctcct ccatactttc aaatattcaa attgactaaa tgataattct      6240
tgcgcttctt attttgaaaa agtagatatg tgtatcataa agaaaacgtt attattattg      6300
tcttaggcaa caaaaatcca tgaaaagaat tttaccgtta tcgatatcat tgtatttatt      6360
ttatttattt attcaatttt tttttttttg gtttatatcc tgcaaacaac acttcgaatt      6420
caattcgata tttcataagt tacaactaac acttatagaa accgatgtat gagtacttat      6480
tattaacgag gaaaaatgcc ctattttctt tagcaattaa tgaaccatcg ccaacttttg      6540
ctttaacaat tattgccatt ttcagcagta ctaacgtaag atctagtgtg gttcgcttag      6600
gatgttttcg agta                                                        6614

<210> SEQ ID NO 9
<211> LENGTH: 37
<212> TYPE: DNA
<213> ORGANISM: Artificial Sequence
<220> FEATURE:
<223> OTHER INFORMATION: Synthetic construct

<400> SEQUENCE: 9
aaaaaaggcc accggggcca aaacgtgtga aacggtc                                37

<210> SEQ ID NO 10
<211> LENGTH: 38
<212> TYPE: DNA
<213> ORGANISM: Artificial Sequence
<220> FEATURE:
<223> OTHER INFORMATION: Synthetic construct

<400> SEQUENCE: 10
aaaaaaggcc ccagaggccc cctccacgaa tgggcact                               38

<210> SEQ ID NO 11
<211> LENGTH: 37
<212> TYPE: DNA
<213> ORGANISM: Artificial Sequence
<220> FEATURE:
<223> OTHER INFORMATION: Synthetic construct

<400> SEQUENCE: 11
aaaaaaggcc accggggccg catgtccctc gcagtgt                                37

<210> SEQ ID NO 12
<211> LENGTH: 39
<212> TYPE: DNA
<213> ORGANISM: Artificial Sequence
<220> FEATURE:
<223> OTHER INFORMATION: Synthetic construct

<400> SEQUENCE: 12
aaaaaaggcc ccagaggccc ctgggcattt cgaggggct                              39

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
aaacggaatt aaccctcca                                                    19
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
aaaccggcgt agaggatgca                                               20

<210> SEQ ID NO 15
<211> LENGTH: 14
<212> TYPE: DNA
<213> ORGANISM: Artificial Sequence
<220> FEATURE:
<223> OTHER INFORMATION: Synthetic construct

<400> SEQUENCE: 15
gcatgtccct cgca                                                     14

<210> SEQ ID NO 16
<211> LENGTH: 14
<212> TYPE: DNA
<213> ORGANISM: Artificial Sequence
<220> FEATURE:
<223> OTHER INFORMATION: Synthetic construct

<400> SEQUENCE: 16
cagtcccagg ggtt                                                     14

<210> SEQ ID NO 17
<211> LENGTH: 14
<212> TYPE: DNA
<213> ORGANISM: Artificial Sequence
<220> FEATURE:
<223> OTHER INFORMATION: Synthetic construct

<400> SEQUENCE: 17
aacccctggg actg                                                     14

<210> SEQ ID NO 18
<211> LENGTH: 14
<212> TYPE: DNA
<213> ORGANISM: Artificial Sequence
<220> FEATURE:
<223> OTHER INFORMATION: Synthetic construct

<400> SEQUENCE: 18
ggacgggggt attg                                                     14

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
gcatgtccct cgcagtgttc                                               20

<210> SEQ ID NO 20
<211> LENGTH: 55
<212> TYPE: DNA
<213> ORGANISM: Artificial Sequence
<220> FEATURE:
```

<223> OTHER INFORMATION: Synthetic construct

<400> SEQUENCE: 20
tgggcatttc gagggggctag tgctggcctc ggtgaccgca cggacggggg tattg    55

<210> SEQ ID NO 21
<211> LENGTH: 74
<212> TYPE: DNA
<213> ORGANISM: Artificial Sequence
<220> FEATURE:
<223> OTHER INFORMATION: Synthetic construct

<400> SEQUENCE: 21
atgacaatgc tcatcgcta tatgtttttg cagtctttta cacttctggc actaactagt    60
gtggcctcag gagc    74

<210> SEQ ID NO 22
<211> LENGTH: 168
<212> TYPE: PRT
<213> ORGANISM: Artificial Sequence
<220> FEATURE:
<223> OTHER INFORMATION: Synthetic construct

<400> SEQUENCE: 22

```
Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Val Leu Tyr Leu Tyr Asp Asn Gln Ile Thr Lys Leu Glu Pro Gly Val
        35                  40                  45

Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Lys Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Gly Leu Val Phe Gly Tyr Leu Asn Leu Asp Pro Asp Ser
    130                 135                 140

Ala Arg Cys Ser Gly Thr Asn Thr Pro Val Arg Ala Val Thr Glu Ala
145                 150                 155                 160

Ser Thr Ser Pro Ser Lys Cys Pro
                165
```

<210> SEQ ID NO 23
<211> LENGTH: 274
<212> TYPE: DNA
<213> ORGANISM: Artificial Sequence
<220> FEATURE:
<223> OTHER INFORMATION: Synthetic construct

<400> SEQUENCE: 23
atgacaatgc tcatcgcta tatgtttttg cagtctttta cacttctggc actaactagt    60
gtggcctcag gagctagcgg ggccaccggg gcctagtgat ccggcttagg ggcctctggg   120
gccgcggccg cacatcatca tcaccatcac ggggccgcag aacaaaaact catctcagaa   180

```
gaggatctga atggatctat cgaaggcaga ggcgactaca aggacgatga cgacaagaga      240
tcctacccat acgacgttcc agactacgcc atgg                                  274
```

<210> SEQ ID NO 24
<211> LENGTH: 137
<212> TYPE: DNA
<213> ORGANISM: Artificial Sequence
<220> FEATURE:
<223> OTHER INFORMATION: Synthetic construct

<400> SEQUENCE: 24

```
tgacaacgta caccttttgcg tgttaagatt ttattaaaac ttgttcatgc atcctctacg      60
ccggtttaaa cggaattaac cctccacttg acaacgtaca cctttgcgtg ttaagatttt     120
attaaaactt gttcatg                                                    137
```

<210> SEQ ID NO 25
<211> LENGTH: 143
<212> TYPE: PRT
<213> ORGANISM: Artificial Sequence
<220> FEATURE:
<223> OTHER INFORMATION: Synthetic construct

<400> SEQUENCE: 25

```
Ala Cys Pro Ser Gln Cys Ser Cys Asp Gln Thr Thr Val Tyr Cys His
1               5                   10                  15

Asn Arg Arg Leu Thr Ser Val Pro Thr Gly Ile Pro Thr Thr Thr Gln
            20                  25                  30

Val Leu Tyr Leu Tyr Asp Asn Gln Ile Thr Lys Leu Glu Pro Gly Val
        35                  40                  45

Phe Asp Arg Leu Thr Lys Leu Thr His Leu Ser Leu Gly Tyr Asn Gln
    50                  55                  60

Leu Lys Ser Val Pro Arg Gly Ala Phe Asp Asn Leu Lys Ser Leu Thr
65                  70                  75                  80

His Ile Trp Leu Leu Asn Asn Pro Trp Asp Cys Gln Cys Thr Asp Ile
                85                  90                  95

Leu Tyr Leu Lys Asn Trp Ile Val Gln His Ala Ser Ile Val Asn Pro
            100                 105                 110

His Thr His Gly Gly Val Asp Asn Val Lys Cys Ser Gly Thr Asn Thr
        115                 120                 125

Pro Val Arg Ala Val Thr Glu Ala Ser Thr Ser Pro Ser Lys Cys
    130                 135                 140
```

<210> SEQ ID NO 26
<211> LENGTH: 244
<212> TYPE: PRT
<213> ORGANISM: Artificial Sequence
<220> FEATURE:
<223> OTHER INFORMATION: Synthetic construct

<400> SEQUENCE: 26

```
Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60
```

```
Tyr Asn Gln Leu Gln Thr Leu Ser Ala Gly Val Phe Asp Asp Leu Thr
 65                  70                  75                  80

Glu Leu Gly Thr Leu Gly Leu Ala Asn Asn Gln Leu Ala Ser Leu Pro
                 85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Arg Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Thr Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 27
<211> LENGTH: 49
<212> TYPE: DNA
<213> ORGANISM: Artificial Sequence
<220> FEATURE:
<223> OTHER INFORMATION: Synthetic construct

<400> SEQUENCE: 27
tgacaacgta caccttttgcg tgttaagatt ttattaaaac ttgttcatg           49

<210> SEQ ID NO 28
<211> LENGTH: 168
<212> TYPE: PRT
<213> ORGANISM: Artificial Sequence
<220> FEATURE:
<223> OTHER INFORMATION: Synthetic Construct

<400> SEQUENCE: 28

Ala Cys Pro Ser Gln Cys Ser Cys Ser Gly Thr Thr Val Asp Cys Ser
 1               5                  10                  15

Gly Arg Ser Leu Ala Ser Val Pro Thr Gly Ile Pro Thr Thr Thr Gln
            20                  25                  30

Val Leu Tyr Leu Tyr Asp Asn Gln Ile Thr Lys Leu Glu Pro Gly Val
        35                  40                  45

Phe Asp Arg Leu Thr Gln Leu Thr Arg Leu Asp Leu Asp Asn Asn Gln
    50                  55                  60

Leu Thr Val Leu Pro Ala Gly Val Leu Asp Lys Leu Thr Gln Leu Thr
 65                  70                  75                  80

Gln Leu Ser Leu Asn Asp Asn Gln Leu Lys Ser Ile Pro Arg Gly Ala
                 85                  90                  95

Phe Asp Asn Leu Lys Ser Leu Thr His Ile Trp Leu Asn Asn Pro
            100                 105                 110

Trp Asp Cys Ala Cys Ser Asp Ile Leu Tyr Leu Ser Arg Trp Ile Ser
```

```
                115                 120                 125
Gln His Pro Gly Leu Val Phe Gly Tyr Leu Asn Leu Asp Pro Asp Ser
    130                 135                 140
Ala Arg Cys Ser Gly Thr Asn Thr Pro Val Arg Ala Val Thr Glu Ala
145                 150                 155                 160
Ser Thr Ser Pro Ser Lys Cys Pro
                165

<210> SEQ ID NO 29
<211> LENGTH: 168
<212> TYPE: PRT
<213> ORGANISM: Artificial Sequence
<220> FEATURE:
<223> OTHER INFORMATION: Synthetic Construct

<400> SEQUENCE: 29

Ala Cys Pro Ser Gln Cys Ser Cys Ser Gly Thr Thr Val Asp Cys Ser
1               5                   10                  15
Gly Lys Ser Leu Ala Ser Val Pro Thr Gly Ile Pro Thr Thr Thr Gln
            20                  25                  30
Val Leu Tyr Leu Tyr Asp Asn Gln Ile Thr Lys Leu Glu Pro Gly Val
        35                  40                  45
Phe Asp Arg Leu Thr Gln Leu Thr Arg Leu Asp Leu Asp Asn Asn Gln
    50                  55                  60
Leu Thr Val Leu Pro Ala Gly Val Phe Asn Lys Leu Thr Gln Leu Thr
65                  70                  75                  80
Gln Leu Ser Leu Asn Asp Asn Gln Leu Lys Ser Ile Pro Arg Gly Ala
                85                  90                  95
Phe Asp Asn Leu Lys Ser Leu Thr His Ile Trp Leu Asn Asn Pro
            100                 105                 110
Trp Asp Cys Ala Cys Ser Asp Ile Leu Tyr Leu Ser Arg Trp Ile Ser
        115                 120                 125
Gln His Pro Trp Leu Val Phe Gly Tyr Leu Asn Leu Asp His Asp Ser
    130                 135                 140
Ala Arg Cys Ser Gly Thr Asn Thr Pro Val Arg Ala Val Thr Glu Ala
145                 150                 155                 160
Ser Thr Ser Pro Ser Lys Cys Pro
                165

<210> SEQ ID NO 30
<211> LENGTH: 168
<212> TYPE: PRT
<213> ORGANISM: Artificial Sequence
<220> FEATURE:
<223> OTHER INFORMATION: Synthetic construct

<400> SEQUENCE: 30

Ala Cys Pro Ser Gln Cys Ser Cys Ser Gly Thr Thr Val Asp Cys Ser
1               5                   10                  15
Gly Lys Ser Leu Ala Ser Val Pro Thr Gly Ile Pro Thr Thr Thr Gln
            20                  25                  30
Val Leu Tyr Leu Tyr Asp Asn Gln Ile Thr Lys Leu Glu Pro Gly Val
        35                  40                  45
Phe Asp Arg Leu Thr Gln Leu Thr Arg Leu Asp Leu Asp Asn Asn Gln
    50                  55                  60
Leu Thr Val Leu Pro Ala Gly Val Phe Asp Lys Leu Thr Gln Leu Thr
65                  70                  75                  80
```

```
Gln Leu Ser Leu Asn Asp Asn Gln Leu Lys Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Trp Leu Val Phe Gly Tyr Leu Asn Leu Asp His Asp Ser
    130                 135                 140

Ala Arg Cys Ser Gly Thr Asn Thr Pro Val Arg Ala Val Thr Glu Ala
145                 150                 155                 160

Ser Thr Ser Pro Ser Lys Cys Pro
                165

<210> SEQ ID NO 31
<211> LENGTH: 168
<212> TYPE: PRT
<213> ORGANISM: Artificial Sequence
<220> FEATURE:
<223> OTHER INFORMATION: Synthetic Construct

<400> SEQUENCE: 31

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Val Leu Tyr Leu Tyr Asp Asn Arg Ile Thr Lys Leu Glu Pro Gly Val
        35                  40                  45

Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Arg Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Trp Leu Val Phe Gly Tyr Leu Asn Leu Asp His Asp Ser
    130                 135                 140

Ala Arg Cys Ser Gly Thr Asn Thr Pro Val Arg Ala Val Thr Lys Ala
145                 150                 155                 160

Ser Thr Ser Pro Ser Lys Cys Pro
                165

<210> SEQ ID NO 32
<211> LENGTH: 168
<212> TYPE: PRT
<213> ORGANISM: Artificial Sequence
<220> FEATURE:
<223> OTHER INFORMATION: Synthetic construct

<400> SEQUENCE: 32

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Val Leu Tyr Leu Tyr Asp Asn Gln Ile Thr Lys Leu Glu Pro Gly Val
        35                  40                  45
```

```
Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Lys Ser Ile Pro Arg Gly Ala
                85                  90                  95

Phe Asp Asn Leu Lys Ser Leu Thr His Ile Trp Leu Asn Asn Pro
                100                 105                 110

Trp Asp Cys Ala Cys Ser Asp Ile Leu Tyr Leu Ser Arg Trp Ile Ser
            115                 120                 125

Gln His Pro Gly Leu Val Phe Gly Tyr Leu Asn Leu Tyr Pro Asp Ser
        130                 135                 140

Ala Arg Cys Ser Gly Thr Asn Thr Pro Val Arg Thr Val Thr Glu Ala
145                 150                 155                 160

Ser Thr Ser Pro Ser Lys Cys Pro
                165
```

<210> SEQ ID NO 33
<211> LENGTH: 168
<212> TYPE: PRT
<213> ORGANISM: Artificial Sequence
<220> FEATURE:
<223> OTHER INFORMATION: Synthetic Construct

<400> SEQUENCE: 33

```
Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
                20                  25                  30

Val Leu Tyr Leu Tyr Asp Asn Gln Ile Thr Lys Leu Glu Pro Gly Val
            35                  40                  45

Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Val Asn Gln Leu Lys Ser Ile Pro Arg Gly Ala
                85                  90                  95

Phe Asp Asn Leu Lys Ser Leu Thr His Ile Trp Leu Asn Asn Pro
                100                 105                 110

Trp Asp Cys Ala Cys Ser Asp Ile Leu Tyr Leu Ser Arg Trp Ile Ser
            115                 120                 125

Gln His Pro Gly Leu Val Phe Gly Tyr Leu Asn Leu Tyr Pro Asp Ser
        130                 135                 140

Ala Arg Cys Ser Gly Thr Asn Thr Pro Val Arg Ala Val Thr Glu Ala
145                 150                 155                 160

Ser Thr Ser Pro Ser Lys Cys Pro
                165
```

<210> SEQ ID NO 34
<211> LENGTH: 167
<212> TYPE: PRT
<213> ORGANISM: Artificial Sequence
<220> FEATURE:
<223> OTHER INFORMATION: Synthetic Construct

<400> SEQUENCE: 34

```
Ala Cys Pro Ser Gln Cys Ser Cys Ser Gly Thr Thr Val Asp Cys Ser
```

```
                1               5                  10                 15
Gly Lys Ser Leu Ala Ser Val Pro Thr Gly Ile Pro Thr Thr Thr Gln
                20                  25                 30

Val Leu Tyr Leu Tyr Asp Asn Gln Ile Thr Lys Leu Glu Pro Gly Val
                35                  40                 45

Phe Asp Arg Leu Thr Gln Leu Thr Arg Leu Asp Leu Asp Asn Asn Gln
            50                  55                 60

Leu Thr Val Leu Pro Ala Gly Val Phe Asp Lys Leu Thr Gln Leu Thr
65                  70                  75                 80

Gln Leu Ser Leu Asn Asp Asn Gln Leu Lys Ser Ile Pro Arg Gly Ala
                85                  90                 95

Phe Asp Asn Leu Lys Ser Leu Thr His Ile Trp Leu Leu Asn Asn Pro
            100                 105                110

Trp Asp Cys Ala Cys Ser Asp Ile Leu Tyr Leu Ser Arg Trp Ile Ser
            115                 120                125

Gln His Pro Gly Leu Val Phe Gly Tyr Leu Asn Leu Asp Pro Asp Ser
            130                 135                140

Ala Arg Cys Ser Gly Thr Asn Thr Pro Val Arg Ala Val Thr Glu Ala
145                 150                 155                160

Ser Thr Ser Pro Ser Lys Cys
                165
```

<210> SEQ ID NO 35
<211> LENGTH: 168
<212> TYPE: PRT
<213> ORGANISM: Artificial Sequence
<220> FEATURE:
<223> OTHER INFORMATION: Synthetic construct

<400> SEQUENCE: 35

```
Ala Cys Pro Ser Gln Cys Ser Cys Ser Gly Thr Thr Val Asp Cys Ser
1               5                   10                 15

Gly Lys Ser Leu Ala Ser Val Pro Thr Gly Ile Pro Thr Thr Thr Gln
                20                  25                 30

Val Leu Tyr Leu Tyr Asp Asn Gln Ile Thr Lys Leu Glu Pro Gly Val
                35                  40                 45

Phe Asp Arg Leu Thr Gln Leu Thr Arg Leu Asp Leu Asp Asn Asn Gln
            50                  55                 60

Leu Thr Val Leu Pro Ala Gly Val Phe Asn Lys Leu Thr Gln Leu Thr
65                  70                  75                 80

Gln Leu Ser Leu Asn Asp Asn Gln Leu Lys Ser Ile Pro Arg Gly Ala
                85                  90                 95

Phe Asp Asn Leu Lys Ser Leu Thr His Ile Trp Leu Leu Asn Asn Pro
            100                 105                110

Trp Asp Cys Ala Cys Ser Asp Ile Leu Tyr Leu Ser Arg Trp Ile Ser
            115                 120                125

Gln His Pro Trp Leu Val Phe Gly Tyr Leu Asn Leu Asp His Asp Ser
            130                 135                140

Ala Arg Cys Ser Gly Thr Asn Thr Pro Val Arg Ala Val Thr Glu Ala
145                 150                 155                160

Ser Thr Ser Pro Ser Lys Cys Pro
                165
```

<210> SEQ ID NO 36
<211> LENGTH: 167
<212> TYPE: PRT

<213> ORGANISM: Artificial Sequence
<220> FEATURE:
<223> OTHER INFORMATION: Synthetic Construct

<400> SEQUENCE: 36

```
Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Val Leu Tyr Leu Tyr Asp Asn Gln Ile Thr Lys Leu Glu Pro Gly Val
        35                  40                  45

Phe Asp Arg Leu Thr Gln Leu Thr Arg Leu Asp Leu Asp Asn Asn Gln
50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Lys Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Trp Leu Val Phe Gly Tyr Leu Asn Leu Asp His Asp Ser
130                 135                 140

Ala Arg Cys Ser Gly Thr Asn Thr Pro Val Arg Ala Val Thr Glu Ala
145                 150                 155                 160

Ser Thr Ser Pro Ser Lys Cys
                165
```

<210> SEQ ID NO 37
<211> LENGTH: 167
<212> TYPE: PRT
<213> ORGANISM: Artificial Sequence
<220> FEATURE:
<223> OTHER INFORMATION: Synthetic Construct

<400> SEQUENCE: 37

```
Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
            20                  25                  30

Val Leu Tyr Leu Tyr Asp Asn Arg Ile Thr Lys Leu Glu Pro Gly Val
        35                  40                  45

Phe Asp Arg Leu Thr Gln Leu Thr Arg Leu Asp Leu Asp Asn Asn Gln
50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Arg Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Trp Leu Val Phe Gly Tyr Leu Asn Leu Asp His Asp Ser
130                 135                 140

Ala Arg Cys Ser Gly Thr Asn Thr Pro Val Arg Ala Val Thr Lys Ala
145                 150                 155                 160
```

```
Ser Thr Ser Pro Ser Lys Cys
            165
```

```
<210> SEQ ID NO 38
<211> LENGTH: 167
<212> TYPE: PRT
<213> ORGANISM: Artificial Sequence
<220> FEATURE:
<223> OTHER INFORMATION: Synthetic Construct

<400> SEQUENCE: 38

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
                20                  25                  30

Val Leu Tyr Leu Tyr Asp Asn Gln Ile Thr Lys Leu Glu Pro Gly Val
            35                  40                  45

Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Asp Asn Gln Leu Lys Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125

Gln His Pro Gly Leu Val Phe Gly Tyr Leu Asn Leu Tyr Pro Asp Ser
    130                 135                 140

Ala Arg Cys Ser Gly Thr Asn Thr Pro Val Arg Thr Val Thr Glu Ala
145                 150                 155                 160

Ser Thr Ser Pro Ser Lys Cys
            165
```

```
<210> SEQ ID NO 39
<211> LENGTH: 168
<212> TYPE: PRT
<213> ORGANISM: Artificial Sequence
<220> FEATURE:
<223> OTHER INFORMATION: Synthetic construct

<400> SEQUENCE: 39

Ala Cys Pro Ser Gln Cys Ser Cys Ser Gly Thr Thr Val Asp Cys Ser
1               5                   10                  15

Gly Lys Ser Leu Ala Ser Val Pro Thr Gly Ile Pro Thr Thr Thr Gln
                20                  25                  30

Val Leu Tyr Leu Tyr Asp Asn Gln Ile Thr Lys Leu Glu Pro Gly Val
            35                  40                  45

Phe Asp Arg Leu Thr Gln Leu Thr Arg Leu Asp Leu Asp Asn Asn Gln
    50                  55                  60

Leu Thr Val Leu Pro Ala Gly Val Phe Asp Lys Leu Thr Gln Leu Thr
65                  70                  75                  80

Gln Leu Ser Leu Asn Val Asn Gln Leu Lys Ser Ile Pro Arg Gly Ala
                85                  90                  95

Phe Asp Asn Leu Lys Ser Leu Thr His Ile Trp Leu Leu Asn Asn Pro
            100                 105                 110

Trp Asp Cys Ala Cys Ser Asp Ile Leu Tyr Leu Ser Arg Trp Ile Ser
        115                 120                 125
```

Gln His Pro Gly Leu Val Phe Gly Tyr Leu Asn Leu Tyr Pro Asp Ser
    130                 135                 140

Ala Arg Cys Ser Gly Thr Asn Thr Pro Val Arg Ala Val Thr Glu Ala
145                 150                 155                 160

Ser Thr Ser Pro Ser Lys Cys Pro
                165

<210> SEQ ID NO 40
<211> LENGTH: 143
<212> TYPE: PRT
<213> ORGANISM: Artificial Sequence
<220> FEATURE:
<223> OTHER INFORMATION: Synthetic construct

<400> SEQUENCE: 40

Ala Cys Pro Ser Gln Cys Ser Cys Asp Gln Thr Thr Val Tyr Cys His
1               5                   10                  15

Asn Arg Arg Leu Thr Ser Val Pro Ala Gly Ile Pro Thr Asp Arg Gln
            20                  25                  30

Asn Leu Trp Leu Tyr Asp Asn Gln Ile Thr Lys Leu Glu Pro Gly Val
        35                  40                  45

Phe Asp Arg Leu Thr Lys Leu Thr His Leu Ser Leu Gly Tyr Asn Gln
    50                  55                  60

Leu Lys Ser Val Pro Arg Gly Ala Phe Asp Asn Leu Lys Ser Leu Thr
65                  70                  75                  80

His Ile Trp Leu Leu Asn Asn Pro Trp Asp Cys Glu Cys Ser Asp Ile
                85                  90                  95

Leu Tyr Leu Lys Asn Trp Ile Val Gln His Ala Ser Ile Val Asn Pro
            100                 105                 110

Gly Asn Tyr Gly Gly Val Asp Asn Val Lys Cys Phe Gly Thr Asn Thr
        115                 120                 125

Pro Val Arg Ala Val Thr Glu Ala Ser Thr Ser Pro Ser Lys Cys
    130                 135                 140

<210> SEQ ID NO 41
<211> LENGTH: 89
<212> TYPE: PRT
<213> ORGANISM: Artificial Sequence
<220> FEATURE:
<223> OTHER INFORMATION: Synthetic Construct

<400> SEQUENCE: 41

Met Thr Met Pro His Arg Tyr Met Phe Leu Ala Val Phe Thr Leu Leu
1               5                   10                  15

Ala Leu Thr Ser Val Ala Ser Gly Ala Ser Gly Ala Thr Gly Ala Ser
            20                  25                  30

Gly Leu Gly Ala Ser Gly Ala Ala Ala His His His His His His
        35                  40                  45

Gly Ala Ala Glu Gln Lys Leu Ile Ser Glu Glu Asp Leu Asn Gly Ser
    50                  55                  60

Ile Glu Gly Arg Gly Asp Tyr Lys Asp Asp Asp Lys Arg Ser Tyr
65                  70                  75                  80

Pro Tyr Asp Val Pro Asp Tyr Ala Met
                85

<210> SEQ ID NO 42
<211> LENGTH: 244
<212> TYPE: PRT

<213> ORGANISM: Artificial Sequence
<220> FEATURE:
<223> OTHER INFORMATION: Synthetic Construct

<400> SEQUENCE: 42

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Arg Leu Asn Thr Asn Gln Leu Gln Ser Ile Pro
    130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 43
<211> LENGTH: 244
<212> TYPE: PRT
<213> ORGANISM: Artificial Sequence
<220> FEATURE:
<223> OTHER INFORMATION: Synthetic Construct

<400> SEQUENCE: 43

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro

```
                    85                  90                  95
Leu Gly Val Phe Asp His Leu Thr Gln Leu Asp Lys Leu Tyr Leu Gly
                100                 105                 110

Gly Asn Gln Leu Lys Ser Leu Pro Ser Gly Val Val Asp Arg Leu Thr
                115                 120                 125

Lys Leu Lys Glu Leu Arg Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
                180                 185                 190

Cys Glu Ile Leu Tyr Leu Ser Gln Trp Ile Arg Glu Asn Ser Asn Lys
                195                 200                 205

Val Lys Asp Gly Thr Gly Gln Asn Leu His Glu Ser Pro Asp Gly Val
                210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 44
<211> LENGTH: 244
<212> TYPE: PRT
<213> ORGANISM: Artificial Sequence
<220> FEATURE:
<223> OTHER INFORMATION: Synthetic Construct

<400> SEQUENCE: 44

Cys Glu Thr Val Thr Gly Cys Thr Cys Asn Glu Gly Lys Lys Glu Val
1               5                   10                  15

Asp Cys Gln Gly Lys Gly Leu Asp Ser Val Pro Ser Gly Ile Pro Ala
                20                  25                  30

Asp Thr Glu Lys Leu Asp Leu Gln Ser Thr Gly Leu Ala Thr Leu Ser
                35                  40                  45

Asp Ala Thr Phe Arg Gly Leu Thr Lys Leu Thr Trp Leu Asn Leu Asp
50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
                100                 105                 110

Gly Asn Gln Leu Lys Ser Leu Pro Ser Gly Val Phe Asp Arg Leu Thr
                115                 120                 125

Lys Leu Lys Glu Leu Arg Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
                180                 185                 190

Cys Glu Ile Leu Tyr Leu Ser Gln Trp Ile Arg Glu Asn Ser Asn Lys
                195                 200                 205
```

-continued

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 45
<211> LENGTH: 244
<212> TYPE: PRT
<213> ORGANISM: Artificial Sequence
<220> FEATURE:
<223> OTHER INFORMATION: Synthetic Construct

<400> SEQUENCE: 45

Cys Glu Thr Val Thr Gly Cys Thr Cys Asn Glu Gly Lys Lys Glu Val
1               5                   10                  15

Asn Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

His Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Trp Leu Asn Thr Asn Gln Leu Gln Ser Ile Pro
    130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 46
<211> LENGTH: 244
<212> TYPE: PRT
<213> ORGANISM: Artificial Sequence
<220> FEATURE:
<223> OTHER INFORMATION: Synthetic Construct

<400> SEQUENCE: 46

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Trp Leu Asn Thr Asn Gln Leu Gln Ser Ile Pro
    130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 47
<211> LENGTH: 244
<212> TYPE: PRT
<213> ORGANISM: Artificial Sequence
<220> FEATURE:
<223> OTHER INFORMATION: Synthetic Construct

<400> SEQUENCE: 47

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Trp Leu Asn Ile Asn Gln Leu Gln Ser Ile Pro

```
                130                 135                 140
Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
                180                 185                 190

Cys Glu Ile Leu Tyr Leu Ser Gln Trp Ile Arg Glu Asn Ser Asn Lys
                195                 200                 205

Val Lys Asp Gly Thr Gly Gln Asn Leu His Glu Ser Pro Asp Gly Val
            210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 48
<211> LENGTH: 244
<212> TYPE: PRT
<213> ORGANISM: Artificial Sequence
<220> FEATURE:
<223> OTHER INFORMATION: Synthetic Construct

<400> SEQUENCE: 48

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
                20                  25                  30

Asp Thr Glu Lys Leu Asp Leu Gln Ser Thr Gly Leu Ala Thr Leu Ser
            35                  40                  45

Asp Ala Thr Phe Arg Gly Leu Thr Lys Leu Thr Trp Leu Asn Leu Asp
50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
                100                 105                 110

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
                180                 185                 190

Cys Glu Ile Leu Tyr Leu Ser Gln Trp Ile Arg Glu Asn Ser Asn Lys
            195                 200                 205

Val Lys Asp Gly Thr Gly Gln Asn Leu His Glu Ser Pro Asp Gly Val
            210                 215                 220

Thr Cys Ser Asp Gly Thr Val Val Arg Thr Val Thr Asn Glu Thr Leu
225                 230                 235                 240

Lys Tyr Glu Cys
```

-continued

```
<210> SEQ ID NO 49
<211> LENGTH: 244
<212> TYPE: PRT
<213> ORGANISM: Artificial Sequence
<220> FEATURE:
<223> OTHER INFORMATION: Synthetic Construct

<400> SEQUENCE: 49

Cys Glu Thr Val Thr Gly Cys Thr Cys Asn Glu Gly Lys Lys Glu Val
1               5                   10                  15

Asp Cys Gln Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
        115                 120                 125

Lys Leu Lys Glu Leu Trp Leu Asn Thr Asn Gln Leu Gln Ser Ile Pro
    130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
    210                 215                 220

Thr Cys Ser Asp Gly Arg Val Val Arg Thr Val Thr Asn Glu Thr Leu
225                 230                 235                 240

Lys Tyr Glu Cys

<210> SEQ ID NO 50
<211> LENGTH: 244
<212> TYPE: PRT
<213> ORGANISM: Artificial Sequence
<220> FEATURE:
<223> OTHER INFORMATION: Synthetic Construct

<400> SEQUENCE: 50

Cys Glu Thr Val Thr Gly Cys Thr Cys Asn Glu Gly Lys Lys Glu Val
1               5                   10                  15

Asn Thr Ala Gly Lys Ser Leu Asp Ser Val Pro Ser Gly Ile Pro Ala
            20                  25                  30

Asp Thr Glu Lys Leu Asp Leu Gln Ser Thr Gly Leu Ala Thr Leu Ser
        35                  40                  45

Asp Ala Thr Phe Arg Gly Leu Thr Lys Leu Thr Trp Leu Asn Leu Asp
    50                  55                  60
```

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
            85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
            130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
            165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
            195                 200                 205

Val Lys Asp Gly Thr Gly Gln Asn Leu His Glu Ser Pro Asp Gly Val
            210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 51
<211> LENGTH: 244
<212> TYPE: PRT
<213> ORGANISM: Artificial Sequence
<220> FEATURE:
<223> OTHER INFORMATION: Synthetic Construct

<400> SEQUENCE: 51

Cys Glu Thr Val Thr Gly Cys Thr Cys Asn Glu Gly Lys Lys Glu Val
1               5                   10                  15

Asn Cys Gln Tyr Lys Gly Leu Lys Ala Val Pro Ser Gly Ile Pro Ala
            20                  25                  30

Asp Thr Glu Lys Leu Asp Leu Gln Ser Thr Gly Leu Ala Thr Leu Ser
            35                  40                  45

Asp Ala Thr Phe Arg Gly Leu Thr Lys Leu Thr Trp Leu Asn Leu Asp
            50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
            85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
            130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
            165                 170                 175

Lys Leu Gln Thr Ile Thr Leu Phe Gly Asn Gln Phe Asp Cys Ser Arg 180                 185                 190

Cys Glu Ile Leu Tyr Leu Ser Gln Trp Ile Arg Glu Asn Ser Asn Lys
            195                 200                 205

Val Lys Asp Gly Thr Gly Gln Asn Leu His Glu Ser Pro Asp Gly Val
        210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 52
<211> LENGTH: 244
<212> TYPE: PRT
<213> ORGANISM: Artificial Sequence
<220> FEATURE:
<223> OTHER INFORMATION: Synthetic Construct

<400> SEQUENCE: 52

Cys Glu Thr Val Thr Gly Cys Thr Cys Asn Glu Gly Lys Lys Glu Val
1               5                   10                  15

Asn Cys Gln Tyr Lys Gly Leu Lys Ala Val Pro Ser Gly Ile Pro Ala
            20                  25                  30

Asp Thr Glu Lys Leu Asp Leu Gln Ser Thr Gly Leu Thr Thr Leu Ser
        35                  40                  45

Asp Ala Thr Phe Arg Gly Leu Thr Lys Leu Thr Trp Leu Asn Leu Asp
50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
            85                  90                  95

Leu Gly Val Phe Asp His Leu Thr Gln Leu Asp Lys Leu Tyr Leu Gly
            100                 105                 110

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
            195                 200                 205

Val Lys Asp Gly Thr Gly Gln Asn Leu His Glu Ser Pro Asp Gly Val
        210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 53
<211> LENGTH: 244
<212> TYPE: PRT
<213> ORGANISM: Artificial Sequence
<220> FEATURE:
<223> OTHER INFORMATION: Synthetic Construct

<400> SEQUENCE: 53

```
Cys Glu Thr Val Thr Gly Cys Thr Cys Asn Glu Gly Lys Lys Glu Val
1               5                   10                  15

Asn Cys Gln Tyr Lys Gly Leu Lys Ala Val Pro Ser Gly Ile Pro Ala
                20                  25                  30

Asp Thr Glu Lys Leu Asp Leu Gln Ser Thr Gly Leu Ala Thr Leu Ser
            35                  40                  45

Asp Thr Ala Phe Arg Gly Leu Thr Lys Leu Thr Trp Leu Asn Leu Asp
        50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
                100                 105                 110

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
                165                 170                 175

Lys Leu Gln Thr Ile Thr Leu Phe Gly Asn Gln Phe Asp Cys Ser Arg
            180                 185                 190

Cys Glu Ile Leu Tyr Leu Ser Gln Trp Ile Arg Glu Asn Ser Asn Lys
        195                 200                 205

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 54
<211> LENGTH: 244
<212> TYPE: PRT
<213> ORGANISM: Artificial Sequence
<220> FEATURE:
<223> OTHER INFORMATION: Synthetic Construct

<400> SEQUENCE: 54

Cys Glu Thr Val Thr Gly Cys Thr Cys Asn Glu Gly Lys Lys Glu Val
1               5                   10                  15

Asn Cys Gln Tyr Lys Gly Leu Lys Ala Val Pro Ser Gly Ile Pro Ala
                20                  25                  30

Asp Thr Glu Lys Leu Asp Leu Gln Ser Thr Gly Leu Ala Thr Leu Ser
            35                  40                  45

Asp Thr Ala Phe Arg Gly Leu Thr Lys Leu Thr Trp Leu Asn Leu Asp
        50                  55                  60

Tyr Asn Gln Leu Gln Thr Leu Ser Ala Gly Val Phe Asp Asp Leu Thr
65                  70                  75                  80

Glu Leu Gly Thr Leu Gly Leu Ala Asn Asn Gln Leu Ala Ser Leu Pro
                85                  90                  95

Leu Gly Val Phe Asp His Leu Thr Gln Leu Asp Lys Leu Tyr Leu Gly
                100                 105                 110
```

Gly Asn Gln Leu Lys Ser Leu Pro Ser Gly Val Phe Asp Arg Leu Thr
            115                 120                 125

Lys Leu Lys Glu Leu Trp Leu Asn Thr Asn Gln Leu Gln Ser Ile Pro
130                 135                 140

Ala Gly Ala Phe Asp Lys Leu Thr Asn Leu Gln Thr Leu Ser Leu Ser
145                 150                 155                 160

Thr Asn Gln Leu Gln Ser Val Pro His Gly Ala Phe Asp Arg Leu Gly
            165                 170                 175

Lys Leu Gln Thr Ile Thr Leu Phe Gly Ser Gln Phe Asp Cys Ser Arg
            180                 185                 190

Cys Glu Ile Leu Tyr Leu Ser Gln Trp Ile Arg Glu Asn Ser Asn Lys
            195                 200                 205

Val Lys Asp Gly Thr Gly Gln Asn Leu His Glu Ser Pro Asp Gly Val
    210                 215                 220

Thr Cys Ser Asp Gly Lys Val Val Arg Thr Val Thr Asn Glu Thr Leu
225                 230                 235                 240

Lys Tyr Glu Cys

<210> SEQ ID NO 55
<211> LENGTH: 137
<212> TYPE: PRT
<213> ORGANISM: Artificial Sequence
<220> FEATURE:
<223> OTHER INFORMATION: Synthetic Construct

<400> SEQUENCE: 55

Ala Cys Thr Gly Thr Thr Gly Cys Ala Thr Gly Thr Gly Gly Ala Ala
1               5                   10                  15

Ala Cys Gly Cys Ala Cys Ala Ala Thr Thr Cys Thr Ala Ala Ala Ala
            20                  25                  30

Thr Ala Ala Thr Thr Thr Thr Gly Ala Ala Cys Ala Ala Gly Thr Ala
            35                  40                  45

Cys Gly Thr Ala Gly Gly Ala Gly Ala Thr Gly Cys Gly Gly Cys Cys
    50                  55                  60

Ala Ala Ala Thr Thr Thr Gly Cys Cys Thr Thr Ala Thr Ala Thr Gly
65                  70                  75                  80

Gly Gly Ala Gly Gly Thr Gly Ala Ala Cys Thr Gly Thr Thr Gly Cys
                85                  90                  95

Ala Thr Gly Thr Gly Gly Ala Ala Cys Gly Cys Ala Cys Ala Ala Thr
            100                 105                 110

Thr Thr Cys Thr Ala Ala Ala Ala Thr Ala Ala Thr Thr Thr Thr Gly
            115                 120                 125

Ala Ala Cys Ala Ala Gly Thr Ala Cys
    130                 135

<210> SEQ ID NO 56
<211> LENGTH: 24
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be Leu, Ile, Val
<220> FEATURE:

```
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acide
<220> FEATURE:
<221> NAME/KEY: MISC_FEATURE
<222> LOCATION: (10)..(10)
<223> OTHER INFORMATION: Xaa is Asn, Thr, Ser or Cys
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Leu, Ile or Val
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Leu, Ile or Val
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is any amino acid
<220> FEATURE:
<221> NAME/KEY: MISC_FEATURE
<222> LOCATION: (23)..(23)
<223> OTHER INFORMATION: Xaa is Leu, Ile or Val
<220> FEATURE:
<221> NAME/KEY: MISC_FEATURE
<222> LOCATION: (24)..(24)
<223> OTHER INFORMATION: Xaa is any amino acid

<400> SEQUENCE: 56

Xaa Xaa Xaa Xaa Xaa Xaa Xaa Xaa Xaa Xaa Xaa Xaa Xaa Xaa Pro
1               5                   10                  15

Xaa Gly Xaa Phe Asp Xaa Xaa Xaa
            20
```

```
<210> SEQ ID NO 57
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be Leu, Ile, Val
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Asn, Thr, Ser or Cys
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Ala, Val, Ile, Leu, Met, Phe, Tyr or Trp
<220> FEATURE:
<221> NAME/KEY: MISC_FEATURE
<222> LOCATION: (13)..(13)
<223> OTHER INFORMATION: Xaa can ve any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Ala, Val, Ile,Leu, Met, Phe, Tyr or Trp
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
```

<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is any amino acid
<220> FEATURE:
<221> NAME/KEY: MISC_FEATURE
<222> LOCATION: (23)..(23)
<223> OTHER INFORMATION: Xaa is Leu, Ile or Val
<220> FEATURE:
<221> NAME/KEY: MISC_FEATURE
<222> LOCATION: (24)..(24)
<223> OTHER INFORMATION: Xaa is any amino acid

<400> SEQUENCE: 57

Xaa Xaa Xaa Xaa Xaa Xaa Xaa Xaa Xaa Xaa Xaa Xaa Xaa Xaa Xaa Xaa
1               5                   10                  15

Xaa Xaa Xaa Phe Xaa Xaa Xaa Xaa
            20

<210> SEQ ID NO 58
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Leu, Ile or Val
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE

```
<222> LOCATION: (10)..(10)
<223> OTHER INFORMATION: Xaa is Asn, Thr, Ser or Cys
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Leu, Ile or Val
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Leu, Ile or Val
<220> FEATURE:
<221> NAME/KEY: MISC_FEATURE
<222> LOCATION: (17)..(24)
<223> OTHER INFORMATION: Xaa is any amino acid

<400> SEQUENCE: 58

Xaa Xaa Xaa Xaa Xaa Xaa Xaa Xaa Xaa Xaa Xaa Xaa Xaa Xaa Xaa Pro
1               5                   10                  15

Xaa Xaa Xaa Xaa Xaa Xaa Xaa Xaa
            20

<210> SEQ ID NO 59
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Leu, Ile or Val
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Asn, Thr, Set or Cys
<220> FEATURE:
```

```
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Leu, Ile or Val
<220> FEATURE:
<221> NAME/KEY: MISC_FEATURE
<222> LOCATION: (13)..(19)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is Leu, Ile or Val
<220> FEATURE:
<221> NAME/KEY: MISC_FEATURE
<222> LOCATION: (21)..(23)
<223> OTHER INFORMATION: Xaa is any amino acid
<220> FEATURE:
<221> NAME/KEY: MISC_FEATURE
<222> LOCATION: (24)..(24)
<223> OTHER INFORMATION: Xaa is Leu, Ile or Val
<220> FEATURE:
<221> NAME/KEY: MISC_FEATURE
<222> LOCATION: (25)..(28)
<223> OTHER INFORMATION: Xaa is any amino acid

<400> SEQUENCE: 59

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 60
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Leu, Ile or Val
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Ile, or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Asn, Thr, Ser or Cys
<220> FEATURE:
<221> NAME/KEY: MISC_FEATURE
<222> LOCATION: (11)..(11)
<223> OTHER INFORMATION: Xaa is any amino acid
```

```
<220> FEATURE:
<221> NAME/KEY: MISC_FEATURE
<222> LOCATION: (12)..(12)
<223> OTHER INFORMATION: Xaa is Leu, Ile, or Val
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Leu, Ile or Val
<220> FEATURE:
<221> NAME/KEY: MISC_FEATURE
<222> LOCATION: (16)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is Leu, Ile, or Val
<220> FEATURE:
<221> NAME/KEY: MISC_FEATURE
<222> LOCATION: (19)..(20)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is Leu, Ile, or Val
<220> FEATURE:
<221> NAME/KEY: MISC_FEATURE
<222> LOCATION: (22)..(22)
<223> OTHER INFORMATION: Xaa is any amino acid

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Leu, Ile or Val
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Ile or Val
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu, Ile or Val
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
```

```
<223> OTHER INFORMATION: Xaa is Asn, Thr, Ser or Cys
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Leu, Ile or Val
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Leu, Ile or Val
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is Leu, Ile or Val
<220> FEATURE:
<221> NAME/KEY: MISC_FEATURE
<222> LOCATION: (20)..(20)
<223> OTHER INFORMATION: Xaa is any amino acid

<400> SEQUENCE: 61

Xaa Xaa Xaa Xaa Xaa Xaa Xaa Xaa Xaa Xaa Xaa Xaa Xaa Xaa Xaa Pro
1               5                   10                  15

Xaa Xaa Pro Xaa
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Leu, Ile or Val
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa  is Leu, Ile or Val
<220> FEATURE:
<221> NAME/KEY: MISC_FEATURE
<222> LOCATION: (6)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Leu, Ile or Val
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Leu, Ile or Val
<220> FEATURE:
<221> NAME/KEY: MISC_FEATURE
```

```
<222> LOCATION: (11)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is Asn, Thr, Ser or Cys
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is Leu, Ile or Val
<220> FEATURE:
<221> NAME/KEY: MISC_FEATURE
<222> LOCATION: (16)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is Leu, Ile or Val
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is any amino acid

<400> SEQUENCE: 62

Xaa Xaa Xaa Xaa Xaa Xaa Xaa Xaa Xaa Xaa Xaa Xaa Xaa Xaa Xaa Xaa
1               5                   10                  15

Xaa Xaa Pro Xaa Gly Xaa Phe Asp
            20
```